United States Patent
Szczepanski

(10) Patent No.: US 6,310,096 B1
(45) Date of Patent: Oct. 30, 2001

(54) CYCLOHEXADIENE-DERIVATIVES AS PESTICIDES

(75) Inventor: Henry Szczepanski, Wallbach (CH)

(73) Assignee: Bayer Aktiengesellschaft, Leverkusen (DE)

(*) Notice: Subject to any disclaimer, the term of this patent is extended or adjusted under 35 U.S.C. 154(b) by 0 days.

(21) Appl. No.: 09/555,613

(22) PCT Filed: Dec. 3, 1998

(86) PCT No.: PCT/EP98/07883

§ 371 Date: Jun. 1, 2000

§ 102(e) Date: Jun. 1, 2000

(87) PCT Pub. No.: WO99/29700

PCT Pub. Date: Jun. 17, 1999

(30) Foreign Application Priority Data

Dec. 5, 1997 (GB) .................................................. 9725883

(51) Int. Cl.⁷ .......................... A01N 37/12; C07C 229/00
(52) U.S. Cl. .............................................. 514/539; 560/35
(58) Field of Search ................. 514/539; 560/35

(56) References Cited

U.S. PATENT DOCUMENTS 5,189,063  2/1993  Klausener et al. ............... 514/530

FOREIGN PATENT DOCUMENTS 0 421 102  4/1991  (EP).
2 076 803  12/1981  (GB).

OTHER PUBLICATIONS

The Journal of Antibiotics (1982), 35(6), pp. 712–720, XP–002107051.

Primary Examiner—Mukund J. Shah
Assistant Examiner—Tamthom N. Truong
(74) Attorney, Agent, or Firm—Joseph C. Gil

(57) ABSTRACT

Certain cyclohexadiene derivatives are useful as pesticides. The derivatives are of the formula:

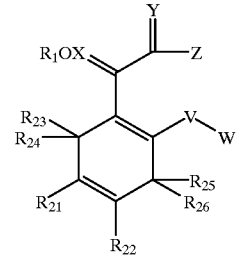

I wherein
X is N;
Y is O; S, S=O or $NR_5$;
Z is $OR_2$, $SR_2$, $N(R_3)R_4$;
V is a direct bond or a 1 to 4 membered, saturated or unsaturated carbon chain which is unsubstituted or substituted by $C_1$–$C_3$alkyl, halogen, hydroxy, $C_1$–$C_4$alkoxy, halo-$C_1$–$C_4$alkoxy or oxo;
W is hydrogen or $C_1$–$C_6$ alkyl or a group of the formula:

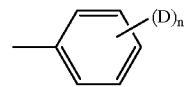

wherein n is an integer of from 0 to 5 and each D is identical or different and represents a moiety selected from the group consisting of halogen, cyano, nitro, $C_1$ to $C_{12}$ alkyl, halo-$C_1$ to $C_{12}$ alkyl, $C_2$ to $C_{12}$ alkenyl, halo-$C_2$ to $C_{12}$ alkenyl, $C_2$ to $C_{12}$ alkynyl, halo-$C_2$ to $C_{12}$ alkynyl, $C_3$ to $C_6$ cycloalkyl, halo-$C_3$ to $C_6$ cycloalkyl, $C_3$ to $C_6$ cycloalkylmethyl, halo-$C_3$ to $C_6$ cycoloalkylmethyl, etc.

7 Claims, No Drawings

CYCLOHEXADIENE-DERIVATIVES AS PESTICIDES

The invention relates to novel pesticidally active compounds of the formula I

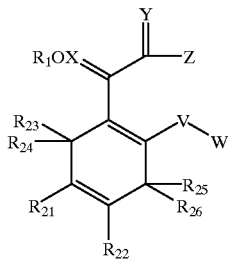

wherein:
- X is CH or N;
- Y is O; S, S=O or $NR_5$;
- Z is $OR_2$, $SR_2$, $N(R_3)R_4$; or
- Y and Z together form a 5- to 7-membered ring which contains 2 or 3 hetero atoms O and/or N and which is unsubstituted or substituted by $C_1$–$C_4$alkyl, halo-$C_1$–$C_4$alkyl, halogen, =O or cyclopropyl;
- V is a direct bond or a 1 to 12 membered, saturated or unsaturated carbon chain which is unsubstituted or substituted by $C_1$–$C_3$alkyl, $C_2$–$C_3$alkylidene, $C_3$–$C_6$cycloalkylidene, halogen, hydroxy, $C_1$–$C_4$alkoxy, halo-$C_1$–$C_4$alkoxy or oxo;
- W is hydrogen or substituted or unsubstituted aryl or substituted or unsubstituted hetaryl or trialkylsilyl;
- $R_1$ is cyclopropyl, $C_1$–$C_6$alkyl or halo-$C_1$–$C_6$alkyl;
- $R_2$ and $R_3$ independently of one another are $C_1$–$C_6$alkyl or halo-$C_1$–$C_6$alkyl;
- $R_4$ and $R_5$ independently of one another are hydrogen, $C_1$–$C_6$alkyl or $C_1$–$C_6$alkoxy;
- $R_{21}$ and $R_{22}$ independently of one another are hydrogen, halogen, $C_1$–$C_8$alkyl or $C_1$–$C_8$alkoxy or $C_1$–$C_8$alkylthio;
- $R_{23}$, $R_{24}$, $R_{25}$, $R_{26}$ independently of one another are hydrogen, halogen, $C_1$–$C_8$alkyl or $C_1$–$C_8$alkoxy.

The formula I embraces all stereoisomeric forms and mixtures of these, such as racemic and diasteromeric mixtures, for example E/Z mixtures. The compounds according to the invention have fungicidal, acaricidal and insecticidal properties and are suitable as active ingredients for use in agriculture, in horticulture and in the hygiene sector. The invention furthermore relates to the preparation of these compounds, to agrochemical compositions which comprise, as active ingredients, at least one of these compounds, and to the use of the active ingredients or of the compositions for protecting plants against attack by harmful microorganisms, and for controlling insects.

2-Alkoximino-2-phenylacetic acid derivatives and 2-alkoxymethylene-2-phenylacetic acid derivatives as pesticides are disclosed, for example, in EP-A-253 213 and EP-A-178 826. Corresponding pesticide compounds which have a cyclohexenyl group instead of the phenyl group are described in EP-A-421 102, those in which the phenyl group is replaced by a cyclohexyl group in EP-A-438 726. The phytofungicidal activity of 1,4-cyclohexadiene-1-alanine is furthermore described in J. of Antibiotics, Vol. XXIII, No. 11, pp.537–541 (1970).

The general terms used hereinabove and hereinbelow have the meanings given hereafter, unless otherwise defined:

Aryl is phenyl, naphthyl, phenanthryl or fluorenyl, in particular phenyl. Hetaryl are 5- or 6-membered aromatic rings which have hetero atoms N, O and/or S, and which can be benzo-fused. Examples are furane, pyrrole, pyridine, pyrimidine, pyrazine, thiazole, oxazole, isoxazole, isothiazole, triazine, quinoline, isoquinoline, pyridazine, pyrazole, imidazole, quinazoline, quinoxaline, benzimidazole, benzofuran, indole, isoindole, benzothiazole, benzoxazole. Heterocyclyl denotes 5- to 7-membered non-aromatic rings which contain 1–3 identical or different hetero atoms N, O, S. Examples are $\Delta^2$-oxazoline, $\Delta^2$-thiazoline; 5,6-dihydro-4H-1,3-thiazine; 5,6-dihydro-4H-1,3-oxazine, pyrrolidine, indoline, piperidine, morpholine, 4-alkylpiperidine, azepine. Alkyl groups are straight-chain or branched, depending on the number of the carbon atoms, for example methyl, ethyl, n-propyl, iso-propyl, n-butyl, sec-butyl, iso-butyl, tert-butyl, sec-amyl, tert-amyl, 1-hexyl or 3-hexyl.

Unsaturated hydrocarbon radicals are alkenyl, alkynyl or alkenynyl groups having not more than 3 multiple bonds, for example butadienyl, hexatrienyl, 2-penten4-ynyl. Alkenyl is to be understood as meaning straight-chain or branched alkenyl, for example allyl, methallyl, 1-methylvinyl or but-2-en-1-yl. Preferred alkenyl radicals are those which have a chain length of 3 to 4 carbon atoms. Alkynyl can also be straight-chain or branched, depending on the number of the carbon atoms, for example ethynyl, propargyl, but-1-yn-1-yl, but-1-yn-3-yl. Propargyl is preferred. Saturated or unsaturated carbon chains as bridging elements are for example alkylene, alkylidene, alkenylene, and alkynylene, as methylene, ethylene, propylene, vinylene, propenylene, methylidyne, ethylidene, butanediylidyne. Halogen or halo are fluorine, chlorine, bromine or iodine, preferably fluorine, chlorine or bromine. Haloalkyl can contain identical or different halogen atoms, for example fluoromethyl, difluoromethyl, difluorochloromethyl, trifluoromethyl, chloromethyl, dichloromethyl, trichloromethyl, 2,2,2-trifluoroethyl, 2-fluoroethyl, 2-chloroethyl, 2,2,2-trichloroethyl, 3,3,3,-trifluoropropyl.

Alkoxy is, for example, methoxy, ethoxy, propyloxy, i-propyloxy, n-butyloxy, iso-butyloxy, sec-butyloxy and tert-butyloxy; preferably methoxy and ethoxy. Haloalkoxy is, for example, difluoromethoxy, trifluoromethoxy, 2,2,2-trifluoroethoxy, 1,1,2,2- tetrafluoroethoxy, 2-fluoroethoxy, 2-chloroethoxy and 2,2-difluoroethoxy. Cycloalkyl is cyclopropyl, cyclobutyl, cyclopentyl or cyclohexyl. Alkanoyl is either straight-chain or branched; examples are formyl, acetyl, propionyl, butyryl, pivaloyl or octanoyl. All the alkyl, alkenyl, alkynyl, haloalkyl, haloalkenyl, haloalkoxy and alkanoyl groups mentioned hereinabove and hereinbelow can be substituted by aryl, hetaryl, aryloxy, hetaryloxy, arylsulfenyl, arylsulfinyl, arylsulfonyl, heterarylsulfenyl, hetarylsulfinyl or heterarylsulfonyl, each of which is unsubstiuted or additionally substituted. All the aryl and hetaryl groups mentioned hereinabove and hereinbelow can be mono- or polysubstituted, for example by halogen, $C_1$–$C_4$alkyl, $C_2$–$C_4$alkenyl, $C_2$–$C_4$alkynyl, $C_1$–$C_4$alkoxy, $C_1$–$C_4$alkylthio, $C_1$–$C_4$haloalkyl, $C_2$–$C_4$haloalkenyl, $C_2$–$C_4$haloalkynyl, $C_1$–$C_4$haloalkoxy, halogen, cyano, cyano-$C_1$–$C_2$alkyl, cyano-$C_1$–$C_2$alkoxy, OH, $NO_2$, SCN, thiocyanomethyl, $Si(CH_3)_3$, $NH_2$, $NH(C_1$–$C_4$alkyl), $N(C_1$–$C_4$alkyl)$_2$, $C_1$–$C_4$alkoxymethyl, $C_1$–$C_4$haloalkylcarbonyl, $C_1$–$C_4$haloalkyloxycarbonyl, $C_1$–$C_4$alkylcarbonyl, $C_1$–$C_4$-alkoxycarbonyl, aminocarbonyl, $C_1$–$C_4$alkylaminocarbonyl, bis ($C_1$–$C_4$alkylamino)carbonyl, arylaminocarbonyl, arylaminothiocarbonyl, $C_1$–$C_4$alkoximinomethyl, —CSNH$_2$, —SH, $C_1$–$C_4$alkylthiomethyl, $C_2$–$C_4$alkenyloxy, $C_2$–$C_4$alkynyloxy, $C_2$–$C_4$haloalkenyloxy, $C_1$–$C_4$alkylsulfinylmethyl, $C_1$–$C_4$alkylsulfonylmethyl, phenylsulfinylmethyl, phenylsulfonylmethyl, trifluoromethylsulfonyl, $C_3$–$C_6$cycloalkyl, $C_1$–$C_4$haloalkylcarbonyloxy, $C_1$–$C_4$alkylcarbonyloxy, $C_1$–$C_4$alkoxycarbonyloxy, haloalkoxycarbonyloxy, aminocarbonyloxy, $C_1$–$C_4$alkylaminocarbonyloxy, bis($C_1$–$C_4$alkylamino)carbonyloxy, arylaminocarbonyloxy, arylaminothiocarbonyioxy. All the abovementioned enumerations are by way of example and not by limitation.

Preferred are the following groups:

(1) Compounds of the formula I in which:

W is hydrogen or $C_1$–$C_6$alkyl or a group a)

in which

D are identical or different substituents halogen, cyano, nitro, $C_1$–$C_{12}$alkyl, halo-$C_1$–$C_6$ alkyl, $C_2$–$C_{12}$alkenyl, halo-$C_2$–$C_{12}$alkenyl, $C_2$–$C_{12}$alkynyl, halo-$C_2$–$C_{12}$alkynyl, free or halogenated $C_3$–$C_6$cycloalkyl, free or halogenated $C_3$–$C_6$cycloalkylmethyl, free or halogenated $C_3$–$C_6$cycloalkylmethyloxy, $C_1$–$C_4$alkoxy, halo-$C_1$–$C_4$alkoxy, $C_2$–$C_6$alkenyloxy, halo-$C_2$–$C_6$alkenyloxy, $C_2$–$C_6$alkynyloxy, halo-$C_2$–$C_6$alkynyloxy, $C_2$–$C_{12}$alkoxyalkyl, $C_1$–$C_4$alkoxycarbonyl, $C_1$–$C_6$alkylcarbonyl, it being possible for all the abovementioned alkyl, alkenyl or alkynyl groups to be substituted by aryl or hetaryl, aryloxy or hetaryloxy, arylsulfenyl, arylsulfinyl, arylsulfonyl, hetarylsulfenyl, hetarylsulfinyl or hetarylsulfonyl radicals, each of which can be additionally substituted or unsubstituted; furthermore substituted or unsubstituted aryl, substituted or unsubstituted hetaryl, substituted or unsubstituted heterocyclyl, substituted or unsubstituted arylcarbonyl, substituted or unsubstituted aryloxy, substituted or unsubstituted benzyl, substituted or unsubstituted cyclohexenyl, substituted or unsubstituted cyclohexenylalkoxy, substituted or unsubstituted cyclohexenylalkylthio, substituted or unsubstituted cyclohexadienyl, substituted or unsubstituted cyclohexadienylalkoxy, substituted or unsubstituted cyclohexadienylalkylthio, substituted or unsubstituted fused ring having up to 14 C atoms, or in which D is once the group

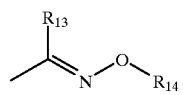

in which $R_{13}$ is hydrogen, cyano, $C_1$–$C_6$alkyl, $C_3$–$C_6$cycloalkyl, $C_1$–$C_6$alkoxycarbonyl, $C_1$–$C_6$acyl, $C_1$–$C_2$-alkoximino-$C_1$–$C_6$alkyl, aryl, hetaryl, heterocyclyl, naphthyl; $C_1$–$C_6$alkoxy, aryloxy, hetaryloxy, $C_1$–$C_6$alkylamino, bis($C_1$–$C_6$-alkyl)amino, arylamino, hetarylamino, in which all the abovementioned radicals (with the exception of cyano) can be unsubstituted or substituted by alkyl, alkoxy, haloalkyl, haloalkoxy, alkylthio, alkylsulfenyl, alkylsulfinyl, halogen, nitro, cyano, aryl, aryloxy, hetaryl, hetaryloxy; or $R_{13}$ is the group

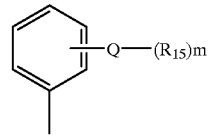

in which $R_{15}$ is hydrogen, $C_1$–$C_6$alkyl, halo-$C_1$–$C_6$alkyl, $C_1$–$C_6$alkoxy, halo-$C_1$–$C_6$alkoxy, halogen, $C_3$–$C_6$cycloalkyl which is unsubstituted or substituted by 1 to 5 halogen atoms, $C_2$–$C_6$alkenyl; halo-$C_2$–$C_6$alkenyl, substituted or unsubstituted $C_2$–$C_6$alkynyl; aryl, hetaryl or heterocyclyl, all three of which independently of one another are unsubstituted or monosubstituted to pentasubstituted by $C_1$–$C_6$alkyl, halo-$C_1$–$C_6$alkyl, halogen, $C_1$–$C_6$alkoxy or halo-$C_1$–$C_6$alkoxy; tri($C_1$–$C_4$-alkyl)silyl, di($C_1$–$C_4$-alkyl)phenylsilyl;

where, if m is greater than 1, the radicals $R_{15}$ can be identical or different;

Q is a direct bond, $C_1$–$C_8$alkylene, $C_2$–$C_6$alkenylene, $C_2$–$C_6$alkynylene, O, O($C_1$–$C_6$alkylene), ($C_1$–$C_6$alkylene)O, S(=O)$_p$, S(=O)$_p$($C_1$–$C_6$alkylene) or ($C_1$–$C_6$alkylene)S(=O)$_p$;

n is 0, 1, 2, 3, 4 or 5;

m is 0, 1, 2, 3, 4 or 5;

p is 0, 1 or 2; and $R_{14}$ is hydrogen; $C_1$–$C_6$alkyl; $C_1$–$C_6$haloalkyl having 1 to 15 halogen atoms; $C_1$–$C_4$alkoxy-$C_1$–$C_2$alkyl; $C_2$–$C_4$alkenyl-$C_1$–$C_2$alkyl which is unsubstituted or substituted by 1 to 3 halogen atoms; $C_2$–$C_4$alkynyl-$C_1$–$C_2$alkyl; $C_3$–$C_6$cycloalkyl which is unsubstituted or substituted by 1 to 4 halogen atoms; $C_3$–$C_6$cycloalkyl-$C_1$–$C_4$alkyl which is unsubstituted or substituted by 1 to 4 halogen atoms; cyano-$C_1$–$C_4$alkyl; $C_1$–$C_4$alkoxycarbonyl-$C_1$–$C_4$alkyl; phenyl-$C_1$–$C_3$alkyl which is unsubstituted or substituted by halogen, $C_1$–$C_3$alkyl, Cl-$C_4$alkoxy, $C_1$–$C_4$haloalkyl, cyano, nitro, $C_1$–$C_4$alkylenedioxy, it being possible for the phenyl group to be substituted by 1 to 3 identical or different substitutents; phenyl which is unsubstituted or monosubstituted or disubstituted by independent substituents from the series consisting of $C_1$–$C_4$alkyl, $C_1$–$C_4$alkoxy, halogen, $C_1$–$C_2$haloalkyl having 1 to 3 halogen atoms, nitro or cyano; pyridyl which is unsubstituted or monosubstituted or disubstituted by independent substituents from the series consisting of $C_1$–$C_4$alkyl, $C_1$–$C_4$alkoxy, halogen, $C_1$–$C_2$haloalkyl having 1 to 3 halogen atoms, nitro or cyano.

(2) Compounds of the formula I in which:

$R_1$ is methyl;

$R_2$, $R_3$ und $R_5$ independently of one another are $C_1$–$C_2$alkyl, preferably methyl;

$R_4$ is hydrogen.

(3) Compounds of the formula I in which:

X is N;

Y is O; S, or S=O, preferably O;

Z is OR$_2$, SR$_2$, N(R$_3$)H; preferably OR$_2$, SR$_2$;

$R_2$ and $R_3$ are $C_1$–$C_2$alkyl, preferably methyl.

(4) Compounds of the formula I in which:

X is CH;
Y is O; S, or S=O, preferably O;
Z is OR$_2$;
R$_2$ is C$_1$–C$_2$-Alkyl, preferably methyl.

(5) Compounds of the formula I in which Y and Z together are a group a)

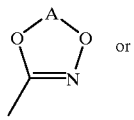  or b)

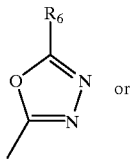  or c)

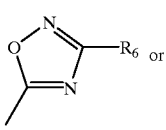  or d)

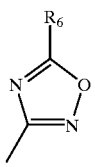

and in which:
A is alkanediyl having 1 to 3 carbon atoms which is unsubstituted or substituted by methyl, preferably dimethylene (ethane-1,2-diyl);
R$_6$ is hydrogen, C$_1$–C$_3$alkyl, cyclopropyl or CF$_3$;

(6) Compounds of the formula I in which:
V is a direct bond or a 1 to 4 membered, saturated or unsaturated carbon chain which is unsubstituted or substituted by C$_1$–C$_3$alkyl, halogen, hydroxy, C$_1$–C$_4$alkoxy, halo-C$_1$–C$_4$alkoxy or oxo;
R$_{21}$ and R$_{22}$ independently of one another are hydrogen, chlorine, bromine, C$_1$–C$_4$alkyl, or C$_1$–C$_4$alkoxy, in particular methyl;
R$_{23}$, R$_{24}$, R$_{25}$, R$_{26}$ are hydrogen.

(7) Compounds of the formula I in which:
X is CH or N;
Y is O;
Z is OCH$_3$ or NHCH$_3$;
V is —CH$_2$—, —CH(CH$_3$)—, —CH(CH$_3$)$_2$—, —(CH$_2$)$_2$—, —(CH$_2$)$_3$—, —CH=CH—, —C≡C—, C=O, —CH$_2$C(=O)— or —(C=O)CH$_2$—
W is a substituted or unsubstituted phenyl;
R$_{21}$ and R$_{22}$ independently of one another are hydrogen, chlorine or methyl, in particular methyl;
R$_{23}$, R$_{24}$, R$_{25}$, R$_{26}$ are hydrogen.

(8) Compounds of the formula I in which:
V is —CH$_2$—, —(CH$_2$)$_2$—, —(CH$_2$)$_3$—, —CH=CH—, —C≡C—, C=O, R$_{21}$ and R$_{22}$ independently of one another are halogen, chlorine, bromine, C$_1$–C$_4$alkyl or C$_1$–C$_4$alkoxy; in particular methyl;
R$_{23}$, R$_{24}$, R$_{25}$, R$_{26}$ are hydrogen.

(9) Compounds of the formula I in which:
W is a phenyl which is unsubstituted or substituted by C$_1$–C$_8$alkyl, halo-C$_1$–C$_{6alkyl}$, C$_2$–C$_4$alkenyl, halo-C$_2$–C$_4$alkenyl, C$_2$–C$_4$alkynyl, halo-C$_2$–C$_4$alkynyl, C$_1$–C$_4$alkoxy, halo-C$_1$–C$_4$alkoxy, C$_2$–C$_6$alkenyloxy, halo-C$_2$–C$_4$alkenyloxy, C$_2$–C$_4$alkynyloxy, halo-C$_2$–C$_4$alkynyloxy, C$_1$–C$_4$alkoxycarbonyl, C$_1$–C$_6$alkylcarbonyl, the abovementioned alkyl, alkenyl and alkynyl groups being unsubstituted or further substituted by aryl, hetaryl, aryloxy, hetaryloxy, arylsulfenyl, arylsulfinyl, arylsulfonyl, hetarylsulfenyl, hetarylsulfenyl or hetarylsulfonyl, each of which is unsubstituted or additionally substituted; furthermore aryl, hetaryl, heterocyclyl, arylcarbonyl, aryloxy, benzyl, cycloalkyl, cyclohexenyl, cyclohexenylalkoxy, cyclohexenylalkylthio, cyclohexadienyl, cyclohexadienylalkoxy, cyclohexadienylalkylthio, all the abovementioned cyclic groups being unsubstituted or mono- or polysubstituted by halogen, C$_1$–C$_4$alkyl, C$_2$–C$_4$alkenyl, C$_2$–C$_4$alkynyl, C$_1$–C$_4$alkoxy, C$_1$–C$_4$alkylthio, C$_1$–C$_4$haloalkyl, C$_2$–C$_4$haloalkenyl, C$_2$–C$_4$haloalkynyl, C$_1$–C$_4$haloalkoxy, halogen, cyano, cyano-C$_1$–C$_2$alkyl, cyano-C$_1$–C$_2$alkoxy, OH, NO$_2$, SCN, thiocyanomethyl, Si(CH$_3$)$_3$, NH$_2$, NH(C$_1$–C$_4$alkyl), N(C$_1$–C$_4$alkyl)$_2$, C$_1$–C$_4$alkoxymethyl, C$_1$–C$_4$haloalkylcarbonyl, C$_1$–C$_4$haloalkyloxycarbonyl, C$_1$–C$_4$alkylcarbonyl, C$_1$–C$_4$alkoxycarbonyl, aminocarbonyl, C$_1$–C$_4$-alkylaminocarbonyl, bis(C$_1$–C$_4$alkylamino)carbonyl, arylaminocarbonyl, arylaminothiocarbonyl, C$_1$–C$_4$alkoximinomethyl, —CSNH$_2$, —SH, C$_1$–C$_4$alkylthiomethyl, C$_2$–C$_4$alkenyloxy, C$_2$–C$_4$alkynyloxy, C$_2$–C$_4$haloalkenyloxy, C$_1$–C$_4$alkylsulfinylmethyl, C$_1$–C$_4$-alkylsulfonylmethyl, phenylsulfinylmethyl, phenylsulfonylmethyl, trifluoromethylsulfonyl, C$_3$–C$_6$-cycloalkyl, C$_1$–C$_4$haloalkylcarbonyloxy, C$_1$–C$_4$alkylcarbonyloxy, C$_1$–C$_4$alkoxycarbonyloxy, haloalkoxycarbonyloxy, aminocarbonyloxy, C$_1$–C$_4$alkylaminocarbonyloxy, bis(C$_1$–C$_4$-alkylamino)carbonyloxy, arylaminocarbonyloxy or arylaminothiocarbonyloxy.

(10) Amongst (1), those, in which:
D is halogen, C$_1$–C$_4$alkyl, halo-C$_1$–C$_4$alkyl, C$_2$–C$_4$alkenyl, C$_2$–C$_4$alkynyl, free or chlorinated cyclopropylmethyl, C$_1$–C$_4$alkoxy, halo-C$_1$–C$_4$alkoxy, C$_2$–C$_{12}$alkoxyalkyl, C$_1$–C$_4$ acyl, C$_1$–C$_4$alkoxycarbonyl, free or chlorinated cyclopropylmethyloxy, or substituted or unsubstituted aryl, substituted or unsubstituted aryloxy, or substituted or unsubstituted benzyl, where the substituents on phenyl, phenoxy and benzyl are selected from the series consisting of halogen, nitro, C$_1$–C$_2$alkyl, halo-C$_1$–C$_2$alkyl, C$_2$–C$_4$alkenyl, C$_2$–C$_4$alkynyl, C$_1$–C$_2$alkoxy, halo-C$_1$–C$_2$alkoxy, C$_2$–C$_{12}$alkoxyalkyl;
n is 0, 1, 2 or 3.

(11) Amongst (10), those, in which:
D is halogen, C$_1$–C$_4$alkyl, halo-C$_1$–C$_4$alkyl, C$_2$–C$_4$alkenyl, C$_2$–C$_4$alkynyl, free or chlorinated cyclopropylmethyl, C$_1$–C$_4$alkoxy, halo-C$_1$–C$_4$alkoxy, C$_1$–C$_4$ acyl, C$_1$–C$_4$alkoxycarbonyl, free or chlorinated cyclopropylmethyloxy, n is 0, 1 or 2.
(12) Amongst (1), those, in which:
D is the group

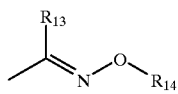

in which
R$_{13}$ is hydrogen, cyano, C$_1$–C$_4$alkyl, cyclopropyl, C$_1$–C$_4$alkoxycarbonyl, C$_1$–C$_4$acyl, C$_1$–C$_2$alkoximino-C$_1$–C$_6$alkyl, or the group

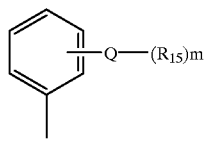

in which
R$_{15}$ is C$_1$–C$_6$alkyl, halo-C$_1$–C$_6$alkyl, C$_1$–C$_6$alkoxy, halo-C$_1$–C$_6$alkoxy, halogen, C$_3$–C$_6$cycloalkyl, which is unsubstituted or substituted by 1 to 5 halogen atoms, C$_2$–C$_6$alkenyl; halo-C$_2$–C$_6$alkenyl, substituted or unsubstituted C$_2$–C$_6$alkynyl; aryl, hetaryl or heterocyclyl, all three of which independently of one another are unsubstituted or monosubstituted to pentasubstituted by C$_1$–C$_6$alkyl, halo-C$_1$–C$_6$alkyl, halogen, C$_1$–C$_6$alkoxy or halo-C$_1$–C$_6$alkoxy; tri(C$_1$–C$_4$-alkyl)silyl, di(C$_1$–C$_4$alkyl)phenylsilyl;
where, it m is greater than 1, it is possible for the radicals R$_{15}$ to be identical or different; Q is a direct bond, C$_1$–C$_8$alkylene, C$_2$–C$_6$alkenylene, C$_2$–C$_6$alkynylene, O,O(C$_1$–C$_6$alkylene), (C$_1$–C$_6$alkylene)O, S(=O)$_p$, S(=O)$_p$(C$_1$–C$_6$alkylene) or (C$_1$–C$_6$alkylene)S(=O)$_p$;
n is 0,1,2, or 3;
m is 0, 1, 2, or 3;
p is 0, 1 or 2; and
R$_{14}$ is hydrogen; C$_1$–C$_4$alkyl; C$_1$–C$_4$haloalkyl having 1 to 6 halogen atoms; C$_2$–C$_4$alkenyl; C$_2$–C$_4$haloalkenyl having 1 to 3 halogen atoms.
(13) Amongst (12) those, in which:
R$_{15}$ is C$_1$–C$_6$alkyl, halo-C$_1$–C$_6$alkyl, cyclopropyl which is unsubstituted or substituted by 1 to 5 chlorine atoms, C$_2$–C$_6$alkenyl which is unsubstituted or substituted by 1 to 3 halogen atoms, or unsubstituted or substituted C$_2$–C$_6$alkynyl; furthermore phenyl, which is unsubstituted or monosubstituted to pentasubstituted by C$_1$–C$_6$alkyl, halo-C$_1$–C$_6$alkyl, halogen, C$_1$–C$_6$alkoxy or halo-C$_1$–C$_6$alkoxy; or pyridyl which is unsubstituted or monosubstituted to pentasubstituted by C$_1$–C$_6$alkyl, halo-C$_1$–C$_6$alkyl, halo, C$_1$–C$_6$alkoxy or halo-C$_1$–C$_6$alkoxy;
Q is a direct bond, C$_1$–C$_4$alkylene, O, O(C$_1$–C$_4$alkylene), (C$_1$–C$_4$alkylene)O,
m is 0, 1, 2.
(14) Compounds of the formula I in which:
R$_{13}$ is hetaryl or heterocyclyl, which, independently of one another, are unsubstituted or monosubstituted to pentasubstituted by C$_1$–C$_6$alkyl, halo-C$_1$–C$_6$alkyl, halogen, C$_1$–C$_6$-alkoxy or halo-C$_1$–C$_6$alkoxy.
(15) Compounds of the formula I in which:
W is substituted or unsubstituted pyridyl, pyrimidinyl, imidazolyl, thiazolyl, 1,3,4-thiadiazolyl, triazolyl, thienyl, furanyl, pyrrolyl, quinolyl, isoquinolyl, benzoxazolyl, quinoxalinyl, benzothiazolyl, benzimidazolyl, or indolyl.
(16) Amongst (15) those, in which:
W is pyridyl or pyrimidinyl, each of which is unsubstituted or substituted by C$_1$–C$_4$alkyl, halo-C$_1$–C$_4$alkyl, C$_2$–C$_6$alkenyl, halo-C$_2$–C$_6$alkenyl, C$_2$–C$_6$alkynyl, halo-C$_2$–C$_6$alkynyl, C$_1$–C$_4$alkoxy, halo-C$_1$–C$_4$alkoxy, C$_2$–C$_{12}$alkoxyalkyl, C$_1$–C$_6$acyl, C$_1$–C$_4$alkoxycarbonyl, substituted or unsubstituted phenyl, substituted or unsubstituted phenoxy, or substituted or unsubstituted benzyl.

Compounds of the formula I can be prepared as shown in reaction schemes 1 and 2.

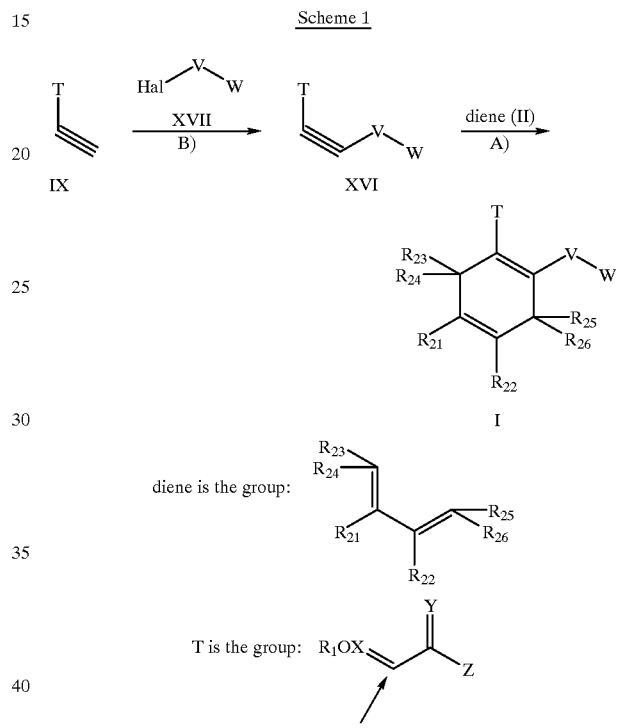

Scheme 1

W is as defined for formula I;
Hal is halogen
The individual reaction steps can be carried out as follows:
A) under conditions known from, and applicable to, Diels-Alder reactions, in the presence or absence of solvents, and in the presence or absence of a catalyst; at –40 to 250° C., preferably –20 to 200° C., in particular 100–200° C.
B) under conditions known for, and applicable to, Heck reactions, in the presence of a Pd catalyst (for example F. A. Carey and R. J. Sundberg, Advanced Organic Chemistry, pages 418–420, Plenum Press 1990).
C) reaction under conditions suitable for C-Si bond cleavage.
D) reaction in a solvent under alkaline conditions.
Reaction conditions, as solvents, bases, catalyts etc. are known to the person skilled in the art.
Typical reaction conditions can be seen from the examples.
The cyclohexadiene derivatives of the formula I can be converted by known methods, either by dehydrogenation to the corresponding aromatic compounds or by hydrogenation into the corresponding cyclohexene or cyclohexane derivatives.

The invention also relates to novel starting materials and intermediates used for the preparation of the compounds of the formula I, their use and processes for their preparation.

Scheme 2

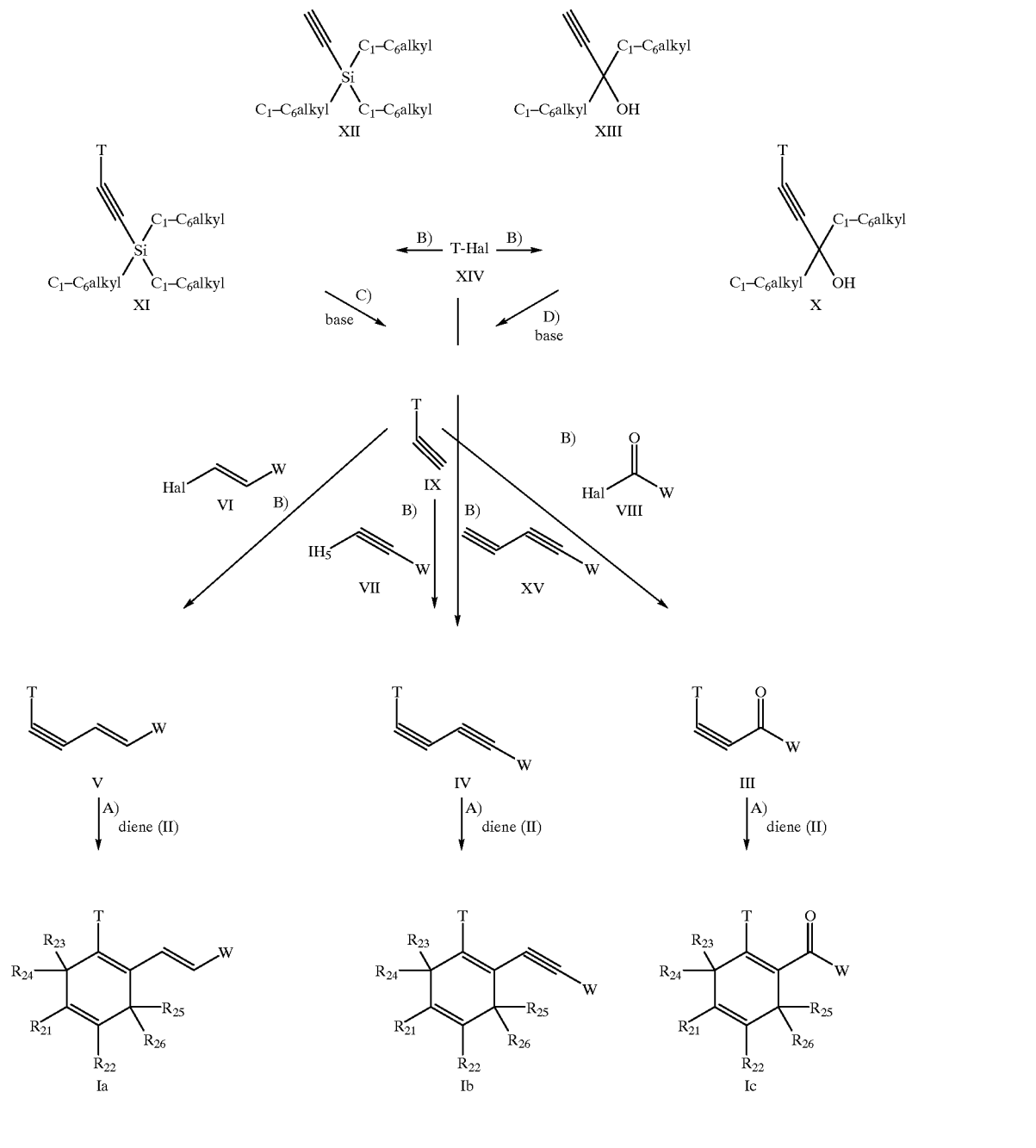

The following processes are of particular importance:

(1) Process for the preparation of a compound of the formula I which comprises reacting a compound of the formula II with a compound of the formula XVI, with or without solvent under Diels-Alder conditions

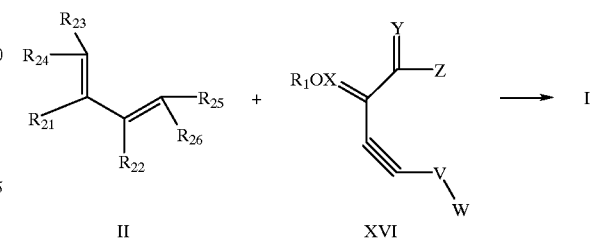

in which X, Y, Z, $R_1$, V, W and $R_{21}$ to $R_{26}$ have the meanings given for formula I.

(2) Process for the preparation of a compound of the formula Ic, which comprises reacting a compound of the formula II with a compound of the formula III, with or without solvent under Diels-Alder conditions

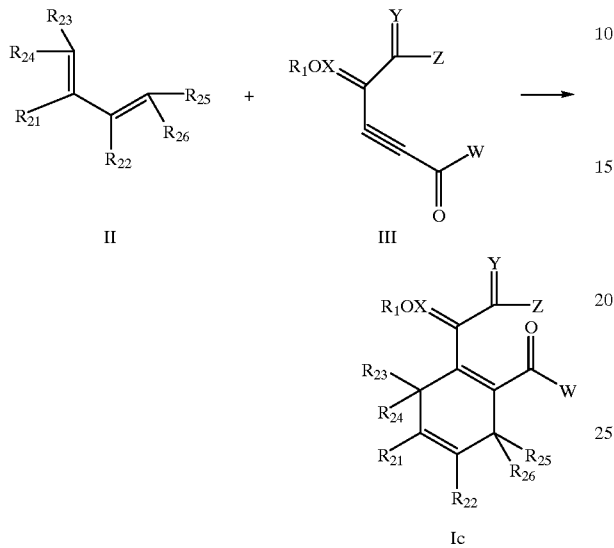

in which X, Y, Z, $R_1$, W and $R_{21}$ to $R_{26}$ have the meanings given for formula I (3) Process for the preparation of a compound of the formula Ib, which comprises reacting a compound of the formula II with a compound of the formula IV, with or without solvent under Diels-Alder conditions

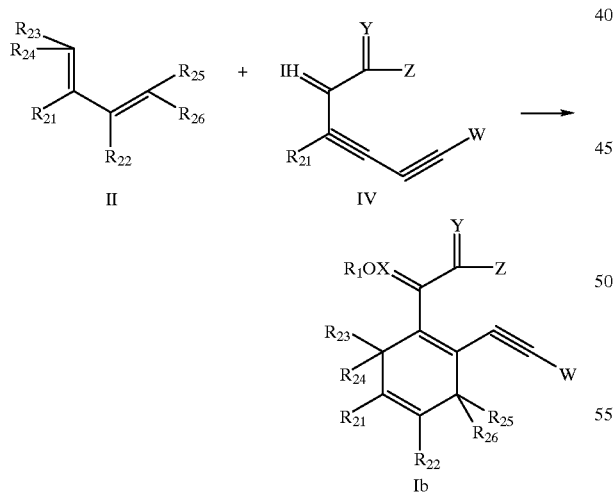

in which X, Y, Z, $R_1$, W and $R_{21}$ to $R_{26}$ have the meanings given for formula I.

(4) Process for the preparation of a compound of the formula XVI which comprises reacting a compound of the formula IX with a compound of the formula XVII in presence of a Pd catalyst ("Heck"-reaction)

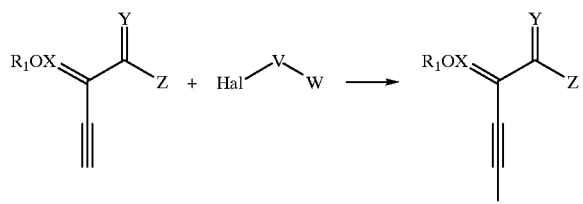

in which X, Y, Z, $R_1$, V, W have the meanings given for formula I and wherein Hal is halogen.

The invention relates also to intermediates of the formula

XVI

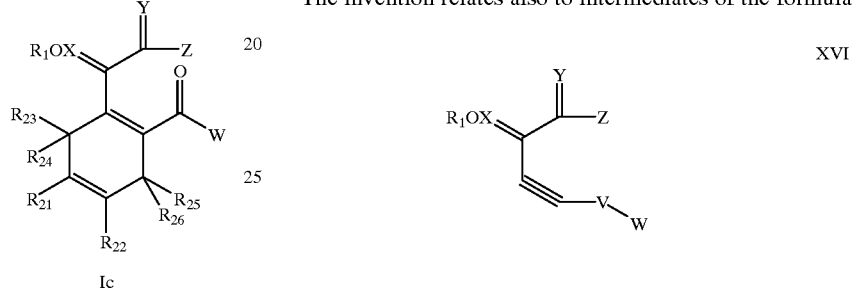

as well as to intermediates of the formulae in which X, Y, Z, $R_1$, and W have the meanings given for formula I Of particular importance are the following compounds

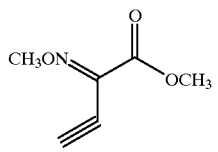

IXa

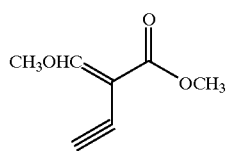

IXb

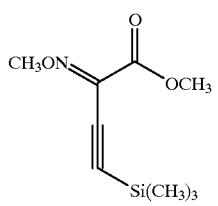

XIa

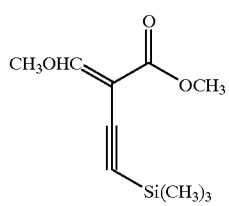

XIb

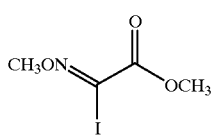

XIVa2

The compounds of the formula T-Hal (XIV) in which T has the above mentioned meanings and Hal is halogen can be prepared as described, for example, in WO/20569.

The groups mentioned for X, Y and Z in formula I can be converted into each other by known methods, for example WO 94/26700 and WO 95/04728, both at the final level and at any suitable intermediate level.

The compounds of the formula I can be employed preventively and/or curatively in the agricultural sector and related fields as active ingredients in the control of plant pests. The active ingredients of the formula I according to the invention are distinguished by a good activity, even at low rates of concentration, and by the fact that they are well tolerated by plants and are environmentally friendly. They have very advantageous, in particular systemic, properties and can be employed for protection of a large number of crop plants. Using the active ingredients of the formula I, it is possible to contain or destroy the pests which are found on plants or plant organs (fruits, flowers, foliage, stalks, tubers, roots) of a variety of useful plants, and even plant organs which grow at a later point in time remain unharmed, for example by phytopathogenic microorganisms.

Moreover, the compounds I can be employed as seed-dressing agents for the treatment of seeds (fruits, tubers, kernels) and plant cuttings as a protection against fungal infections and against soil-borne phytopathogenic fungi.

The compounds I act for example against the phytopathogenic fungi which belong to the following classes: Fungi imperfecti (for example Botrytis, Pyricularia, Helminthosporium, Fusarium, Septoria, Cercospora and Alternaria); Basidiomycetes (for example Rhizoctonia, Hemileia, Puccinia); Ascomycetes (for example Venturia and Erysiphe, Podosphaera, Monilinia, Uncinula) and Oomycetes (for example Phytophthora, Pythium, Plasmopara).

Target crops for the application in crop protection are, within the scope of the invention, for example the following plant species: cereals,(wheat, barley, rye, oats, rice, maize, sorghum and related species); beet (sugar and fodder beet); pome fruit, stone fruit, soft fruit (apples, pears, plums, peaches, almonds, cherries, strawberries, raspberries, blackberries); leguminous plants (beans, lentils, peas, soya); oil crops (oil seed rape, mustard, poppies, olives, sunflowers, coconut, castor, cocoa, peanuts); cucurbits (pumpkin, cucumbers, melons); fibre crops (cotton, flax, hemp, jute); citrus fruit (oranges, lemons, grapefruit, tangerines); various vegetables (spinach, lettuce, asparagus, cabbages, carrots, onions, tomatoes, potatoes, bell peppers); the laurel family (avocado, Cinnamonium, camphor), and plants such as tobacco, nuts, coffee, aubergines, sugar cane, tea, pepper, grapevines, hops, the plantain family, latex plants and ornamentals.

The compounds of the formula I according to the invention are furthermore valuable active ingredients against insects and pests from the order Acarina, as found on useful plants and ornamentals in agriculture, in horticulture and in forests, while being well tolerated by warm-blooded species, fish and plants. The compounds of the formula I are particularly suitable for controlling pests in cotton, vegetable, fruit and rice crops, such as spider mites, aphids, caterpillars of lepidopterans and rice leafhoppers. Pests which can be controlled are mainly spider mites such as *Panonychus ulmi*, aphids such as *Aphis craccivora*, caterpillars lepidopterans, such as those of *Heliothis virescens*, and rice leafhoppers such as *Nilaparvata lugens* or *Nephotettix cincticeps*. The good pesticidal activity of the compounds I according to the invention corresponds to a mortality of at least 50–60% of the above mentioned pests.

Further fields of application of the active ingredients according to the invention are the protection of stored products and of materials, in which case the stored material is protected against rotting and becoming mouldy and also against animal pests (for example grain weevil, mites, maggots and the like). In the hygiene sector, compounds of the formula I effect successful control of animal parasites such as ticks, mites, warble flies and the like on domestic animals and productive livestock. The compounds I act against individual or all developmental stages of normally sensitive, but also resistant species of pests. In the present context, their activity may become apparent for example in destruction of the pests, either immediately or only after some time has elapsed, for example during ecdysis, or in a reduced oviposition and/or hatching rate.

Active ingredients I are normally used in the form of compositions and can be applied to the plant or area to be treated simultaneously with other active ingredients, or in succession. These other active ingredients can be, for example, fertilizers, trace element mediators or other preparations which affect plant growth. In this context, selective herbicides, but also insecticides, fungicides, bactericides, nematicides, molluscicides or mixtures of a plurality of these together with, if desired, other carriers conventionally used in the art of formulation, surfactants of other application-enhancing additives may also be used.

Suitable carriers and additives can be solid or liquid and are substances expediently used in the art of formulation, for example natural or regenerated mineral substances, solvents, dispersants, wetting agents, tackifiers, thickeners, binders or fertilizers.

A preferred process for applying an active ingredient of the formula I, or of an agrochemical composition which comprises at least one of these active ingredients, is application to the foliage (foliar application). Frequency and rate of application depend on the risk of infestation with the pathogen in question. Alternatively, the active ingredients I can reach the plant through the soil via the root system (systemic action), by drenching the locus of the plant with a liquid preparation or by incorporating the substances into the soil in solid form, for example in the form of granules (soil application). In the case of paddy rice, such granules can be metered into the flooded paddy field. Alternatively, the compounds I can be applied to seed kernels for the purposes of seed treatment (coating), either by soaking the kernels or tubers in a liquid preparation of the active ingredient or by coating them with a solid preparation.

The compounds I are employed as such or, preferably, together with the auxiliaries conventionally used in the art of formulation. To this end, they are processed in a known manner, expediently to give, for example, emulsion concentrates, spreadable pastes, directly sprayable or dilutable solutions, dilute emulsions, wettable powders, soluble powders, dusts or granules, for example by encapsulation in, for example, polymeric substances. The methods of application, such as spraying, atomizing, dusting, scattering, brushing on or pouring, and the type of composition are selected to suit the intended aims and prevailing circumstances.

Useful rates for application are, generally, 1 g to 2 kg of active substance (a.s.) per hectare (ha), preferably 10 g to 1 kg of a.s/ha, in particular 20 g to 600 g a.s/ha. When used as a seed-dressing agent, it is advantageous to use doses of from 10 mg to 1 g of active substance per kg of seed.

The formulations, i.e. the compositions, preparations or products comprising the active ingredient of the formula I and, if desired, a solid or liquid additive, prepared in a known manner, for example by intimately mixing and/or grinding the active ingredient with extenders, such as solvents, solid carriers and, if desired, surface-active compounds (surfactants).

The agrochemical compositions naormally comprise 0,1 to 99 percent by weight, in particular 0.1 to 95 percent by weight, of active ingredient of the formula I, 99.9 to 1 percent by weight, in particular 99.8 to 5 percent by weight, of a solid or liquid additive and 0 to 25 percent by weight, in particular 0.1 to 25 percent by weight, of a surfactant. The compositions may also comprise other additives such as stabilizers, antifoams, viscosity regulators, binders or tackifiers, and also fertilizers or other active ingredients for achieving specific effects.

The compounds of formula I can be mixed with other pesticides, in particular fungicides, producing in some cases unexpected synergistic effects.

Especially preferred mixing partners are
azoles, as azaconazole, bitertanol, bromuconazole, cyproconazole, difenoconazole, diniconazole, epoxiconazole, fenbuconazole, fluquinconazole, flusilazole, flutriafol, hexaconazole, imazalil, imibenconazole, ipconazole, metconazole, myclobutanil, pefurazoate, penconazole, pyrifenox, prochloraz, propiconazole, tebuconazole, tetraconazole, triadimefon, triadimenol, triflumizole, triticonazote;
pyrimidinyl carbinoles, as ancymidol, fenarimol, nuarimol;
2-amino-pyrimidines, as bupirimate, dimethirimol, ethirimol; morpholines, as dodemorph, fenpropidin, fenpropimorph, spiroxamin, tridemorph;
anilinopyrimidines, as cyprodinil, mepanipyrim, pyrimethanil; pyrroles, as fenpiclonil, fludioxonil;
phenylamides, as benalaxyl, turalaxyl, metalaxyl, R-metalaxyl, ofurace, oxadixyl; benzimidazoles, as benomyl, carbendazim, debacarb, tuberidazole, thiabendazole; dicarboximides, as chlozolinate, dichlozoline, iprodione, myclozoline, procymidone, vinclozolin;
carboxamides, as carboxin, fenfuram, flutolanil, mepronil, oxycarboxin, thifluzamide; guanidines, as guazatine, dodine, iminoctadine;
strobilurines, as azoxystrobin, kresoxim-methyl, SSF-1 26 (metominostrobin or fenominostrobin; SSF-129 (α-methoximino-N-methyl-2-[(2,5-dimethylphenoxy) methyl]-benzeneacetamide, trifloxystrobin (2-[α-([(α-methyl-3-trifluomiethyl-benzyl)imino]-oxy}-o-tolyl]-glyoxylsäure-methylester-O-methyloxim);
dithiocarbamates, as terbam, mancozeb, maneb, metiram, propineb, thiram, zineb, ziram;
N-halomethylthiodicarboximides, as captafol, captan, dichlofluanid, fluoromide, folpet, tolyfluanid;
copper compounds, as bordeaux-mixture, copper hydroxide, copper oxychloride, copper sulfate, cuprous oxide, mancopper, oxine-copper;
nitrophenol-derivatives, as dinocap, nitrothal-isopropyl;
organo-P-derivatives, as edifenphos, iprobenphos, isoprothiolane, phosdiphen, pyrazophos, tolclofos-methyl;
other compounds, as acibenzolar-S-methyl, anilazine, blasticidin-S, chinomethionat, chloroneb, chlorothalonil, cymoxanil, dichlone, diclomezine, dicloran, diethofencarb, dimethomorph, dithianon, etridiazole, famoxadone, fentin, ferimzone,fluazinam, flusulfamide, tenhexamid, fosetyl-aluminium, hymexazol, kasugamycin, methasulfocarb, pencycuron, phthalide, polyoxins, probenazole, propamocarb, pyroquilon, quinoxyfen, quintozene, sulfur, triazoxide, tricyclazole, triforine, validamycin.

PREPARATION EXAMPLES

Temperatures in ° Celsius. Abbreviations: Me=methyl; Et=ethyl; Pr=n-propyl; i-Pr =isopropyl; Bu=butyl; i-Bu= isobutyl; Ph=phenyl; THF=tetrahydrofuran; TPP= triphenylphosphine.

H-1: Preparation of Compound 18a.2.

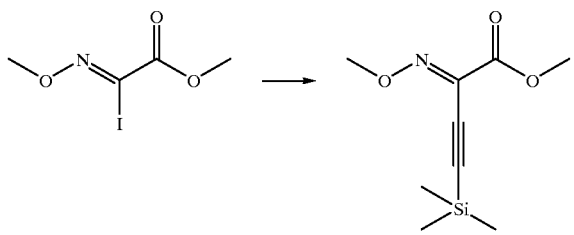

720 mg of trimethylsilylacetylene and 0.15 g of Pd (TPP)2 C12 are added to a solution of 1820 mg of methyl 2-methoxyiminoiodooxalate in 1 ml of triethylamine and 7 ml of DMSO. The mixture is now stirred for 3 hours at 650° and filtered with suction. The filtrate is evaporated and the residue is chromatographed on silica gel (ether/hexane 1:2). This gives 1540 mg of 2-methoxyimino-4-trimethylsilanyl-but-3-ynoic acid methyl ester.

H-2: Preparation of Compound 18a.1.

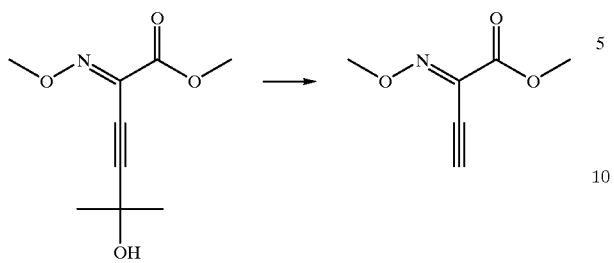

To a solution of 1820 mg of 5-hydroxy-2-methoxyimino-5-methyl-hex-3-ynoic acid methyl ester in 10 ml of xylene 500 mg of sodium hydroxide are added at 130°. The mixture is now stirred for 5 minutes, cooled to room temperature and filtered with suction. The filtrate is evaporated and the residue is chromatographed on silica gel (etherhexane 1:2). This gives 440 mg of 2-methoxyimino-but-3-ynoic acid methyl ester as crystals of melting point 82–83°.

H-3: Preparation of Compound 18a.1.

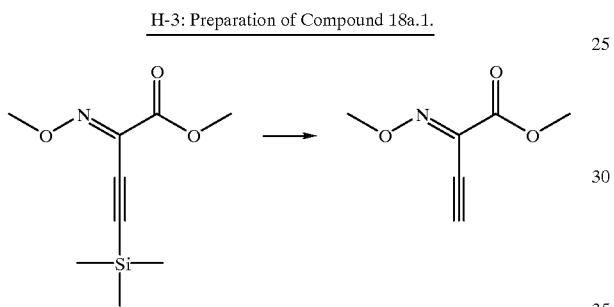

To a solution of 1820 mg of of 2-methoxyimino-4-trimethylsilanyl-but-3-ynoic acid methyl ester in 10 ml of methanol 500 mg of sodium carbonate are added. The mixture is now stirred for 5 hours at room temperature and filtered with suction. The filtrate is evaporated and the residue is chromatographed on silica gel (ether/hexane 1:2). This gives 940 mg of 2-methoxyimino-but-3-ynoic acid methyl ester as crystals of melting point 82–83°.

H-4: Preparation.

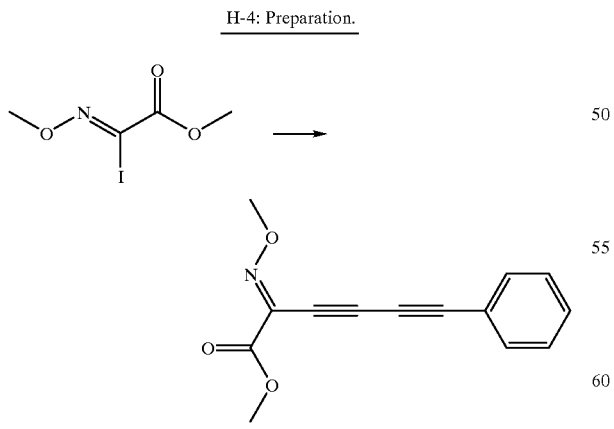

720 mg of phenyldiacetylene and 0.15 g of Pd (TPP)2 Cl2 are added to a solution of 1820 mg of methyl 2-methoxyiminoiodooxalate in 1 ml of triethylamine and 7 ml of DMSO. The mixture is now stirred for 3 hours at 65° and filtered with suction, the filtrate is evaporated and the residue is chromatographed on silica gel (ether/hexane 1:2). This gives 1440 mg of 2-ethoxyimino-6-phenyl-hexa-3,5-diynoic acid methyl ester.

H-5: Preparation of Compound 16.16

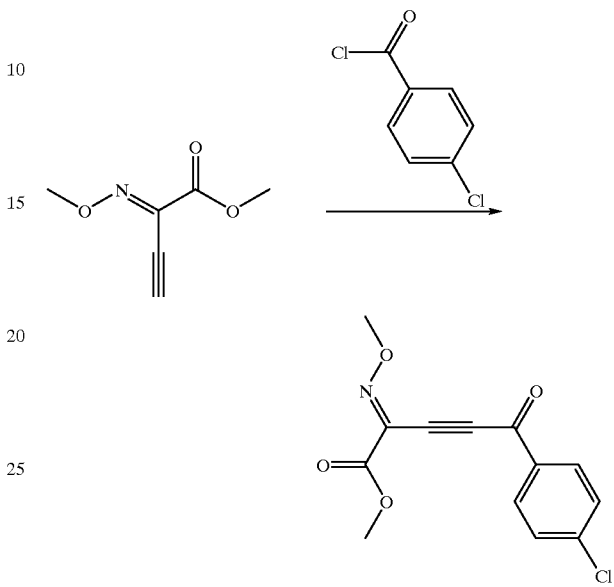

To a solution of 500 mg of 2-methoxyimino-but-3-ynoic acid methyl ester in 10 ml triethylamine and 10 ml toluene 0.1 g of Pd (TPP)2 C12 and 0.7 ml of 4-chlorobenzoylchloride are added.

The mixture is now stirred for 1 hour at 65° and filtered with suction. The precipitate is stirred in water and again filtered with suction. The cristals are stirred with hexane. Filtration gives 840 mg of 5-(4-chloro-phenyl)-2-methoxyimino-5-oxo-pent-3-ynoic acid methyl ester of melting point 172–173°.

H-7: Preparation of Compound 1.16

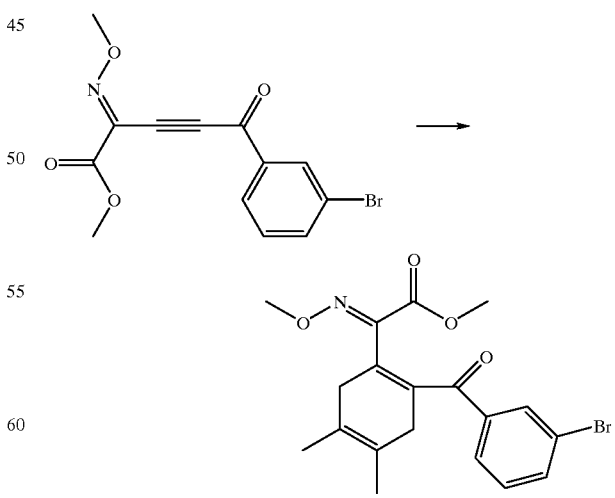

1.5 ml of 2,3-dimethylbuta-1,3-diene are added to the solution of 300 mg 5-(3-bromo-phenyl)-2-methoxyimino-5-oxo-pent-3-ynoic acid methyl ester in 1 ml toluene. The reaction mixture is heated for 24 hours at 130° in an autoclave. It is subsequently evaporated, stirred with petrol ether and filtered with suction. The filtrate is evaporated to give 300 mg of [2-(3- bromo-benzoyl)-4,5-dimethyl-cyclohexa-1,4-dienyl]-methoxyimino-acetic acid methyl ester as a resinous oil.

H-8: Preparation of Compound 3.1

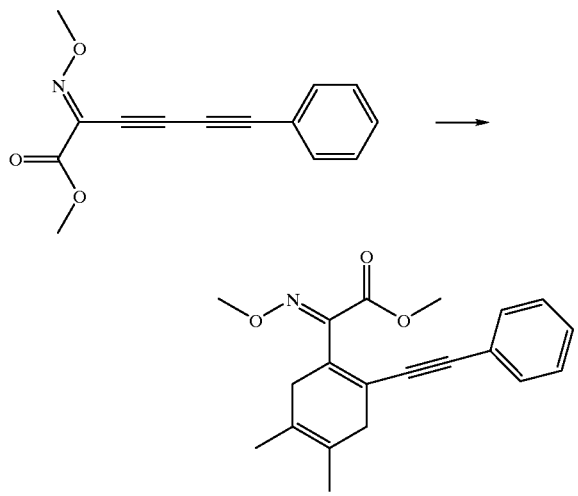

5 ml of 2,3-dimethylbuta-1,3-diene are added to a solution of 1.8 9 of 2-ethoxyimino-6-phenyl-hexa-3,5-diynoic acid methyl ester in 10 ml toluene. The reaction mixture is heated for 24 hours at 140° in an autoclave. It is subsequently evaporated and the residue is chromatographed on silica gel (ethyl acetate/hexane 1:2). This gives 0.8 g of (4,5-dimethyl-2-phenylethynyl-cyclohexa-1,4-dienyl)-methoxyimino-acetic acid methyl ester as a resinous oil.

H-9: Preparation of Compound 16.78

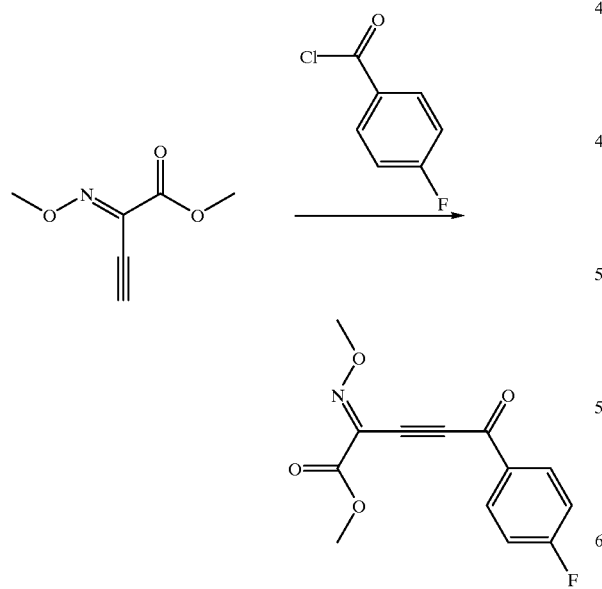

To a solution of 4200 mg of 2-methoxyimino-but-3-ynoic acid methyl ester in 7 ml triethylamine and 120 ml toluene 0.6 g of Pd (TPP)2 Cl2 and 5.5 ml of 4-fluorobenzoylchloride are added. The reaction mixture is added to 300 ml water and extracted three times with 100 ml methylene chloride. The organic phase is dried with magnesium sulfate and filtered. The filtrate is subsequently evaporated and the residue is chromatographed on silica gel (ethyl acetate/hexane 1:19). This gives 6300 mg of 5-(4-chloro-phenyl)-2-methoxyimino-5-oxo-pent-3-ynoic acid methyl.

H-10: Preparation of Compound 1.160

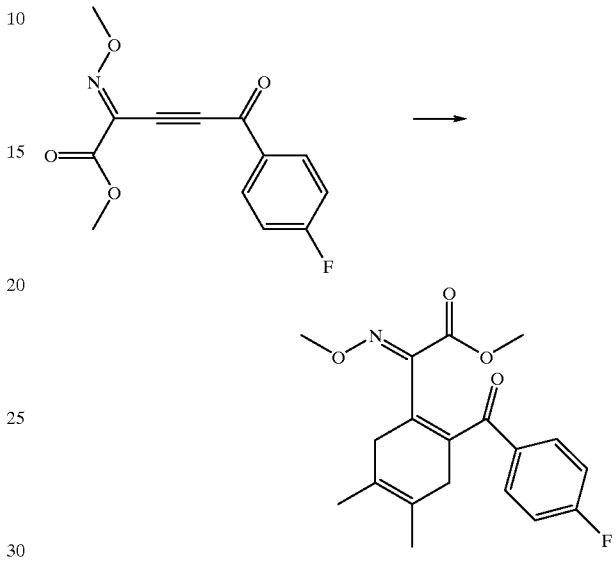

10.5 ml of 2,3-dimethylbuta-1,3-diene are added to the solution of 6000 mg 5-(4-fluoro-phenyl)-2-methoxyimino-5-oxo-pent-3-ynoic acid methyl ester in 10 ml toluene. The reaction mixture is heated for 4 hours at 105° in an autoclave. It is subsequently evaporated, stirred with petrol ether and filtered with suction. The filtrate is subsequently evaporated and the residue is chromatographed on silica gel (ethyl acetate/hexane 1:6). This gives 5300 mg of [2-(4-fluoro-benzoyl)-4,5-dimethyl-cyclohexa-1,4-dienyl]-methoxyimino-acetic acid methyl ester of melting point 97°–98°.

H-11: Preparation of Compound 18a.3

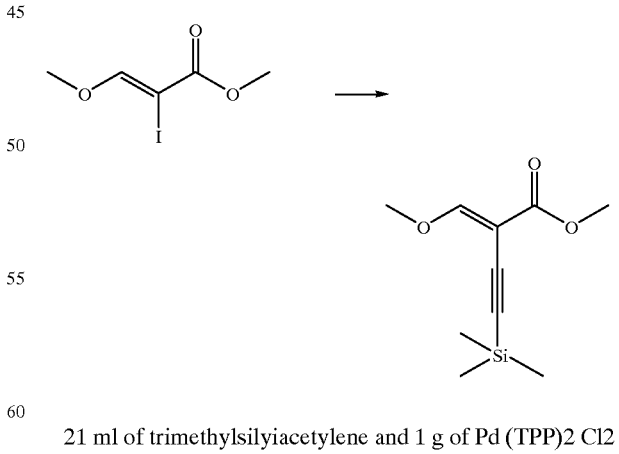

21 ml of trimethylsilyiacetylene and 1 g of Pd (TPP)2 Cl2 and 0.1 g CuI are added to a solution of 35 g of 2-iodo-3-methoxy-acrylic acid methyl ester in 35 ml of triethylamine and 80 ml of DMSO. The mixture is now stirred for 8 hours at 55° and then cooled and chromatographed on silica gel (petroleum ether/t-butylmethylether 3:1). This gives 23.4 g 2-methoxymethylene-4-trimethylsilanyl-but-3-ynoic acid methyl ester of melting point 70°–72°.

H-12: Preparation of Compound 18a.4

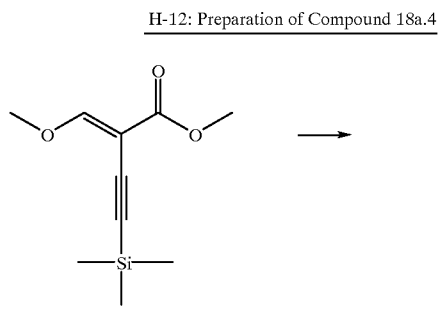 → 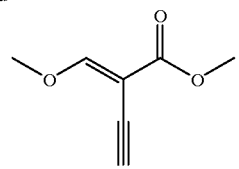

27 g of 2-methoxymethylene-4-trimethylsilanyl-but-3-ynoic acid methyl ester are dissolved in 70 ml dimethylformamide and cooled in an ice bath. 7.8 g of potassium fluoride dissolved in 18 ml water are added. after stirring for 3 hours at room temperature the reaction mixture is poured on 600 ml of water. The precipitate is filtered and dissolved in t-butylmethylether and methylene chloride dried and filtered. The filtrate is evaporated to give 14.75 g of brownish crystals of 2-methoxymethylene-but-3-ynoic acid methyl ester of melting point 89°–91°.

TABLE 1

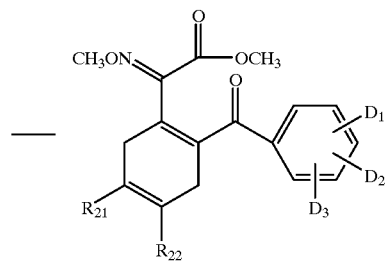

| Comp. No. | $R_{21}$ | $R_{22}$ | $D_1$ | $D_2$ | $D_3$ | Physical data |
|---|---|---|---|---|---|---|
| 1.1 | $CH_3$ | $CH_3$ | H | H | H | |
| 1.2 | $CH_3$ | $CH_3$ | 2-$CH_3$ | H | H | |
| 1.3 | $CH_3$ | $CH_3$ | 3-$CH_3$ | H | H | |
| 1.4 | $CH_3$ | $CH_3$ | 4-$CH_3$ | H | H | |
| 1.5 | $CH_3$ | $CH_3$ | 2-$CH_3$ | 3-$CH_3$ | H | |
| 1.6 | $CH_3$ | $CH_3$ | 2-$CH_3$ | 4-$CH_3$ | H | |
| 1.7 | $CH_3$ | $CH_3$ | 2-$CH_3$ | 5-$CH_3$ | H | |
| 1.8 | $CH_3$ | $CH_3$ | 2-$CH_3$ | 6-$CH_3$ | H | |
| 1.9 | $CH_3$ | $CH_3$ | 2-Et | 4-$CH_3$ | H | |
| 1.10 | $CH_3$ | $CH_3$ | 2-i-Prop | 5-$CH_3$ | H | |
| 1.11 | $CH_3$ | $CH_3$ | 2-$CH_3$ | 6-$CH_3$ | H | |
| 1.12 | $CH_3$ | $CH_3$ | 2-$CH_3$ | 6-$CH_3$ | 4-Me | |
| 1.13 | $CH_3$ | $CH_3$ | 2-$CH_3$ | 6-$CH_3$ | 4-Et | |
| 1.14 | $CH_3$ | $CH_3$ | 2-Cl | H | H | |
| 1.15 | $CH_3$ | $CH_3$ | 3-Cl | H | H | |
| 1.16 | $CH_3$ | $CH_3$ | 4-Cl | H | H | resinous oil |
| 1.17 | $CH_3$ | $CH_3$ | 2-$CH_3$ | 3-Cl | H | |
| 1.18 | $CH_3$ | $CH_3$ | 2-$CH_3$ | 4-Cl | H | |
| 1.19 | $CH_3$ | $CH_3$ | H | 2-$OCH_3$ | H | |
| 1.20 | $CH_3$ | $CH_3$ | H | 3-$OCH_3$ | H | |
| 1.21 | $CH_3$ | $CH_3$ | H | 4-$OCH_3$ | H | |
| 1.22 | $CH_3$ | $CH_3$ | H | 4-$OCF_3$ | H | |
| 1.23 | $CH_3$ | $CH_3$ | 2-$OCH_3$ | 3-$OCH_3$ | H | |
| 1.24 | $CH_3$ | $CH_3$ | 2-$OCH_3$ | 4-$OCH_3$ | H | |
| 1.25 | $CH_3$ | $CH_3$ | 2-$OCH_3$ | 5-$OCH_3$ | H | |
| 1.26 | $CH_3$ | $CH_3$ | 2-$OCH_3$ | 5-$OCH_3$ | 6-OMe | |
| 1.27 | $CH_3$ | $CH_3$ | 2-$OCH_3$ | 5-$OCH_3$ | 4-OMe | |
| 1.28 | $CH_3$ | $CH_3$ | H | 2-$CF_3$ | H | |
| 1.29 | $CH_3$ | $CH_3$ | H | 3-$CF_3$ | H | |
| 1.30 | $CH_3$ | $CH_3$ | H | 4-$CF_3$ | H | |
| 1.31 | $CH_3$ | $CH_3$ | 2-$CH_3$ | 4-$OCF_3$ | H | |
| 1.32 | $H_3$ | $CH_3$ | 2-Et | 3-$CF_3$ | H | |
| 1.33 | $CH_3$ | $CH_3$ | 2-Prop | 4-$CF_3$ | H | |
| 1.34 | $CH_3$ | $CH_3$ | 2-Prop | 4-$CF_3$ | 6-Me | |
| 1.35 | $CH_3$ | $CH_3$ | H | 3-$OCF_3$ | H | |
| 1.36 | $CH_3$ | $CH_3$ | H | 5-$OCF_3$ | H | |
| 1.37 | $CH_3$ | $CH_3$ | H | 5-$OCF_3$ | 2-Me | |
| 1.38 | $CH_3$ | $CH_3$ | H | 5-$OCF_3$ | 4-Me | |
| 1.39 | $CH_3$ | $CH_3$ | 2-$CH_3$ | 4-propynyl | H | |

TABLE 1-continued

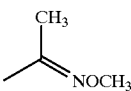

| Comp. No. | $R_{21}$ | $R_{22}$ | $D_1$ | $D_2$ | $D_3$ | Physical data |
|---|---|---|---|---|---|---|
| 1.40 | $CH_3$ | $CH_3$ | 2-$CH_3$ | 4-allyl | H | |
| 1.41 | $CH_3$ | $CH_3$ | 3-$CH_3$ | 6-propargyl | H | |
| 1.42 | $CH_3$ | $CH_3$ | 2-$OCH_3$ | 4-allyl | H | |
| 1.43 | $CH_3$ | $CH_3$ | 2-$OCH_3$ | 4-propargyl | H | |
| 1.44 | $CH_3$ | $CH_3$ | 2-$CH_3$ | 4-O-allyl | H | |
| 1.45 | $CH_3$ | $CH_3$ | 2-$CH_3$ | 4-O-propargyl | H | |
| 1.46 | $CH_3$ | $CH_3$ | 2-$OCH_3$ | 4-O-allyl | H | |
| 1.47 | $CH_3$ | $CH_3$ | 2-$OCH_3$ | 4-O-propargyl | H | |
| 1.48 | $CH_3$ | $CH_3$ | 2-$OCH_3$ | 4-ethynyl | H | |
| 1.49 | $CH_3$ | $CH_3$ | 2-$OCH_3$ | 4-ethynyl | 6-Me | |
| 1.50 | $CH_3$ | $CH_3$ | 2-O-allyl | 4-O-allyl | H | |
| 1.51 | $CH_3$ | $CH_3$ | 2-O-allyl | 6-O-propargyl | H | |
| 1.52 | $CH_3$ | $CH_3$ | 2-Cl | 4-O-allyl | H | |
| 1.53 | $CH_3$ | $CH_3$ | 2-Br | 4-O-propargyl | H | |
| 1.54 | $CH_3$ | $CH_3$ | 2-$CF_3$ | 4-ethynyl | H | |
| 1.55 | $CH_3$ | $CH_3$ | 2-$CF_3$ | 4-ethynyl | 6-Me | |
| 1.56 | $CH_3$ | $CH_3$ | H | 2-benzyl | H | |
| 1.57 | $CH_3$ | $CH_3$ | H | 2-benzyloxy | H | |
| 1.58 | $CH_3$ | $CH_3$ | 2-$CH_3$ | 3-phenoxy | H | |
| 1.59 | $CH_3$ | $CH_3$ | 2-$CH_3$ | 3-phenoxy(4-Cl) | H | |
| 1.60 | $CH_3$ | $CH_3$ | 2-$OCH_3$ | 4-benzyloxy | H | |
| 1.61 | $CH_3$ | $CH_3$ | 3-$OCH_3$ | 5-benzyloxy(3-$CF_3$) | H | |
| 1.62 | $CH_3$ | $CH_3$ | 3-$OCH_3$ | 6-benzyloxy(3-$OCF_3$) | H | |
| 1.63 | $CH_3$ | $CH_3$ | H | 4-cyclopropylmethyloxy | H | |
| 1.64 | $CH_3$ | $CH_3$ | 3-$OCH_3$ | 5-cyclopropylmethyloxy | H | |
| 1.65 | $CH_3$ | $CH_3$ | 3-$OCH_3$ | 5-(dichloro-cyclopropyl)-methoxy | H | |
| 1.66 | $CH_3$ | $CH_3$ | H | 3- 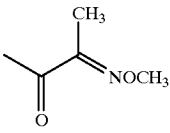 | H | |
| 1.67 | $CH_3$ | $CH_3$ | H | 4- 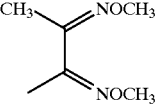 | H | |
| 1.68 | $CH_3$ | $CH_3$ | H | 4- 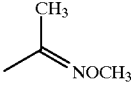 | H | |
| 1.69 | $CH_3$ | $CH_3$ | H | 3- 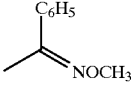 | H | |
| 1.70 | $CH_3$ | $CH_3$ | H | 3- $C_6H_5$ 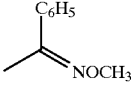 | H | |
| 1.71 | $CH_3$ | $CH_3$ | H | 4- $C_6H_5$-4-Cl 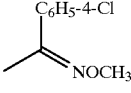 | H | |

TABLE 1-continued

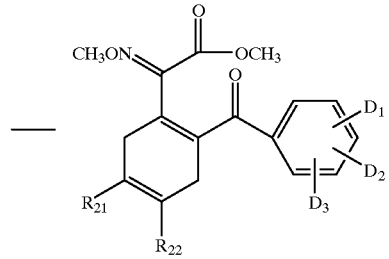

| Comp. No. | $R_{21}$ | $R_{22}$ | $D_1$ | $D_2$ | $D_3$ | Physical data |
|---|---|---|---|---|---|---|
| 1.72 | CH$_3$ | CH$_3$ | H | 4-C$_6$H$_4$-4-phenoxy (=NOCH$_3$) | | |
| 1.73 | CH$_3$ | CH$_3$ | H | 4-C$_6$H$_4$-4-(4-chlorophenoxy) (=NOCH$_3$) | H | |
| 1.74 | CH$_3$ | CH$_3$ | H | 4-C$_6$H$_4$-4-(4-chlorophenoxy) (=NOC$_2$H$_5$) | H | |
| 1.75 | H | CH$_3$ | 3-CH$_3$ | H | H | |
| 1.76 | H | CH$_3$ | 4-CH$_3$ | H | H | |
| 1.77 | H | CH$_3$ | 2-CH$_3$ | 3-CH$_3$ | H | |
| 1.78 | H | CH$_3$ | 2-CH$_3$ | 4-CH$_3$ | H | |
| 1.79 | CH$_3$ | H | 2-CH$_3$ | 5-CH$_3$ | H | |
| 1.80 | CH$_3$ | H | 2-CH$_3$ | 6-CH$_3$ | H | |
| 1.81 | CH$_3$ | H | 2-Et | 4-CH$_3$ | H | |
| 1.82 | CH$_3$ | H | 2-i-Prop | 5-CH$_3$ | H | |
| 1.83 | CH$_3$ | H | 2-i-Prop | 5-CH$_3$ | 4-Me | |
| 1.84 | H | Cl | 2-CH$_3$ | 6-CH$_3$ | H | |
| 1.85 | H | Cl | 2-Cl | H | H | |
| 1.86 | H | Cl | 3-Cl | H | H | |
| 1.87 | H | Cl | 4-Cl | H | H | |
| 1.88 | H | Cl | 4-Cl | H | 4-Me | |
| 1.89 | OCH$_3$ | H | 2-CH$_3$ | 3-Cl | H | |
| 1.90 | OCH$_3$ | H | 2-CH$_3$ | 4-Cl | H | |
| 1.91 | OCH$_3$ | H | H | 2-OCH$_3$ | H | |
| 1.92 | OCH$_3$ | CH$_3$ | H | 3-OCH$_3$ | H | |
| 1.93 | OCH$_3$ | CH$_3$ | H | 4-OCH$_3$ | H | |
| 1.94 | OCH$_3$ | CH$_3$ | H | 5-OCH$_3$ | H | |
| 1.95 | OCH$_3$ | CH$_3$ | H | 5-OCH$_3$ | 4-OMe | |
| 1.96 | CH$_3$ | CH$_3$ | 2-OCH$_3$ | 3-OCH$_3$ | H | |
| 1.97 | CH$_3$ | CH$_3$ | 2-OCH$_3$ | 4-OCH$_3$ | H | |
| 1.98 | CH$_3$ | CH$_3$ | 2-OCH$_3$ | 5-OCH$_3$ | H | |
| 1.99 | CH$_3$ | CH$_3$ | H | 2-CF$_3$ | H | |
| 1.100 | Cl | CH$_3$ | H | 3-CF$_3$ | H | |
| 1.101 | CH$_3$ | CH$_3$ | H | 4-CF$_3$ | H | |
| 1.102 | CH$_3$ | CH$_3$ | 2-CH$_3$ | 4-OCF$_3$ | H | |
| 1.103 | H | H | 2-CH$_3$ | 4-OCF$_3$ | H | |
| 1.104 | H | H | 2-Et | 3-CF$_3$ | H | |
| 1.105 | H | H | 2-Prop | 4-CF$_3$ | H | |
| 1.106 | H | H | H | 4-OCF$_3$ | H | |
| 1.107 | H | H | H | 3-OCF$_3$ | H | |
| 1.108 | H | H | H | 5-OCF$_3$ | H | |
| 1.109 | H | H | H | 4-ethynyl | H | |
| 1.110 | Cl | CH$_3$ | 2-CH$_3$ | 4-propynyl | H | |
| 1.111 | Cl | CH$_3$ | 2-CH$_3$ | 4-allyl | H | |
| 1.112 | Cl | CH$_3$ | 3-CH$_3$ | 6-propargyl | H | |
| 1.113 | CH$_3$ | Cl | 2-OCH$_3$ | 4-allyl | H | |
| 1.114 | CH$_3$ | Cl | 2-OCH$_3$ | 4-propargyl | H | |
| 1.115 | CH$_3$ | Cl | 3-OCH$_3$ | 4-propargyl | H | |

TABLE 1-continued
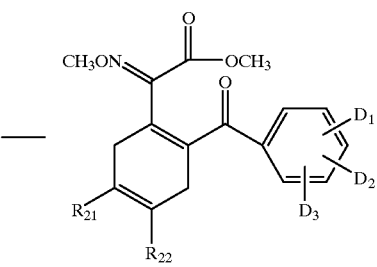
| Comp. No. | R21 | R22 | D1 | D2 | | D3 | Physical data |
|---|---|---|---|---|---|---|---|
| 1.116 | CH3 | CH3 | H | 3- | CH3-C(=NOCH3)- | H | |
| 1.117 | H | H | H | 4- | CH3-C(=NOCH3)-C(=O)- | H | |
| 1.118 | H | H | H | 4- | CH3-C(=NOCH3)-C(=NOCH3)- | H | |
| 1.119 | CH3 | H | H | 3- | CH3-C(=NOCH3)- | H | |
| 1.120 | Cl | CH3 | H | 3- | C6H5-C(=NOCH3)- | H | |
| 1.121 | Cl | CH3 | H | 4- | C6H5-4-Cl-C(=NOCH3)- | H | |
| 1.122 | CH3 | Cl | H | 4- | C6H4-4-phenoxy-C(=NOCH3)- | H | |
| 1.123 | CH3 | Cl | H | 4- | C6H4-4-(4-chlorophenoxy)-C(=NOCH3)- | H | |
| 1.124 | Me | Me | H | 4- | C6H4-4-OCH2-C6H4-3-CF3-C(=NOC2H5)- | H | |
| 1.125 | Me | Me | H | 4- | C6H4-4-OCH2-C6H4-4-CF3-C(=NOC2H5)- | H | |

TABLE 1-continued

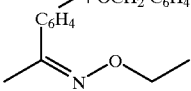

| Comp. No. | R21 | R22 | D1 | D2 | D3 | Physical data |
|---|---|---|---|---|---|---|
| 1.126 | Me | Me | H | 4-C6H4-C(=NOEt)-4-OCH2-C6H4-2-CF3 | H | |
| 1.127 | Me | Me | 2-CH=CH2 | 3-CH=CH— | H | |
| 1.128 | Me | Me | 2-Me | 3-CH2—CH=CH2 | 4-OMe | |
| 1.129 | Me | Me | 2-Me | 3-CH2—CH=CH2 | 4-OEt | |
| 1.130 | Me | Me | 2-Me | 4-OCH2—C6H5 | 3-CH2—CH=CH2 | |
| 1.131 | Me | Me | 2-Me | 4-OCH2—C6H4(4-CN) | 3-CH2—CH=CH2 | |
| 1.132 | H | H | 2-Me | 3-CH2—CH=CH2 | 4-OMe | |
| 1.133 | H | H | 2-Me | 3-CH2—CH=CH2 | 4-OEt | |
| 1.134 | H | H | 2-Me | 4-OCH2—C6H5 | 3-CH2—CH=CH2 | |
| 1.135 | H | H | 2-Me | 4-OCH2—C6H4(4-CN) | 3-CH2—CH=CH2 | |
| 1.136 | H | H | 3-Me | 4-ethynyl | 2-Me | |
| 1.137 | H | H | 3-Me | 4-OCH2—CH2—OH | 2-Me | |
| 1.138 | H | H | 3-Me | 4-OCH2—CH2—OCOCH3 | 2-Me | |
| 1.139 | H | H | 3-Me | 4-OCH2—CH2—OCO(CH3)6—CH=CF2 | 2-Me | |
| 1.140 | H | Me | H | 2-Me | H | |
| 1.141 | Me | Me | H | 4-C(Me)2—C6H4-4'-OCH2—C≡C—C6H3(Cl2)(2",4") | H | |
| 1.142 | Me | Me | H | —O—(CH2)3—C6H5 | H | |
| 1.143 | Me | Me | H | 2-Me | H | |
| 1.144 | Me | Me | H | —(C=NOEt)C6H5(F)(4') | H | |
| 1.145 | Me | Me | H | —(C=NOEt)C6H4(Br)(4') | H | |
| 1.146 | Me | Me | H | —(C=NOEt)C6H4—(C≡C—C6H5)(4') | H | |
| 1.147 | Me | Me | H | —(C=NOEt)C6H4—(CH2—CH2—C6H5)(4') | H | |
| 1.148 | Me | Me | H | 3-O-propargyl | H | |
| 1.149 | Me | Me | 2-Br | 4-Cl | H | |
| 1.150 | Me | Me | 4-Br | 2-Cl | H | |
| 1.151 | Me | Me | H | 4-COEt | H | |
| 1.152 | Me | Me | H | 4-COMe | H | |
| 1.153 | Me | Me | H | 3-CH2—(3'-methylisoxazolyl(5')) | H | |
| 1.154 | Me | Me | H | 3-CH2—(3'-ethylisoxazolyl(5')) | H | |
| 1.155 | Me | Me | H | 4-I | H | |
| 1.156 | Me | Me | H | 3-I | H | |
| 1.157 | Me | Me | H | 4-C9H19 | H | |
| 1.158 | Me | Me | H | 4-NO2 | H | |
| 1.159 | Me | Me | H | 4-Br | H | resinous oil |
| 1.160 | Me | Me | H | 4-F | H | 97–98 |
| 1.161 | Me | Me | H | 4-C12H25 | H | |
| 1.162 | Me | Me | H | 4-OCH2CH2O—CO(CH2)3—CH=C(F2) | H | |
| 1.163 | Me | Me | H | 4-naphthyl(1') | H | |
| 1.164 | Me | Me | H | 4-naphthyl(2') | H | |
| 1.165 | Me | Me | 2-Cl | 4-C6H5 | H | |
| 1.166 | Me | Me | H | 4-S(O)C6H5 | H | |
| 1.167 | Me | Me | H | 4-(2'-pyridyl(F)(3')(Cl)(5')) | H | |
| 1.168 | Me | Me | H | 4-C6H5 | H | |
| 1.169 | Me | Me | H | 3-O-allyl | H | |
| 1.170 | Me | Me | H | 3-C≡CH | H | |
| 1.171 | Me | Me | H | 4-CO—C6H4(4')-C6H4(Cl)(4") | H | |
| 1.172 | Me | Me | H | 4-i-prop | H | |
| 1.173 | Me | Me | 2-F | 4-F | H | |
| 1.174 | Me | Me | H | 3-F | H | |
| 1.175 | Me | Me | H | 2-F | H | |
| 1.176 | Me | Me | H | 4-O-propargyl | H | |
| 1.177 | Me | Me | H | 4-NH2 | H | |
| 1.178 | Me | Me | H | 3-OH | H | |
| 1.179 | Me | Me | H | 4-OH | H | |
| 1.180 | Me | Me | H | 2-CH3 | H | |

TABLE 2

Compounds of the formula

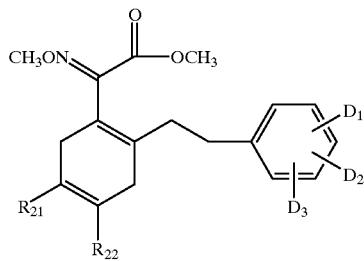

in which $R_{21}$, $R_{22}$, $D_1$, $D_2$ and $D_3$ have the meanings of the corresponding compounds of Table 1.

TABLE 3

Compounds of the formula

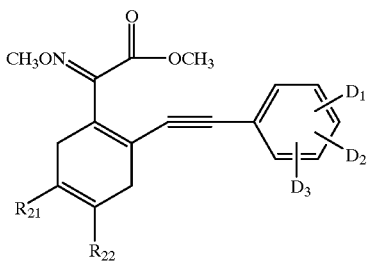

in which $R_{21}$, $R_{22}$, $D_1$, $D_2$ and $D_3$ have the meanings of the corresponding compounds of Table 1.

TABLE 4

Compounds of the formula

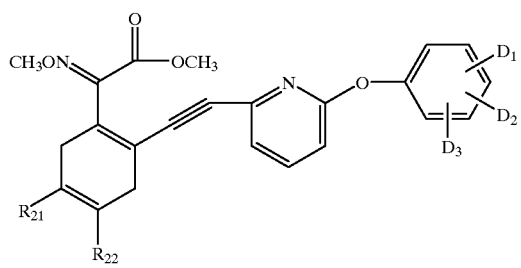

in which $R_{21}$, $R_{22}$, $D_1$, $D_2$ and $D_3$ have the meanings of the corresponding compounds of Table 1.

TABLE 5

Compounds of the formula

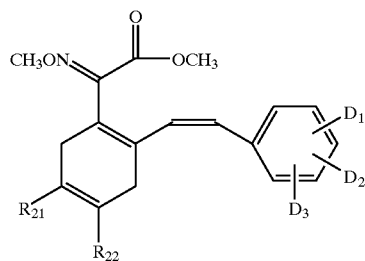

in which $R_2$, $R_{22}$, $D_1$, $D_2$ and $D_3$ have the meanings of the corresponding compounds of Table 1.

TABLE 6

Compounds of the formula

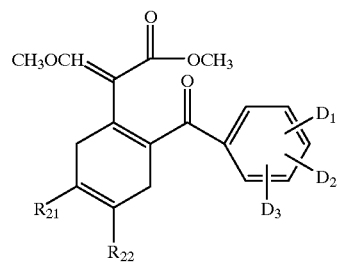

in which $R_{21}$, $R_{22}$, $R_8$, $R_9$, $D_1$, $D_2$ und $D_3$ have the meanings of the corresponding compounds of Table 1.

TABLE 7

Compounds of the formula

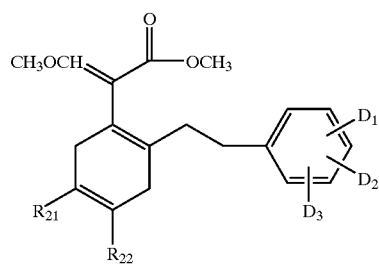

in which $R_{21}$, $R_{22}$, $D_1$, $D_2$ and $D_3$ have the meanings of the corresponding compounds of Table 1.

TABLE 8

Compounds of the formula

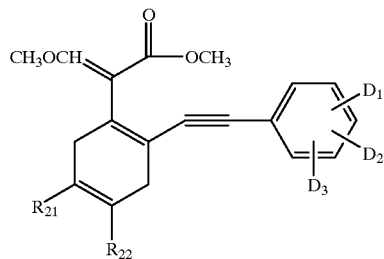

in which $R_{21}$, $R_{22}$, $D_1$, $D_2$ and $D_3$ have the meanings of the corresponding compounds of Table 1.

TABLE 9

Compounds of the formula

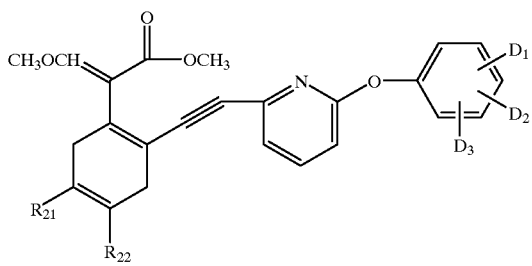

in which $R_{21}$, $R_{22}$, $D_1$, $D_2$ and $D_3$ have the meanings of the corresponding compounds of Table 1.

TABLE 10

Compounds of the formula

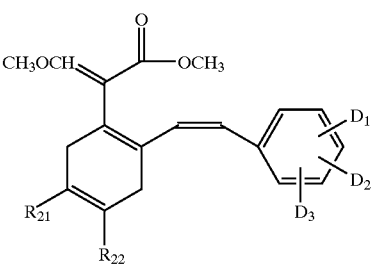

in which $R_{21}$, $R_{22}$, $D_1$, $D_2$ and $D_3$ have the meanings of the corresponding compounds of Table 1.

TABLE 11

Compounds of the formula

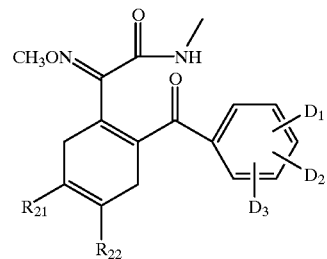

in which $R_{21}$, $R_{22}$, $R_8$, $R_9$, $D_1$, $D_2$ and $D_3$ have the meanings of the corresponding compounds of Table 1.

TABLE 12

Compounds of the formula

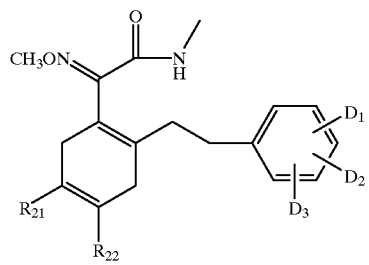

in which $R_{21}$, $R_{22}$, $R_8$, $R_9$, $D_1$, $D_2$ and $D_3$ have the meanings of the corresponding compounds of Table 1.

TABLE 13

Compounds of the formula

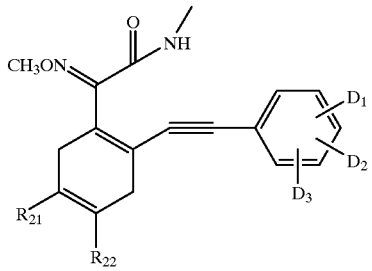

in which $R_{21}$, $R_{22}$, $D_1$, $D_2$ and $D_3$ have the meanings of the corresponding compounds of Table 1.

TABLE 14

Compounds of the formula

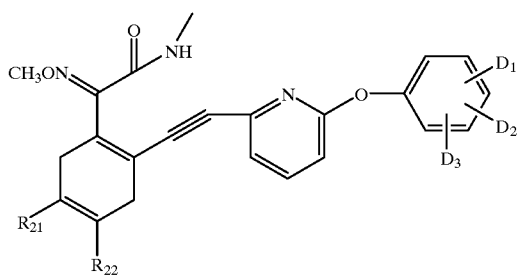

in which $R_{21}$, $R_{22}$, $D_1$, $D_2$ and $D_3$ have the meanings of the corresponding compounds of Table 1.

TABLE 15

Compounds of the formula

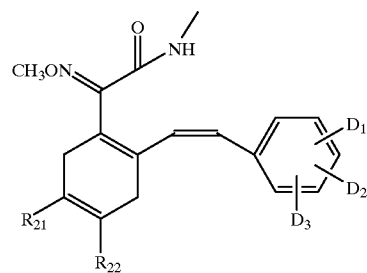

in which $R_{21}$, $R_{22}$, $D_1$, $D_2$ and $D_3$ have the meanings of the corresponding compounds of Table 1.

TABLE 16

(intermediates)

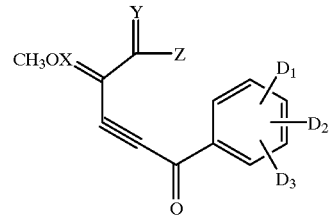

| Comp. No. | X | Y | Z | $D_1$ | $D_2$ | $D_3$ | Physical data; m.p. |
|---|---|---|---|---|---|---|---|
| 16.1. | CH | O | OCH$_3$ | H | H | H | |
| 16.2. | CH | O | OCH$_3$ | 2-CH$_3$ | H | H | |
| 16.3. | CH | O | OCH$_3$ | 3-CH$_3$ | H | H | |
| 16.4. | N | O | OCH$_3$ | 2-CH$_3$ | H | H | |
| 16.5. | N | O | OCH$_3$ | 2-CH$_3$ | 3-CH$_3$ | H | |
| 16.6. | N | O | OCH$_3$ | 2-CH$_3$ | 4-CH$_3$ | H | |
| 16.7. | CH | O | OCH$_3$ | 2-CH$_3$ | 5-CH$_3$ | H | |
| 16.8. | N | O | NHCH$_3$ | 2-CH$_3$ | 6-CH$_3$ | H | |
| 16.9. | N | S | NHCH$_3$ | 2-Et | 4-CH$_3$ | H | |
| 16.10. | N | S | NHCH$_3$ | 2-i-Prop | 5-CH$_3$ | H | |
| 16.11. | N | S | SCH$_3$ | 2-CH$_3$ | 6-CH$_3$ | H | |
| 16.12. | N | SO | SCH$_3$ | 2-CH$_3$ | 6-CH$_3$ | 4-Me | |
| 16.13. | N | SO | SCH$_3$ | 2-CH$_3$ | 6-CH$_3$ | 4-Et | |
| 16.14. | CH | O | SCH$_3$ | 2-Cl | H | H | |
| 16.15. | CH | O | SCH$_3$ | 3-Cl | H | H | |
| 16.16. | N | O | OCH$_3$ | 4-Cl | H | H | resin |
| 16.17. | N | O | NHCH$_3$ | 2-CH$_3$ | 3-Cl | H | |
| 16.18. | N | O | NHCH$_3$ | 2-CH$_3$ | 4-Cl | H | |
| 16.19. | N | S | NHCH$_3$ | H | 2-OCH$_3$ | H | |
| 16.20. | N | O | NHCH$_3$ | H | 3-OCH$_3$ | H | |
| 16.21. | N | S | SCH$_3$ | H | 4-OCH$_3$ | H | |
| 16.22. | N | S | SCH$_3$ | H | 4-OCF$_3$ | H | |
| 16.23. | N | O | OCH$_3$ | 2-OCH$_3$ | 3-OCH$_3$ | H | |
| 16.24. | CH | O | OCH$_3$ | 2-OCH$_3$ | 4-OCH$_3$ | H | |
| 16.25. | CH | O | OCH$_3$ | 2-OCH$_3$ | 5-OCH$_3$ | H | |
| 16.26. | CH | O | OCH$_3$ | 2-OCH$_3$ | 5-OCH$_3$ | 6-OMe | |
| 16.27. | N | O | OCH$_3$ | 2-OCH$_3$ | 5-OCH$_3$ | 4-OMe | |
| 16.28. | N | O | OCH$_3$ | H | 2-CF$_3$ | H | |
| 16.29. | N | O | OCH$_3$ | H | 3-CF$_3$ | H | |
| 16.30. | CH | O | OCH$_3$ | H | 4-CF$_3$ | H | |
| 16.31. | N | O | NHCH$_3$ | 2-CH$_3$ | 4-OCF$_3$ | H | |
| 16.32. | N | S | NHCH$_3$ | 2-Et | 3-CF$_3$ | H | |
| 16.33. | N | S | NHCH$_3$ | 2-prop | 4-CF$_3$ | H | |
| 16.34. | N | S | SCH$_3$ | 2-prop | 4-CF$_3$ | 6-Me | |
| 16.35. | N | SO | SCH$_3$ | H | 3-OCF$_3$ | H | |
| 16.36. | N | SO | SCH$_3$ | H | 5-OCF$_3$ | H | |
| 16.37. | CH | O | SCH$_3$ | H | 5-OCF$_3$ | 2-Me | |

TABLE 16-continued (intermediates)

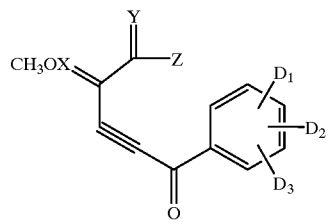

| Comp. No. | X | Y | Z | D₁ | D₂ | D₃ | Physical data; m.p. |
|---|---|---|---|---|---|---|---|
| 16.38. | CH | O | SCH₃ | H | 5-OCF₃ | 4-Me | |
| 16.39. | N | O | OCH₃ | 2-CH₃ | 4-propynyl | H | |
| 16.40. | N | O | NHCH₃ | 2-CH₃ | 4-allyl | H | |
| 16.41. | N | O | NHCH₃ | 3-CH₃ | 6-propargyl | H | |
| 16.42. | N | S | NHCH₃ | 2-OCH₃ | 4-allyl | H | |
| 16.43. | N | O | NHCH₃ | 2-OCH₃ | 4-propargyl | H | |
| 16.44. | N | S | SCH₃ | 2-CH₃ | 4-O-allyl | H | |
| 16.45. | N | S | SCH₃ | 2-CH₃ | 4-O-propargyl | H | |
| 16.46. | N | O | OCH₃ | 2-OCH₃ | 4-O-allyl | H | |
| 16.47. | CH | O | OCH₃ | 2-OCH₃ | 4-O-propargyl | H | |
| 16.48. | CH | O | OCH₃ | 2-OCH₃ | 4-ethynyl | H | |
| 16.49. | CH | O | OCH₃ | 2-OCH₃ | 4-ethynyl | 6-Me | |
| 16.50. | N | O | OCH₃ | 2-O-allyl | 4-O-allyl | H | |
| 16.51. | N | O | OCH₃ | 2-O-allyl | 6-O-propargyl | H | |
| 16.52. | N | O | OCH₃ | 2-Cl | 4-O-allyl | H | |
| 16.53. | CH | O | OCH₃ | 2-Br | 4-O-propargyl | H | |
| 16.54. | N | O | NHCH₃ | 2-CF₃ | 4-ethynyl | H | |
| 16.55. | N | S | NHCH₃ | 2-CF₃ | 4-ethynyl | 6-Me | |
| 16.56. | N | S | NHCH₃ | H | 2-benzyl | H | |
| 16.57. | N | S | SCH₃ | H | 2-benzyloxy | H | |
| 16.58. | N | SO | SCH₃ | 2-CH₃ | 3-phenoxy | H | |
| 16.59. | N | SO | SCH₃ | 2-CH₃ | 3-phenoxy(4-Cl) | H | |
| 16.60. | CH | O | SCH₃ | 2-OCH₃ | 4-benzyloxy | H | |
| 16.61. | CH | O | SCH₃ | 3-OCH₃ | 5-benzyloxy(3-CF₃) | H | |
| 16.62. | N | O | OCH₃ | 3-OCH₃ | 6-benzyloxy(3-OCF₃) | H | |
| 16.63. | N | O | NHCH₃ | H | 4-cyclopropylmethyloxy | H | |
| 16.64. | N | O | NHCH₃ | 3-OCH₃ | 5-cyclopropylmethyloxy | H | |
| 16.65. | N | S | NHCH₃ | 3-OCH₃ | 5-(dichlorocyclopropyl)methoxy | H | |
| 16.66. | N | O | NHCH₃ | H | 3- -) | H | |
| 16.67. | N | S | SCH₃ | H | 4- -C(CH₃)=NOCH₃) | H | |
| 16.68. | N | S | SCH₃ | H | 4- -C(CH₃)=NOCH₃) | H | |
| 16.69. | N | O | OCH₃ | H | 3- -) | H | |
| 16.70. | CH | O | OCH₃ | H | 3- -) | H | |
| 16.71. | CH | O | OCH₃ | H | 4- -) | H | |

TABLE 16-continued (intermediates)

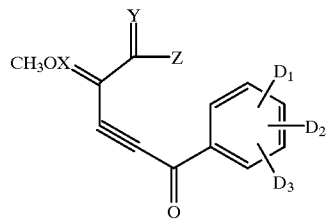

| Comp. No. | X | Y | Z | $D_1$ | $D_2$ | $D_3$ | Physical data; m.p. |
|---|---|---|---|---|---|---|---|
| 16.72. | CH | O | $OCH_3$ | H | 4-$C_6H_4$-4-phenoxy, =NOCH$_3$ | | |
| 16.73. | N | O | $OCH_3$ | H | 4-$C_6H_4$-4-(4-chlorophenoxy), =NOCH$_3$ | H | |
| 16.74. | N | O | $OCH_3$ | H | 4-$C_6H_4$-4-(4-chlorophenoxy), =NOC$_2$H$_5$ | H | |
| 16.75. | CH | S | $OCH_3$ | | 4-$C_6H_4$-4-OCH$_2$-C$_6$H$_4$-3-CF$_3$, =N-O-ethyl | H | |
| 16.76. | N | O | $OCH_3$ | | 4-$C_6H_4$-4-OCH$_2$-C$_6$H$_4$-4-CF$_3$, =N-O-ethyl | H | |
| 16.77. | N | SO | $OCH_3$ | | 4-$C_6H_4$-4-OCH$_2$-C$_6$H$_4$-2-CF$_3$, =N-O-ethyl | H | |
| 16.78. | CH | O | $OCH_3$ | 4-F | | H | 138–140 |
| 16.79. | CH | O | $OCH_3$ | 3-Br | | H | 72–76 |

TABLE 17

(intermediates)
Compounds of the formula

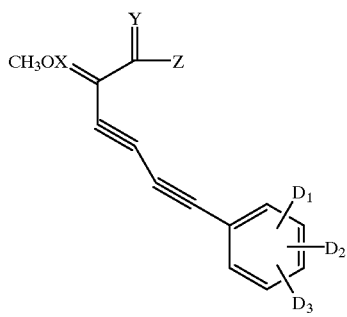

in which X, Y, Z, $D_1$, $D_2$ and $D_3$ have the meanings of the corresponding compounds of Table 16.

TABLE 18

(intermediates)
Compounds of the formula

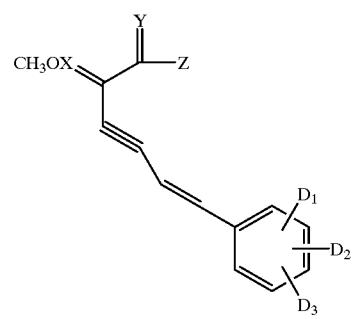

in which X, Y, Z, $D_1$, $D_2$ and $D_3$ have the meanings of the corresponding compounds of Table 1.

TABLE 18a

[Structure: CH3OX-C(=Y)(Z) connected to C≡C-QQ]

| Comp. No. | X | Y | Z | QQ | Physical data |
|---|---|---|---|---|---|
| 18a.1. | N | O | OCH₃ | H | 82–83° |
| 18a.2. | N | O | OCH₃ | SiMe₃ | resin |
| 18a.3. | CH | O | OCH₃ | SiMe₃ | dark oil |
| 18a.4. | CH | O | OCH₃ | H | 89–91 |

TABLE 19

[Structure: CH₃ON=C(-C(=O)Z)-cyclohexadiene with two CH₃ substituents and -CH₂CH₂W group]

| Comp. No. | Z | W | Physical data m.p. |
|---|---|---|---|
| 19.01. | OMe | 3-C₆H₄—C≡C—C₆H₃Cl₂(2',4') | |
| 19.02. | OMe | 3-C₆H₄—C≡C—C₆H₅ | |
| 19.03. | OMe | 3-C₆H₄—C≡C—C₆H₄(OCH₃)(4') | |
| 19.04. | OMe | 3-C₆H₄—C≡C—C₆H₃(CF₃)(3',5') | |
| 19.05. | OMe | 3-C₆H₄—C≡C—C₆H₄(CF₃)(3') | |
| 19.06. | OMe | 3-C₆H₄—C≡C—CO—C₆H₄(CF₃)(3') | |
| 19.07. | OMe | 3-C₆H₄—C≡C—CO—C₆H₅ | |
| 19.08. | OMe | 3-C₆H₄—C≡C—CO—C₆H₄(Cl)(3') | |
| 19.09. | OMe | 3-C₆H₄—C≡C—C₃H₇(i) | |
| 19.10. | OMe | 3-C₆H₄—C≡C—C≡C—C(CH₃)₂—OH | |
| 19.11. | OMe | 3-C₆H₄—(C≡C)₂—C(CH₃)₂—OCOCH₃ | |
| 19.12. | OMe | 3-C₆H₄—C≡C—C(CH₃)₂—OH | |
| 19.13. | OMe | 3-C₆H₄—C≡C-pyrazinyl(2') | |
| 19.14. | OMe | 3-C₆H₄—C≡C-pyridyl(3') | |
| 19.15. | OMe | 3-C₆H₄—C≡C—CO-pyridyl(3') | |
| 19.16. | OMe | 3-C₆H₄—C≡C-pyridyl(2') | |
| 19.17. | OMe | 3-C₆H₄—C≡C-pyridyl(4') | |
| 19.18. | OMe | 3-C₆H₄—C≡C—C₆H₄(CF₃)(4') | |
| 19.19. | OMe | 3-C₆H₄—C≡C—C₆H₄(Cl)(4') | |
| 19.20. | OMe | 3-C₆H₄—C≡C—CH₂—OH | |
| 19.21. | OMe | 3-C₆H₄—C≡C-pyrimidinyl(2') | |
| 19.22. | OMe | 3-C₆H₄—C≡C-pyrimidinyl(4') | |
| 19.23. | OMe | 3-C₆H₄—C≡C-pyrimidinyl(5') | |
| 19.24. | OMe | 3-C₆H₄—C≡C—I | |
| 19.25. | OMe | 3-C₆H₄—C≡C—CH₃ | |
| 19.26. | OMe | 3-C₆H₄—C≡C—Br | |
| 19.27. | OMe | 3-C₆H₄—C≡C—C₆H₄(Br)(4') | |
| 19.28. | OMe | 3-C₆H₄—C≡C—C₆H₃(OCH₃)₃(3',4',5') | |
| 19.29. | OMe | 3-C₆H₄—C≡C—C₆H₃(CH₃)₂(3',5') | |
| 19.30. | OMe | 3-C₆H₄—C≡C-thiazolyl(2') | |
| 19.31. | OMe | 3-C₆H₄—C≡C-oxazolyl(2') | |
| 19.32. | OMe | 3-C₆H₄—C≡C-thienyl(2') | |
| 19.33. | OMe | 3-C₆H₄—C≡C-thienyl(3') | |
| 19.34. | OMe | 3-C₆H₄—C≡C—Et | |
| 19.35. | OMe | 4-C₆H₄—C≡C—H | |
| 19.36. | OMe | 2-C₆H₄—C≡C—H | |

TABLE 19-continued

[Structure: dimethylcyclohexadiene with CH3ON=C(C(=O)-Z) group and CH2CH2-W substituent]

| Comp. No. | Z | W | Physical data m.p. |
|---|---|---|---|
| 19.37. | OMe | 4-C$_6$H$_4$—C≡C—CH$_3$ | |
| 19.38. | OMe | 2-C$_6$H$_4$—C≡C—Br | |
| 19.39. | OMe | 2-C$_6$H$_4$—C≡C—C(CH$_3$)$_2$—OH | |
| 19.40. | OMe | 4-C$_6$H$_4$—C≡C—C(CH$_3$)$_2$—OH | |
| 19.41. | OMe | 3-C$_6$H$_4$—C≡C—CF$_3$ | |
| 19.42. | OMe | 3-C$_6$H$_4$—C≡C—COOEt | |
| 19.43. | OMe | 3-C$_6$H$_4$—C≡C—COOMe | |
| 19.44. | OMe | 2-C$_6$H$_4$—C≡C—C(CH$_3$)$_2$—OH | |
| 19.45. | OMe | 3-C$_6$H$_4$—C≡C—C(CH$_3$)$_2$—O—CH$_3$ | |
| 19.46. | OMe | 4-C$_6$H$_4$—C≡C—C(CH$_3$)$_2$—O—CH$_3$ | |
| 19.47. | OMe | 3-C$_6$H$_4$—C≡C—CH$_2$—OMe | |
| 19.48. | OMe | 3-C$_6$H$_4$—C≡C—C$_4$H$_9$(n) | |
| 19.49. | OMe | 3-C$_6$H$_4$—C≡C—C$_3$H$_7$(n) | |
| 19.50. | OMe | 3-C$_6$H$_4$—C≡C—C$_8$H$_{17}$(n) | |
| 19.51. | NHMe | 3-C$_6$H$_4$—C≡C—C$_6$H$_3$Cl$_2$(2',4') | |
| 19.52. | NHMe | 3-C$_6$H$_4$—C≡C—C$_6$H$_5$ | |
| 19.53. | NHMe | 3-C$_6$H$_4$—C≡C—C$_6$H$_4$(OCH$_3$)(4') | |
| 19.54. | NHMe | 3-C$_6$H$_4$—C≡C—C$_6$H$_3$(CF$_3$)$_2$(3',5') | |
| 19.55. | NHMe | 3-C$_6$H$_4$—C≡C—C$_6$H$_4$(CF$_3$)(3') | |
| 19.56. | NHMe | 3-C$_6$H$_4$—C≡C—CO—C$_6$H$_4$(CF$_3$)(3') | |
| 19.57. | NHMe | 3-C$_6$H$_4$—C≡C—CO—C$_6$H$_5$ | |
| 19.58. | NHMe | 3-C$_6$H$_4$—C≡C—CO—C$_6$H$_4$(Cl)(3') | |
| 19.59. | NHMe | 3-C$_6$H$_4$—C≡C—C≡C—C$_3$H$_7$(i) | |
| 19.60. | NHMe | 3-C$_6$H$_4$—C≡C—C≡C—C(CH$_3$)$_2$—OH | |
| 19.61. | NHMe | 3-C$_6$H$_4$—(C≡C)$_2$—C(CH$_3$)$_2$—OCOCH$_3$ | |
| 19.62. | NHMe | 3-C$_6$H$_4$—C≡C—C(CH$_3$)$_2$—OH | |
| 19.63. | NHMe | 3-C$_6$H$_4$—C≡C-pyrazinyl(2') | |
| 19.64. | NHMe | 3-C$_6$H$_4$—C≡C-pyridyl(3') | |
| 19.65. | NHMe | 3-C$_6$H$_4$—C≡C—CO-pyridyl(3') | |
| 19.66. | NHMe | 3-C$_6$H$_4$—C≡C-pyridyl(2') | |
| 19.67. | NHMe | 3-C$_6$H$_4$—C≡C-pyridyl(4') | |
| 19.68. | NHMe | 3-C$_6$H$_4$—C≡C—C$_6$H$_4$(CF$_3$)(4') | |
| 19.69. | NHMe | 3-C$_6$H$_4$—C≡C—C$_6$H$_4$(Cl)(4') | |
| 19.70. | NHMe | 3-C$_6$H$_4$—C≡C—CH$_2$—OH | |
| 19.71. | NHMe | 3-C$_6$H$_4$—C≡C-pyrimidinyl(2') | |
| 19.72. | NHMe | 3-C$_6$H$_4$—C≡C-pyrimidinyl(4') | |
| 19.73. | NHMe | 3-C$_6$H$_4$—C≡C-pyrimidinyl(5') | |
| 19.74. | NHMe | 3-C$_6$H$_4$—C≡C—I | |
| 19.75. | NHMe | 3-C$_6$H$_4$—C≡C—CH$_3$ | |
| 19.76. | NHMe | 3-C$_6$H$_4$—C≡C—Br | |
| 19.77. | NHMe | 3-C$_6$H$_4$—C≡C—C$_6$H$_4$(Br)(4') | |
| 19.78. | NHMe | 3-C$_6$H$_4$—C≡C—C$_6$H$_3$(OCH$_3$)$_3$(3',4',5') | |
| 19.79. | NHMe | 3-C$_6$H$_4$—C≡C—C$_6$H$_3$(CH$_3$)$_2$(3',5') | |
| 19.80. | NHMe | 3-C$_6$H$_4$—C≡C-thiazolyl(2') | |
| 19.81. | NHMe | 3-C$_6$H$_4$—C≡C-oxazolyl(2') | |
| 19.82. | NHMe | 3-C$_6$H$_4$—C≡C-thienyl(2') | |
| 19.83. | NHMe | 3-C$_6$H$_4$—C≡C-thienyl(3') | |
| 19.84. | NHMe | 3-C$_6$H$_4$—C≡C—Et | |
| 19.85. | NHMe | 4-C$_6$H$_4$—C≡C—H | |
| 19.86. | NHMe | 2-C$_6$H$_4$—C≡C—H | |
| 19.87. | NHMe | 4-C$_6$H$_4$—C≡C—CH$_3$ | |
| 19.88. | NHMe | 2-C$_6$H$_4$—C≡C—Br | |
| 19.89. | NHMe | 2-C$_6$H$_4$—C≡C—C(CH$_3$)$_2$—OH | |
| 19.90. | NHMe | 4-C$_6$H$_4$—C≡C—C(CH$_3$)$_2$—OH | |
| 19.91. | NHMe | 3-C$_6$H$_4$—C≡C—CF$_3$ | |
| 19.92. | NHMe | 3-C$_6$H$_4$—C≡C—COOEt | |
| 19.93. | NHMe | 3-C$_6$H$_4$—C≡C—COOMe | |
| 19.94. | NHMe | 2-C$_6$H$_4$—C≡C—C(CH$_3$)$_2$—OH | |
| 19.95. | NHMe | 3-C$_6$H$_4$—C≡C—C(CH$_3$)$_2$—O—CH$_3$ | |
| 19.96. | NHMe | 4-C$_6$H$_4$—C≡C—C(CH$_3$)$_2$—O—CH$_3$ | |
| 19.97. | NHMe | 3-C$_6$H$_4$—C≡C—CH$_2$—OMe | |
| 19.98. | NHMe | 3-C$_6$H$_4$—C≡C—C$_4$H$_9$(n) | |

TABLE 19-continued

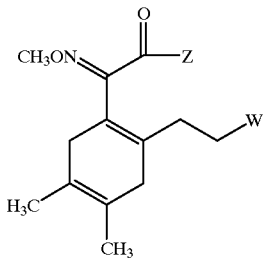

| Comp. No. | Z | W | Physical data m.p. |
|---|---|---|---|
| 19.99. | NHMe | 3-C$_6$H$_4$—C≡C—C$_3$H$_7$(n) | |
| 19.100. | NHMe | 3-C$_6$H$_4$—C≡C—C$_8$H$_{17}$(n) | |
| 19.101. | NHMe | 3-C$_6$H$_4$—C≡C—C$_6$H$_4$(CH$_3$)(3') | |
| 19.102. | NHMe | 3-C$_6$H$_4$—C≡C—CH$_2$-morpholinyl(1) | |
| 19.103. | NHMe | 3-C$_6$H$_4$—CH$_2$—CH$_2$—CH$_2$-morpholinyl(1) | |
| 19.104. | NHMe | 3-C$_6$H$_4$—C≡C—CH$_2$—Cl | |
| 19.105. | OMe | 3-C$_6$H$_4$—C≡C—C$_6$H$_4$(CH$_3$)(3') | |
| 19.106. | NHMe | 3-C$_6$H$_4$—C≡C—CH$_2$—O—C$_6$H$_3$(Cl$_2$)(2',4') | |
| 19.107. | NHMe | 3-C$_6$H$_4$—C≡C—CH$_2$—O—C$_6$H$_4$(CH$_3$)(2') | |
| 19.108. | NHMe | 3-C$_6$H$_4$—C≡C—CH$_2$—O—C$_6$H$_4$(CH$_3$)(3') | |
| 19.109. | OMe | 3-C$_6$H$_4$—C≡C—CH$_2$—O—N═C(CH$_3$)C$_6$H$_4$(CF$_3$)(3') | |
| 19.110. | OMe | 3-C$_6$H$_4$—C≡C—CH(OH)—C$_6$H$_4$(F)(4')OC$_6$H$_5$(3') | |
| 19.111. | OMe | 3-C$_6$H$_4$—C≡C—(CH$_2$)$_3$—O—C$_6$H$_4$(OC$_6$H$_5$)(4') | |

TABLE 19a

Compounds of the formula

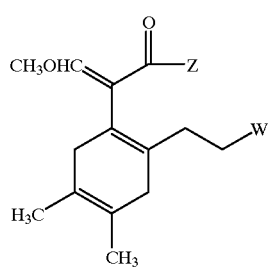

in which Z and W have the meanings of the corresponding compounds of Table 19.

TABLE 20

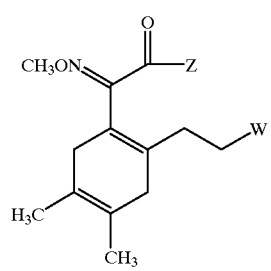

| Comp. No. | Z | W | Physical data |
|---|---|---|---|
| 20.001. | OMe | 3-C$_6$H$_4$—CH═CH—C$_6$H$_3$Cl$_2$(2',4') | |
| 20.002. | OMe | 3-C$_6$H$_4$—CH═CH—C$_6$H$_5$ | |

TABLE 20-continued

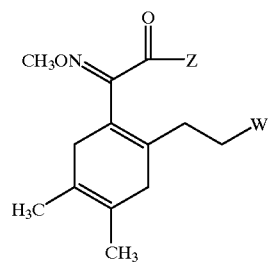

| Comp. No. | Z | W | Physical data |
|---|---|---|---|
| 20.003. | OMe | 3-C$_6$H$_4$—CH═CH—C$_6$H$_4$(OCH$_3$)(4') | |
| 20.004. | OMe | 3-C$_6$H$_4$—CH═CH—C$_6$H$_3$(CF$_3$)(3',5') | |
| 20.005. | OMe | 3-C$_6$H$_4$—CH═CH—C$_6$H$_4$(CF$_3$)(3') | |
| 20.006. | OMe | 3-C$_6$H$_4$—CH═CH—CO—C$_6$H$_4$(CF$_3$)(3') | |
| 20.007. | OMe | 3-C$_6$H$_4$—CH═CH—CO—C$_6$H$_5$ | |
| 20.008. | OMe | 3-C$_6$H$_4$—CH═CH—CO—C$_6$H$_4$(Cl)(3') | |
| 20.009. | OMe | 3-C$_6$H$_4$—CH═CH—C(CH$_3$)$_2$—OH | |
| 20.010. | OMe | 3-C$_6$H$_4$—CH═CH-pyrazinyl(2') | |
| 20.011. | OMe | 3-C$_6$H$_4$—CH═CH-pyridyl(3') | |
| 20.012. | OMe | 3-C$_6$H$_4$—CH═CH—CO-pyridyl(3') | |
| 20.013. | OMe | 3-C$_6$H$_4$—CH═CH-pyridyl(2') | |
| 20.014. | OMe | 3-C$_6$H$_4$—CH═CH-pyridyl(4') | |
| 20.015. | OMe | 3-C$_6$H$_4$—CH═CH—C$_6$H$_4$(CF$_3$)(4') | |
| 20.016. | OMe | 3-C$_6$H$_4$—CH═CH—C$_6$H$_4$(Cl)(4') | |
| 20.017. | OMe | 3-C$_6$H$_4$—CH═CH—CH$_2$—OH | |
| 20.018. | OMe | 3-C$_6$H$_4$—CH═CH-pyrimidinyl(2') | |
| 20.019. | OMe | 3-C$_6$H$_4$—CH═CH-pyrimidinyl(4') | |
| 20.020. | OMe | 3-C$_6$H$_4$—CH═CH-pyrimidinyl(5') | |
| 20.021. | OMe | 3-C$_6$H$_4$—CH═CH—I | |
| 20.022. | OMe | 3-C$_6$H$_4$—CH═CH—CH$_3$ | |
| 20.023. | OMe | 3-C$_6$H$_4$—CH═CH—Br | |
| 20.024. | OMe | 3-C$_6$H$_4$—CH═CH—C$_6$H$_4$(Br)(4') | |
| 20.025. | OMe | 3-C$_6$H$_4$—CH═CH—C$_6$H$_2$(OCH$_3$)$_3$(3',4',5') | |

TABLE 20-continued

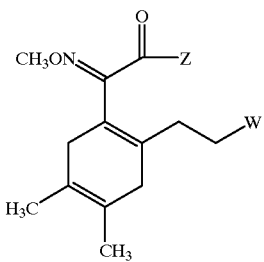

| Comp. No. | Z | W | Physical data |
|---|---|---|---|
| 20.026. | OMe | 3-C$_6$H$_4$—CH=CH—C$_6$H$_3$(CH$_3$)$_2$(3',5') | |
| 20.027. | OMe | 3-C$_6$H$_4$—CH=CH-thiazolyl(2') | |
| 20.028. | OMe | 3-C$_6$H$_4$—CH=CH-oxazolyl(2') | |
| 20.029. | OMe | 3-C$_6$H$_4$—CH=CH-thienyl(2') | |
| 20.030. | OMe | 3-C$_6$H$_4$—CH=CH-thienyl(3') | |
| 20.031. | OMe | 3-C$_6$H$_4$—CH=CH—Et | |
| 20.032. | OMe | 4-C$_6$H$_4$—CH=CH2 | |
| 20.033. | OMe | 2-C$_6$H$_4$—CH=CH2 | |
| 20.034. | OMe | 4-C$_6$H$_4$—CH=CH—CH$_3$ | |
| 20.035. | OMe | 2-C$_6$H$_4$—CH=CH—Br | |
| 20.036. | OMe | 2-C$_6$H$_4$—CH=CH—C(CH$_3$)$_2$—OH | |
| 20.037. | OMe | 4-C$_6$H$_4$—CH=CH—(CH$_3$)$_2$—OH | |
| 20.038. | OMe | 3-C$_6$H$_4$—CH=CH—CF$_3$ | |
| 20.039. | OMe | 3-C$_6$H$_4$—CH=CH—COOEt | |
| 20.040. | OMe | 3-C$_6$H$_4$—CH=CH—COOMe | |
| 20.041. | OMe | 2-C$_6$H$_4$—CH=CH—C(CH$_3$)$_2$—OH | |
| 20.042. | OMe | 3-C$_6$H$_4$—CH=CH—C(CH$_3$)$_2$—O—CH$_3$ | |
| 20.043. | OMe | 4-C$_6$H$_4$—CH=CH—C(CH$_3$)$_2$—O—CH$_3$ | |
| 20.044. | OMe | 3-C$_6$H$_4$—CH=CH—CH$_2$—OMe | |
| 20.045. | OMe | 3-C$_6$H$_4$—CH=CH—C$_4$H$_9$(n) | |
| 20.046. | OMe | 3-C$_6$H$_4$—CH=CH—C$_3$H$_7$(n) | |
| 20.047. | OMe | 3-C$_6$H$_4$—CH=CH—C$_8$H$_{17}$(n) | |
| 20.048. | NHMe | 3-C$_6$H$_4$—CH=CH—C$_6$H$_3$Cl$_2$(2',4') | |
| 20.049. | NHMe | 3-C$_6$H$_4$—CH=CH—C$_6$H$_5$ | |
| 20.050. | NHMe | 3-C$_6$H$_4$—CH=CH—C$_6$H$_4$(OCH$_3$)(4') | |
| 20.051. | NHMe | 3-C$_6$H$_4$—CH=CH—C$_6$H$_3$(CF$_3$)$_2$(3',5') | |
| 20.052. | NHMe | 3-C$_6$H$_4$—CH=CH—C$_6$H$_4$(CF$_3$)(3') | |
| 20.053. | NHMe | 3-C$_6$H$_4$—CH=CH—CO—C$_6$H$_4$(CF$_3$)(3') | |
| 20.054. | NHMe | 3-C$_6$H$_4$—CH=CH—CO—C$_6$H$_5$ | |
| 20.055. | NHMe | 3-C$_6$H$_4$—CH=CH—CO—C$_6$H$_4$(Cl)(3') | |
| 20.056. | NHMe | 3-C$_6$H$_4$—CH=CH—C(CH$_3$)$_2$—OH | |
| 20.057. | NHMe | 3-C$_6$H$_4$—CH=CH-pyrazinyl(2') | |
| 20.058. | NHMe | 3-C$_6$H$_4$—CH=CH-pyridyl(3') | |
| 20.059. | NHMe | 3-C$_6$H$_4$—CH=CH—CO-pyridyl(3') | |
| 20.060. | NHMe | 3-C$_6$H$_4$—CH=CH-pyridyl(2') | |
| 20.061. | NHMe | 3-C$_6$H$_4$—CH=CH-pyridyl(4') | |
| 20.062. | NHMe | 3-C$_6$H$_4$—CH=CH—C$_6$H$_4$(CF$_3$)(4') | |
| 20.063. | NHMe | 3-C$_6$H$_4$—CH=CH—C$_6$H$_4$(Cl)(4') | |
| 20.064. | NHMe | 3-C$_6$H$_4$—CH=CH—CH$_2$—OH | |
| 20.065. | NHMe | 3-C$_6$H$_4$—CH=CH-pyrimidinyl(2') | |
| 20.066. | NHMe | 3-C$_6$H$_4$—CH=CH-pyrimidinyl(4') | |
| 20.067. | NHMe | 3-C$_6$H$_4$—CH=CH-pyrimidinyl(5') | |
| 20.068. | NHMe | 3-C$_6$H$_4$—CH=CH—I | |
| 20.069. | NHMe | 3-C$_6$H$_4$—CH=CH—CH$_3$ | |
| 20.070. | NHMe | 3-C$_6$H$_4$—CH=CH—Br | |
| 20.071. | NHMe | 3-C$_6$H$_4$—CH=CH—C$_6$H$_4$(Br)(4') | |
| 20.072. | NHMe | 3-C$_6$H$_4$—CH=CH—C$_6$H$_2$(OCH$_3$)$_3$(3',4',5') | |
| 20.073. | NHMe | 3-C$_6$H$_4$—CH=CH—C$_6$H$_3$(CH$_3$)$_2$(3',5') | |
| 20.074. | NHMe | 3-C$_6$H$_4$—CH=CH-thiazolyl(2') | |
| 20.075. | NHMe | 3-C$_6$H$_4$—CH=CH-oxazolyl(2') | |
| 20.076. | NHMe | 3-C$_6$H$_4$—CH=CH-thienyl(2') | |
| 20.077. | NHMe | 3-C$_6$H$_4$—CH=CH-thienyl(3') | |
| 20.078. | NHMe | 3-C$_6$H$_4$—CH=CH—Et | |
| 20.079. | NHMe | 4-C$_6$H$_4$—CH=CH2 | |
| 20.080. | NHMe | 2-C$_6$H$_4$—CH=CH2 | |
| 20.081. | NHMe | 4-C$_6$H$_4$—CH=CH—CH$_3$ | |
| 20.082. | NHMe | 2-C$_6$H$_4$—CH=CH—Br | |
| 20.083. | NHMe | 2-C$_6$H$_4$—CH=CH—C(CH$_3$)$_2$—OH | |
| 20.084. | NHMe | 4-C$_6$H$_4$—CH=CH—C(CH$_3$)$_2$—OH | |
| 20.085. | NHMe | 3-C$_6$H$_4$—CH=CH—CF$_3$ | |
| 20.086. | NHMe | 3-C$_6$H$_4$—CH=CH—COOEt | |

TABLE 20-continued

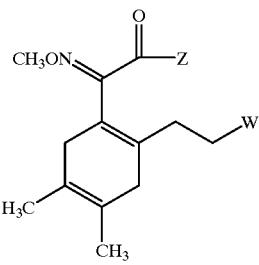

| Comp. No. | Z | W | Physical data |
|---|---|---|---|
| 20.087. | NHMe | 3-C$_6$H$_4$—CH=CH—COOMe | |
| 20.088. | NHMe | 2-C$_6$H$_4$—CH=CH—C(CH$_3$)$_2$—OH | |
| 20.089. | NHMe | 3-C$_6$H$_4$—CH=CH—C(CH$_3$)$_2$—O—CH$_3$ | |
| 20.090. | NHMe | 4-C$_6$H$_4$—CH=CH—C(CH$_3$)$_2$—O—CH$_3$ | |
| 20.091. | NHMe | 3-C$_6$H$_4$—CH=CH—CH$_2$—OMe | |
| 20.092. | NHMe | 3-C$_6$H$_4$—CH=CH—C$_4$H$_9$(n) | |
| 20.093. | NHMe | 3-C$_6$H$_4$—CH=CH—C$_3$H$_7$(n) | |
| 20.094. | NHMe | 3-C$_6$H$_4$—CH=CH—C$_8$H$_{17}$(n) | |
| 20.095. | NHMe | 3-C$_6$H$_4$—CH=CH—C$_6$H$_4$(CH$_3$)(3') | |
| 20.096. | NHMe | 3-C$_6$H$_4$—CH=CH—CH$_2$-morpholinyl(1) | |
| 20.097. | NHMe | 3-C$_6$H$_4$—CH=CH—CH$_2$-piperidinyl(1) | |
| 20.098. | NHMe | 3-C$_6$H$_4$—CH=CH—CH$_2$—Cl | |
| 20.099. | OMe | 3-C$_6$H$_4$—CH=CH—C$_6$H$_4$(CH$_3$)(3') | |
| 20.100. | NHMe | 3-C$_6$H$_4$—CH=CH—CH$_2$—O—C$_6$H$_3$(Cl$_2$)(2',4') | |
| 20.101. | NHMe | 3-C$_6$H$_4$—CH=CH—CH$_2$—O—C$_6$H$_4$(CH$_3$)(2') | |
| 20.102. | NHMe | 3-C$_6$H$_4$—CH=CH—CH$_2$—O—C$_6$H$_4$(CH$_3$)(3') | |

TABLE 20a

Compounds of the formula

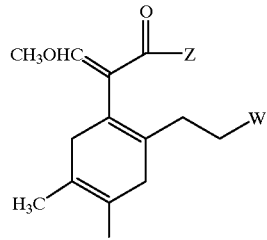

in which Z and W have the meanings of the corresponding compounds of Table 20.

TABLE 21

$$\text{Structure: central cyclohexadiene ring with CH}_3\text{ON=C(C(=O)-Z) substituent, CH}_2\text{CH}_2\text{-W substituent, and two CH}_3 \text{ groups}$$

| Comp. No. | Z | W | Physical data m.p. |
|---|---|---|---|
| 21.001. | OMe | 3-C₆H₄—CH₂—CH₂—C₆H₃Cl₂(2',4') | |
| 21.002. | OMe | 3-C₆H₄—CH₂—CH₂—C₆H₅ | |
| 21.003. | OMe | 3-C₆H₄—CH₂—CH₂—C₆H₄(OCH₃)(4') | |
| 21.004. | OMe | 3-C₆H₄—CH₂—CH₂—C₆H₃(CF₃)₂(3',5') | |
| 21.005. | OMe | 3-C₆H₄—CH₂—CH₂—C₆H₄(CF₃)(3') | |
| 21.006. | OMe | 3-C₆H₄—CH₂—CH₂—CO—C₆H₄(CF₃)(3') | |
| 21.007. | OMe | 3-C₆H₄—CH₂—CH₂—CO—C₆H₅ | |
| 21.008. | OMe | 3-C₆H₄—CH₂—CH₂—CO—C₆H₄(Cl)(3') | |
| 21.009. | OMe | 3-C₆H₄—CH₂—CH₂—C(CH₃)₂—OH | |
| 21.010. | OMe | 3-C₆H₄—CH₂—CH₂-pyrazinyl(2') | |
| 21.011. | OMe | 3-C₆H₄—CH₂—CH₂-pyridyl(3') | |
| 21.012. | OMe | 3-C₆H₄—CH₂—CH₂—CO-pyridyl(3') | |
| 21.013. | OMe | 3-C₆H₄—CH₂—CH₂-pyridyl(2') | |
| 21.014. | OMe | 3-C₆H₄—CH₂—CH₂-pyridyl(4') | |
| 21.015. | OMe | 3-C₆H₄—CH₂—CH₂—C₆H₄(CF₃)(4') | |
| 21.016. | OMe | 3-C₆H₄—CH₂—CH₂—C₆H₄(Cl)(4') | |
| 21.017. | OMe | 3-C₆H₄—CH₂—CH₂—CH₂—OH | |
| 21.018. | OMe | 3-C₆H₄—CH₂—CH₂-pyrimidinyl(2') | |
| 21.019. | OMe | 3-C₆H₄—CH₂—CH₂-pyrimidinyl(4') | |
| 21.020. | OMe | 3-C₆H₄—CH₂—CH₂-pyrimidinyl(5') | |
| 21.021. | OMe | 3-C₆H₄—CH₂—CH₂—I | |
| 21.022. | OMe | 3-C₆H₄—CH₂—CH₂—CH₃ | |
| 21.023. | OMe | 3-C₆H₄—CH₂—CH₂—Br | |
| 21.024. | OMe | 3-C₆H₄—CH₂—CH₂—C₆H₄(Br)(4') | |
| 21.025. | OMe | 3-C₆H₄—CH₂—CH₂—C₆H₂(OCH₃)₃(3',4',5') | |
| 21.026. | OMe | 3-C₆H₄—CH₂—CH₂—C₆H₃(CH₃)₂(3',5') | |
| 21.027. | OMe | 3-C₆H₄—CH₂—CH₂-thiazolyl(2') | |
| 21.028. | OMe | 3-C₆H₄—CH₂—CH₂-oxazolyl(2') | |
| 21.029. | OMe | 3-C₆H₄—CH₂—CH₂-thienyl(2') | |
| 21.030. | OMe | 3-C₆H₄—CH₂—CH₂-thienyl(3') | |
| 21.031. | OMe | 3-C₆H₄—CH₂—CH₂—Et | |
| 21.032. | OMe | 4-C₆H₄—CH₂—CH₃ | |
| 21.033. | OMe | 2-C₆H₄—CH₂—CH₃ | |
| 21.034. | OMe | 4-C₆H₄—CH₂—CH₂—CH₃ | |
| 21.035. | OMe | 2-C₆H₄—CH₂—CH₂—Br | |
| 21.036. | OMe | 2-C₆H₄—CH₂—CH₂—C(CH₃)₂—OH | |
| 21.037. | OMe | 4-C₆H₄—CH₂—CH₂—(CH₃)₂—OH | |
| 21.038. | OMe | 3-C₆H₄—CH₂—CH₂—CF₃ | |
| 21.039. | OMe | 3-C₆H₄—CH₂—CH₂—COOEt | |
| 21.040. | OMe | 3-C₆H₄—CH₂—CH₂—COOMe | |
| 21.041. | OMe | 2-C₆H₄—CH₂—CH₂—C(CH₃)₂—OH | |
| 21.042. | OMe | 3-C₆H₄—CH₂—CH₂—C(CH₃)₂—O—CH₃ | |
| 21.043. | OMe | 4-C₆H₄—CH₂—CH₂—C(CH₃)₂—O—CH₃ | |
| 21.044. | OMe | 3-C₆H₄—CH₂—CH₂—CH₂—OMe | |
| 21.045. | OMe | 3-C₆H₄—CH₂—CH₂—C₄H₉(n) | |
| 21.046. | OMe | 3-C₆H₄—CH₂—CH₂—C₃H₇(n) | |
| 21.047. | OMe | 3-C₆H₄—CH₂—CH₂—C₆H₁₇(n) | |
| 21.048. | NHMe | 3-C₆H₄—CH₂—CH₂—C₆H₃Cl₂(2',4') | |
| 21.049. | NHMe | 3-C₆H₄—CH₂—CH₂—C₆H₅ | |
| 21.050. | NHMe | 3-C₆H₄—CH₂—CH₂—C₆H₄(OCH₃)(4') | |
| 21.051. | NHMe | 3-C₆H₄—CH₂—CH₂—C₆H₃(CF₃)₂(3',5') | |
| 21.052. | NHMe | 3-C₆H₄—CH₂—CH₂—C₆H₄(CF₃)(3') | |
| 21.053. | NHMe | 3-C₆H₄—CH₂—CH₂—CO—C₆H₄(CF₃)(3') | |
| 21.054. | NHMe | 3-C₆H₄—CH₂—CH₂—CO—C₆H₅ | |
| 21.055. | NHMe | 3-C₆H₄—CH₂—CH₂—CO—C₆H₄(Cl)(3') | |
| 21.056. | NHMe | 3-C₆H₄—CH₂—CH₂—C(CH₃)₂—OH | |
| 21.057. | NHMe | 3-C₆H₄—CH₂—CH₂-pyrazinyl(2') | |
| 21.058. | NHMe | 3-C₆H₄—CH₂—CH₂-pyridyl(3') | |
| 21.059. | NHMe | 3-C₆H₄—CH₂—CH₂—CO-pyridyl(3') | |
| 21.060. | NHMe | 3-C₆H₄—CH₂—CH₂-pyridyl(2') | |
| 21.061. | NHMe | 3-C₆H₄—CH₂—CH₂-pyridyl(4') | |
| 21.062. | NHMe | 3-C₆H₄—CH₂—CH₂—C₆H₄(CF₃)(4') | |

TABLE 21-continued

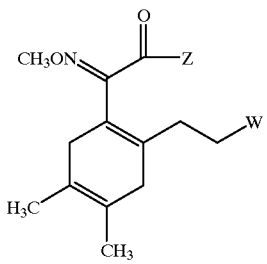

| Comp. No. | Z | W | Physical data m.p. |
|---|---|---|---|
| 21.063. | NHMe | 3-$C_6H_4$—$CH_2$—$CH_2$—$C_6H_4$(Cl)(4') | |
| 21.064. | NHMe | 3-$C_6H_4$—$CH_2$—$CH_2$—$CH_2$—OH | |
| 21.065. | NHMe | 3-$C_6H_4$—$CH_2$—$CH_2$-pyrimidinyl(2') | |
| 21.066. | NHMe | 3-$C_6H_4$—$CH_2$—$CH_2$-pyrimidinyl(4') | |
| 21.067. | NHMe | 3-$C_6H_4$—$CH_2$—$CH_2$-pyrimidinyl(5') | |
| 21.068. | NHMe | 3-$C_6H_4$—$CH_2$—$CH_2$—I | |
| 21.069. | NHMe | 3-$C_6H_4$—$CH_2$—$CH_2$—$CH_3$ | |
| 21.070. | NHMe | 3-$C_6H_4$—$CH_2$—$CH_2$—Br | |
| 21.071. | NHMe | 3-$C_6H_4$—$CH_2$—$CH_2$—$C_6H_4$(Br)(4') | |
| 21.072. | NHMe | 3-$C_6H_4$—$CH_2$—$CH_2$—$C_6H_2$($OCH_3$)$_3$(3',4',5') | |
| 21.073. | NHMe | 3-$C_6H_4$—$CH_2$—$CH_2$—$C_6H_3$($CH_3$)$_2$(3',5') | |
| 21.074. | NHMe | 3-$C_6H_4$—$CH_2$—$CH_2$-thiazolyl(2') | |
| 21.075. | NHMe | 3-$C_6H_4$—$CH_2$—$CH_2$-oxazolyl(2') | |
| 21.076. | NHMe | 3-$C_6H_4$—$CH_2$—$CH_2$-thienyl(2') | |
| 21.077. | NHMe | 3-$C_6H_4$—$CH_2$—$CH_2$-thienyl(3') | |
| 21.078. | NHMe | 3-$C_6H_4$—$CH_2$—$CH_2$—Et | |
| 21.079. | NHMe | 4-$C_6H_4$—$CH_2$—$CH_3$ | |
| 21.080. | NHMe | 2-$C_6H_4$—$CH_2$—$CH_3$ | |
| 21.081. | NHMe | 4-$C_6H_4$—$CH_2$—$CH_2$—$CH_3$ | |
| 21.082. | NHMe | 2-$C_6H_4$—$CH_2$—$CH_2$—Br | |
| 21.083. | NHMe | 2-$C_6H_4$—$CH_2$—$CH_2$—$C(CH_3)_2$—OH | |
| 21.084. | NHMe | 4-$C_6H_4$—$CH_2$—$CH_2$—$C(CH_3)_2$—OH | |
| 21.085. | NHMe | 3-$C_6H_4$—$CH_2$—$CH_2$—$CF_3$ | |
| 21.086. | NHMe | 3-$C_6H_4$—$CH_2$—$CH_2$—COOEt | |
| 21.087. | NHMe | 3-$C_6H_4$—$CH_2$—$CH_2$—COOMe | |
| 21.088. | NHMe | 2-$C_6H_4$—$CH_2$—$CH_2$—$C(CH_3)_2$—OH | |
| 21.089. | NHMe | 3-$C_6H_4$—$CH_2$—$CH_2$—$C(CH_3)_2$—O—$CH_3$ | |
| 21.090. | NHMe | 4-$C_6H_4$—$CH_2$—$CH_2$—$C(CH_3)_2$—O—$CH_3$ | |
| 21.091. | NHMe | 3-$C_6H_4$—$CH_2$—$CH_2$—$CH_2$—OMe | |
| 21.092. | NHMe | 3-$C_6H_4$—$CH_2$—$CH_2$—$C_4H_9$(n) | |
| 21.093. | NHMe | 3-$C_6H_4$—$CH_2$—$CH_2$—$C_3H_7$(n) | |
| 21.094. | NHMe | 3-$C_6H_4$—$CH_2$—$CH_2$—$C_8H_{17}$(n) | |
| 21.095. | NHMe | 3-$C_6H_4$—$CH_2$—$CH_2$—$C_6H_4$($CH_3$)(3') | |
| 21.096. | NHMe | 3-$C_6H_4$—$CH_2$—$CH_2$—$CH_2$-morpholinyl(1) | |
| 21.097. | NHMe | 3-$C_6H_4$—$CH_2$—$CH_2$—$CH_2$-piperidinyl(1) | |
| 21.098. | NHMe | 3-$C_6H_4$—$CH_2$—$CH_2$—$CH_2$—Cl | |
| 21.099. | OMe | 3-$C_6H_4$—$CH_2$—$CH_2$—$C_6H_4$($CH_3$)(3') | |
| 21.100. | NHMe | 3-$C_6H_4$—$CH_2$—$CH_2$—$CH_2$—O—$C_6H_3$($Cl_2$)(2',4') | |
| 21.101. | NHMe | 3-$C_6H_4$—$CH_2$—$CH_2$—$CH_2$—O—$C_6H_4$($CH_3$)(2') | |
| 21.102. | NHMe | 3-$C_6H_4$—$CH_2$—$CH_2$—$CH_2$—O—$C_6H_4$($CH_3$)(3') | |

TABLE 21a

Compounds of the formula

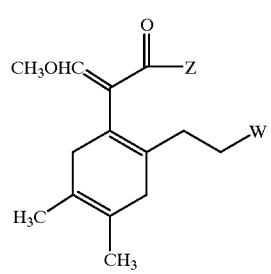

in which Z and W have the meanings of the corresponding compounds of Table 20.

TABLE 22

[Structure: a cyclohexadiene ring bearing CH₃ON=C(C(=O)-Z) substituent, a -CH₂CH₂-W substituent, and two CH₃ groups]

| Comp. No. | Z | W | Physical data m.p. |
|---|---|---|---|
| 22.001. | OMe | 3-$C_6H_4$—O—$CH_2$—$C_6H_3Cl_2$(2',4') | |
| 22.002. | OMe | 3-$C_6H_4$—O—$CH_2$—$C_6H_5$ | |
| 22.003. | OMe | 3-$C_6H_4$—O—$CH_2$—$C_6H_4$(OCH$_3$)(4') | |
| 22.004. | OMe | 3-$C_6H_4$—O—$CH_2$—$C_6H_3$(CF$_3$)(3',5') | |
| 22.005. | OMe | 3-$C_6H_4$—O—$CH_2$—$C_6H_4$(CF$_3$)(3') | |
| 22.006. | OMe | 3-$C_6H_4$—O—$CH_2$—CO—$C_6H_4$(CF$_3$)(3') | |
| 22.007. | OMe | 3-$C_6H_4$—O—$CH_2$—CO—$C_6H_5$ | |
| 22.008. | OMe | 3-$C_6H_4$—O—$CH_2$—CO—$C_6H_4$(Cl)(3') | |
| 22.009. | OMe | 3-$C_6H_4$—O—$CH_2$—C(CH$_3$)$_2$—OH | |
| 22.010. | OMe | 3-$C_6H_4$—O—$CH_2$-pyrazinyl(2') | |
| 22.011. | OMe | 3-$C_6H_4$—O—$CH_2$-pyridyl(3') | |
| 22.012. | OMe | 3-$C_6H_4$—O—$CH_2$—CO-pyridyl(3') | |
| 22.013. | OMe | 3-$C_6H_4$—O—$CH_2$-pyridyl(2') | |
| 22.014. | OMe | 3-$C_6H_4$—O—$CH_2$-pyridyl(4') | |
| 22.015. | OMe | 3-$C_6H_4$—O—$CH_2$—$C_6H_4$(CF$_3$)(4') | |
| 22.016. | OMe | 3-$C_6H_4$—O—$CH_2$—$C_6H_4$(Cl)(4') | |
| 22.017. | OMe | 3-$C_6H_4$—O—$CH_2$—$CH_2$—OH | |
| 22.018. | OMe | 3-$C_6H_4$—O—$CH_2$-pyrimidinyl(2') | |
| 22.019. | OMe | 3-$C_6H_4$—O—$CH_2$-pyrimidinyl(4') | |
| 22.020. | OMe | 3-$C_6H_4$—O—$CH_2$-pyrimidinyl(5') | |
| 22.021. | OMe | 3-$C_6H_4$—O—$CH_2$—I | |
| 22.022 | OMe | 3-$C_6H_4$—O—$CH_2$—$CH_3$ | |
| 22.023. | OMe | 3-$C_6H_4$—O—$CH_2$—Br | |
| 22.024. | OMe | 3-$C_6H_4$—O—$CH_2$—$C_6H_4$(Br)(4') | |
| 22.025. | OMe | 3-$C_6H_4$—O—$CH_2$—$C_6H_2$(OCH$_3$)$_3$(3',4',5') | |
| 22.026. | OMe | 3-$C_6H_4$—O—$CH_2$—$C_6H_3$(CH$_3$)$_2$(3',5') | |
| 22.027. | OMe | 3-$C_6H_4$—O—$CH_2$-thiazolyl(2') | |
| 22.028. | OMe | 3-$C_6H_4$—O—$CH_2$-oxazolyl(2') | |
| 22.029. | OMe | 3-$C_6H_4$—O—$CH_2$-thienyl(2') | |
| 22.030. | OMe | 3-$C_6H_4$—O—$CH_2$-thienyl(3') | |
| 22.031. | OMe | 3-$C_6H_4$—O—$CH_2$-Et | |
| 22.032. | OMe | 4-$C_6H_4$—O—$CH_3$ | |
| 22.033. | OMe | 2-$C_6H_4$—O—$CH_3$ | |
| 22.034. | OMe | 4-$C_6H_4$—O—$CH_2$—$CH_3$ | |
| 22.035. | OMe | 2-$C_6H_4$—O—$CH_2$—Br | |
| 22.036. | OMe | 2-$C_6H_4$—O—$CH_2$—C(CH$_3$)$_2$—OH | |
| 22.037. | OMe | 4-$C_6H_4$—O—$CH_2$—(CH$_3$)$_2$—OH | |
| 22.038. | OMe | 3-$C_6H_4$—O—$CH_2$—CF$_3$ | |
| 22.039. | OMe | 3-$C_6H_4$—O—$CH_2$—COOEt | |
| 22.040. | OMe | 3-$C_6H_4$—O—$CH_2$—COOMe | |
| 22.041. | OMe | 2-$C_6H_4$—O—$CH_2$—C(CH$_3$)$_2$—OH | |
| 22.042. | OMe | 3-$C_6H_4$—O—$CH_2$—C(CH$_3$)$_2$—O—CH$_3$ | |
| 22.043. | OMe | 4-$C_6H_4$—O—$CH_2$—C(CH$_3$)$_2$—O—CH$_3$ | |
| 22.044. | OMe | 3-$C_6H_4$—O—$CH_2$—$CH_2$—OMe | |
| 22.045. | OMe | 3-$C_6H_4$—O—$CH_2$—$C_4H_9$(n) | |
| 22.046. | OMe | 3-$C_6H_4$—O—$CH_2$—$C_3H_7$(n) | |
| 22.047. | OMe | 3-$C_6H_4$—O—$CH_2$—$C_8H_{17}$(n) | |
| 22.048. | NHMe | 3-$C_6H_4$—O—$CH_2$—$C_6H_3Cl_2$(2',4') | |
| 22.049. | NHMe | 3-$C_6H_4$—O—$CH_2$—$C_6H_5$ | |
| 22.050. | NHMe | 3-$C_6H_4$—O—$CH_2$—$C_6H_4$(OCH$_3$)(4') | |
| 22.051. | NHMe | 3-$C_6H_4$—O—$CH_2$—$C_6H_3$(CF$_3$)$_2$(3',5') | |
| 22.052. | NHMe | 3-$C_6H_4$—O—$CH_2$—$C_6H_4$(CF$_3$)(3') | |
| 22.053. | NHMe | 3-$C_6H_4$—O—$CH_2$—CO—$C_6H_4$(CF$_3$)(3') | |
| 22.054. | NHMe | 3-$C_6H_4$—O—$CH_2$—CO—$C_6H_5$ | |
| 22.055. | NHMe | 3-$C_6H_4$—O—$CH_2$—CO—$C_6H_4$(Cl)(3') | |
| 22.056. | NHMe | 3-$C_6H_4$—O—$CH_2$—C(CH$_3$)$_2$—OH | |
| 22.057. | NHMe | 3-$C_6H_4$—O—$CH_2$-pyrazinyl(2') | |
| 22.058. | NHMe | 3-$C_6H_4$—O—$CH_2$-pyridyl(3') | |
| 22.059. | NHMe | 3-$C_6H_4$—O—$CH_2$—CO-pyridyl(3') | |

TABLE 22-continued

[Chemical structure: benzene-like ring with CH₃ON=, C(=O)-Z group, CH₂CH₂-W substituent, and two CH₃ groups]

| Comp. No. | Z | W | Physical data m.p. |
|---|---|---|---|
| 22.060. | NHMe | 3-C₆H₄—O—CH₂-pyridyl(2') | |
| 22.061. | NHMe | 3-C₆H₄—O—CH₂-pyridyl(4') | |
| 22.062. | NHMe | 3-C₆H₄—O—CH₂—C₆H₄(CF₃)(4') | |
| 22.063. | NHMe | 3-C₆H₄—O—CH₂—C₆H₄(Cl)(4') | |
| 22.064. | NHMe | 3-C₆H₄—O—CH₂—OH | |
| 22.065. | NHMe | 3-C₆H₄—O—CH₂-pyrimidinyl(2') | |
| 22.066. | NHMe | 3-C₆H₄—O—CH₂-pyrimidinyl(4') | |
| 22.067. | NHMe | 3-C₆H₄—O—CH₂-pyrimidinyl(5') | |
| 22.068. | NHMe | 3-C₆H₄—O—CH₂—I | |
| 22.069. | NHMe | 3-C₆H₄—O—CH₂—CH₃ | |
| 22.070. | NHMe | 3-C₆H₄—O—CH₂—Br | |
| 22.071. | NHMe | 3-C₆H₄—O—CH₂—C₆H₄(Br)(4') | |
| 22.072. | NHMe | 3-C₆H₄—O—CH₂—C₆H₂(OCH₃)₃(3',4',5') | |
| 22.073. | NHMe | 3-C₆H₄—O—CH₂—C₆H₃(CH₃)₂(3',5') | |
| 22.074. | NHMe | 3-C₆H₄—O—CH₂-thiazolyl(2') | |
| 22.075. | NHMe | 3-C₆H₄—O—CH₂-oxazolyl(2') | |
| 22.076. | NHMe | 3-C₆H₄—O—CH₂-thienyl(2') | |
| 22.077. | NHMe | 3-C₆H₄—O—CH₂-thienyl(3') | |
| 22.078. | NHMe | 3-C₆H₄—O—CH₂-Et | |
| 22.079. | NHMe | 4-C₆H₄—O—CH₃ | |
| 22.080. | NHMe | 2-C₆H₄—O—CH₃ | |
| 22.081. | NHMe | 4-C₆H₄—O—CH₂—CH₃ | |
| 22.082. | NHMe | 2-C₆H₄—O—CH₂—Br | |
| 22.083. | NHMe | 2-C₆H₄—O—CH₂—C(CH₃)₂—OH | |
| 22.084. | NHMe | 4-C₆H₄—O—CH₂—C(CH₃)₂—OH | |
| 22.085. | NHMe | 3-C₆H₄—O—CH₂—CF₃ | |
| 22.086. | NHMe | 3-C₆H₄—O—CH₂—COOEt | |
| 22.087. | NHMe | 3-C₆H₄—O—CH₂—COOMe | |
| 22.088. | NHMe | 2-C₆H₄—O—CH₂—C(CH₃)₂—OH | |
| 22.089. | NHMe | 3-C₆H₄—O—CH₂—C(CH₃)₂—O—CH₃ | |
| 22.090. | NHMe | 4-C₆H₄—O—CH₂—C(CH₃)₂—O—CH₃ | |
| 22.091. | NHMe | 3-C₆H₄—O—CH₂—CH₂—OMe | |
| 22.092. | NHMe | 3-C₆H₄—O—CH₂—C₄H₉(n) | |
| 22.093. | NHMe | 3-C₆H₄—O—CH₂—C₃H₇(n) | |
| 22.094. | NHMe | 3-C₆H₄—O—CH₂—C₈H₁₇(n) | |
| 22.095. | NHMe | 3-C₆H₄—O—CH₂—C₆H₄(CH₃)(3') | |
| 22.096. | NHMe | 3-C₆H₄—O—CH₂—CH₂-morpholinyl(1) | |
| 22.097. | NHMe | 3-C₆H₄—O—CH₂—CH₂-piperidinyl(1) | |
| 22.098. | NHMe | 3-C₆H₄—O—CH₂—CH₂—Cl | |
| 22.099. | OMe | 3-C₆H₄—O—CH₂—C₆H₄(CH₃)(3') | |
| 22.100. | NHMe | 3-C₆H₄—O—CH₂—CH₂—O—C₆H₃(Cl₂)(2',4') | |
| 22.101. | NHMe | 3-C₆H₄—O—CH₂—CH₂—O—C₆H₄(CH₃)(2') | |
| 22.102. | NHMe | 3-C₆H₄—O—CH₂—CH₂—O—C₆H₄(CH₃)(3') | |
| 22.103. | OMe | 3-C₆H₄—O—C₆H₂CN(2')(CH₃)₂(4',5') | |
| 22.104. | OMe | 3-C₆H₄—O—CH₂—C≡C—C₆H₅ | |
| 22.105. | OMe | 3-C₆H₄—O—CH₂—C≡C—C₆H₄(CH₃)(3') | |
| 22.106. | OMe | 3-C₆H₄—O—CH₂—CH₂—CH₂—C₆H₅ | |
| 22.107. | OMe | 3-C₆H₄—O—CH₂—CH₂—CH₂—C₆H₄(CH₃)(3') | |
| 22.108. | OMe | 3-C₆H₄—O—CH₂-pyridin-5'-yl(Cl)(2') | |
| 22.109. | OMe | 3-C₆H₄—O—CH₂-thiazol-5'-yl(Cl)(2') | |
| 22.110. | OMe | 3-C₆H₄—O—CH₂-thiazol-5'-yl | |
| 22.111. | OMe | 3-C₆H₄—O—CH₂-thiadiazol-5'-yl | |
| 22.112. | OMe | 3-C₆H₄—O—CH₂—C₆H₄NO₂(2') | |
| 22.113. | OMe | 3-C₆H₄—O—CH₂—C₆H₄NO₂(4') | |
| 22.114. | OMe | 3-C₆H₄—O—CH₂—C₆H₄Cl(2') | |
| 22.115. | OMe | 3-C₆H₄—O—CH₂—C₆H₃(CH₃)₂(3',4') | |
| 22.116. | OMe | 3-C₆H₄—O—CH₂—C₆H₄CF₃(2') | |
| 22.117. | OMe | 3-C₆H₄—O—CH₂-(3',4'-dimethylcyclohexa-1,4-dienyl) | |

TABLE 22a

Compounds of the formula

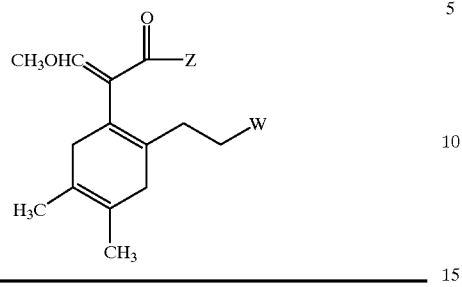

in which Z and W have the meanings of the corresponding compounds of Table 22.

TABLE 23

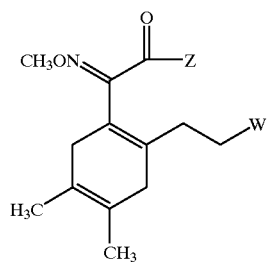

| Comp. No. | Z | W | Physical data m.p. |
|---|---|---|---|
| 23.001. | OMe | 3-$C_6H_4$—O—$C_6H_3Cl_2$(2',4') | |
| 23.002. | OMe | 3-$C_6H_4$—O—$C_6H_5$ | |
| 23.003. | OMe | 3-$C_6H_4$—O—$C_6H_4$($OCH_3$)(4') | |
| 23.004. | OMe | 3-$C_6H_4$—O—$C_6H_3$($CF_3$)$_2$(3',5') | |
| 23.005. | OMe | 3-$C_6H_4$—O—$C_6H_4$($CF_3$)(3') | |
| 23.006. | OMe | 3-$C_6H_4$—O—CO—$C_6H_4$($CF_3$)(3') | |
| 23.007. | OMe | 3-$C_6H_4$—O—CO—$C_6H_5$ | |
| 23.008. | OMe | 3-$C_6H_4$—O—CO—$C_6H_4$(Cl)(3') | |
| 23.009. | OMe | 3-$C_6H_4$—O—$C_6H_3$(CN)(3')($NO_2$)(4') | |
| 23.010. | OMe | 3-$C_6H_4$—O-pyrazinyl(2') | |
| 23.011. | OMe | 3-$C_6H_4$—O-pyridyl(3') | |
| 23.012. | OMe | 3-$C_6H_4$—O—CO-pyridyl(3') | |
| 23.013. | OMe | 3-$C_6H_4$—O-pyridyl(2') | |
| 23.014. | OMe | 3-$C_6H_4$—O-pyridyl(4') | |
| 23.015. | OMe | 3-$C_6H_4$—O—$C_6H_4$($CF_3$)(4') | |
| 23.016. | OMe | 3-$C_6H_4$—O—$C_6H_4$(Cl)(4') | |
| 23.017. | OMe | 3-$C_6H_4$—O—$C_6H_4$($NO_2$)(4') | |
| 23.018. | OMe | 3-$C_6H_4$—O-pyrimidinyl(2') | |
| 23.019. | OMe | 3-$C_6H_4$—O-pyrimidinyl(4') | |
| 23.020. | OMe | 3-$C_6H_4$—O-pyrimidinyl(5') | |
| 23.021. | OMe | 3-$C_6H_4$—O—CO—NH—$C_6H_4$(OMe)(4') | |
| 23.022. | OMe | 3-$C_6H_4$—O—$CH_3$ | |
| 23.023. | OMe | 3-$C_6H_4$—O—CO—NH—$C_6H_4$($CF_3$)(3') | |
| 23.024. | OMe | 3-$C_6H_4$—O—$C_6H_4$(Br)(4') | |
| 23.025. | OMe | 3-$C_6H_4$—O—$C_6H_2$($OCH_3$)$_3$(3',4',5') | |
| 23.026. | OMe | 3-$C_6H_4$—O—$C_6H_3$($CH_3$)$_2$(3',5') | |
| 23.027. | OMe | 3-$C_6H_4$—O-thiazolyl(2') | |
| 23.028. | OMe | 3-$C_6H_4$—O-oxazolyl(2') | |
| 23.029. | OMe | 3-$C_6H_4$—O-thienyl(2') | |
| 23.030. | OMe | 3-$C_6H_4$—O-thienyl(3') | |
| 23.031. | OMe | 3-$C_6H_4$—O-Et | |
| 23.032. | OMe | 3-$C_6H_4$—O—H | |
| 23.033. | OMe | 3-$C_6H_4$—O—H | |
| 23.034. | OMe | 3-$C_6H_4$—O—$CH_3$ | |
| 23.035. | OMe | 3-$C_6H_4$—O—CO—NH—$C_6H_4$(Cl)(4') | |
| 23.036. | OMe | 3-$C_6H_4$—O—CO—NH—$C_6H_3$($Cl_2$)(2',4') | |
| 23.037. | OMe | 3-$C_6H_4$—O—CO—NH—$C_6H_4$($NO_2$)(4') | |

TABLE 23-continued

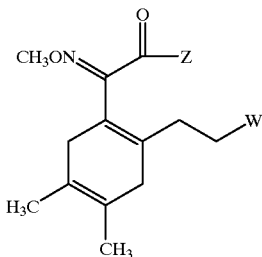

| Comp. No. | Z | W | Physical data m.p. |
|---|---|---|---|
| 23.038. | OMe | 3-$C_6H_4$—O—$CF_3$ | |
| 23.039. | OMe | 3-$C_6H_4$—O—COOEt | |
| 23.040. | OMe | 3-$C_6H_4$—O—COOMe | |
| 23.041. | OMe | 3-$C_6H_4$—O—CO—NH—$C_6H_4$—(Br)(4') | |
| 23.042. | OMe | 3-$C_6H_4$—O—CO—NH—$C_6H_4$—(I)(4') | |
| 23.043. | OMe | 3-$C_6H_4$—O—CO—NH—$C_6H_4$—($CH_3$)(2') | |
| 23.044. | OMe | 3-$C_6H_4$—O—$CH_2$—OMe | |
| 23.045. | OMe | 3-$C_6H_4$—O—$C_4H_9$(n) | |
| 23.046. | OMe | 3-$C_6H_4$—O—$C_3H_7$(n) | |
| 23.047. | OMe | 3-$C_6H_4$—O—$C_8H_{17}$(n) | |
| 23.048. | NHMe | 3-$C_6H_4$—O—$C_6H_3Cl_2$(2',4') | |
| 23.049. | NHMe | 3-$C_6H_4$—O—$C_6H_5$ | |
| 23.050. | NHMe | 3-$C_6H_4$—O—$C_6H_4$($OCH_3$)(4') | |
| 23.051. | NHMe | 3-$C_6H_4$—O—$C_6H_3$($CF_3$)$_2$(3',5') | |
| 23.052. | NHMe | 3-$C_6H_4$—O—$C_6H_4$($CF_3$)(3') | |
| 23.053. | NHMe | 3-$C_6H_4$—O—CO—$C_6H_4$($CF_3$)(3') | |
| 23.054. | NHMe | 3-$C_6H_4$—O—CO—$C_6H_5$ | |
| 23.055. | NHMe | 3-$C_6H_4$—O—CO—$C_6H_4$(Cl)(3') | |
| 23.056. | OMe | 3-$C_6H_4$—O—CO—NH—$C_6H_3$—($CH_3$)$_2$(2',6') | |
| 23.057. | NHMe | 3-$C_6H_4$—O-pyrazinyl(2') | |
| 23.058. | NHMe | 3-$C_6H_4$—O-pyridyl(3') | |
| 23.059. | NHMe | 3-$C_6H_4$—O—CO-pyridyl(3') | |
| 23.060. | NHMe | 3-$C_6H_4$—O-pyridyl(2') | |
| 23.061. | NHMe | 3-$C_6H_4$—O-pyridyl(4') | |
| 23.062. | NHMe | 3-$C_6H_4$—O—$C_6H_4$($CF_3$)(4') | |
| 23.063. | NHMe | 3-$C_6H_4$—O—$C_6H_4$(Cl)(4') | |
| 23.064. | OMe | 3-$C_6H_4$—O—CO—NH—$C_6H_3$-(Me)(2')(Et)(6') | |
| 23.065. | NHMe | 3-$C_6H_4$—O-pyrimidinyl(2') | |
| 23.066. | NHMe | 3-$C_6H_4$—O-pyrimidinyl(4') | |
| 23.067. | NHMe | 3-$C_6H_4$—O-pyrimidinyl(5') | |
| 23.068. | OMe | 3-$C_6H_4$—O—CO—NH—$C_6H_3$-(Me)$_2$(2',4') | |
| 23.069. | NHMe | 3-$C_6H_4$—O—$CH_3$ | |
| 23.070. | OMe | 3-$C_6H_4$—O—CO—NH—$C_6H_4$—(Cl)(3') | |
| 23.071. | NHMe | 3-$C_6H_4$—O—$C_6H_4$(Br)(4') | |
| 23.072. | NHMe | 3-$C_6H_4$—O—$C_6H_2$($OCH_3$)$_3$(3',4',5') | |
| 23.073. | NHMe | 3-$C_6H_4$—O—$C_6H_3$($CH_3$)$_2$(3',5') | |
| 23.074. | NHMe | 3-$C_6H_4$—O-thiazolyl(2') | |
| 23.075. | NHMe | 3-$C_6H_4$—O-oxazolyl(2') | |
| 23.076. | NHMe | 3-$C_6H_4$—O-thienyl(2') | |
| 23.077. | NHMe | 3-$C_6H_4$—O-thienyl(3') | |
| 23.078. | NHMe | 3-$C_6H_4$—O-Et | |
| 23.079. | NHMe | 3-$C_6H_4$—O—$CH_3$ | |
| 23.080. | NHMe | 3-$C_6H_4$—O—$CH_3$ | |
| 23.081. | NHMe | 3-$C_6H_4$—O—$CH_3$ | |
| 23.082. | OMe | 3-$C_6H_4$—O—CO—NH—$C_6H_4$—(Cl)(2') | |
| 23.083. | OMe | 3-$C_6H_4$—O—CO—NH—$C_6H_3$—(Cl)$_2$(3',5') | |
| 23.084. | OMe | 3-$C_6H_4$—O—CO—NH—$C_6H_3$—($CF_3$)$_2$(3',5') | |
| 23.085. | NHMe | 3-$C_6H_4$—O—$CF_3$ | |
| 23.086. | NHMe | 3-$C_6H_4$—O—COOEt | |
| 23.087. | NHMe | 3-$C_6H_4$—O—COOMe | |
| 23.088. | OMe | 3-$C_6H_4$—O—CO—NH—$C_6H_4$—($CF_3$)(4') | |
| 23.089. | OMe | 3-$C_6H_4$—O—CO—NH—$C_6H_4$—($OCH_3$)(4') | |
| 23.090. | OMe | 3-$C_6H_4$—O—CO—NH—$C_6H_4$—($OCF_3$)(4') | |
| 23.091. | NHMe | 3-$C_6H_4$—O—$CH_2$—OMe | |
| 23.092. | NHMe | 3-$C_6H_4$—O—$C_4H_9$(n) | |
| 23.093. | NHMe | 3-$C_6H_4$—O—$C_3H_7$(n) | |
| 23.094. | NHMe | 3-$C_6H_4$—O—$C_8H_{17}$(n) | |
| 23.095. | NHMe | 3-$C_6H_4$—O—$C_6H_4$($CH_3$)(3') | |
| 23.096. | NHMe | 3-$C_6H_4$—O—$CH_2$-morpholinyl(1) | |
| 23.097. | NHMe | 3-$C_6H_4$—O—$CH_2$-piperidinyl(1) | |

TABLE 23-continued

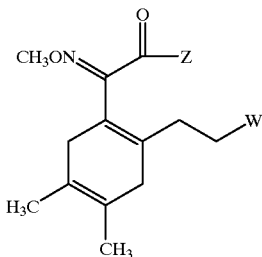

| Comp. No. | Z | W | Physical data m.p. |
|---|---|---|---|
| 23.098. | NHMe | 3-C$_6$H$_4$—O—CH$_2$—Cl | |
| 23.099. | OMe | 3-C$_6$H$_4$—O—C$_6$H$_4$(CH$_3$)(3') | |
| 23.100. | NHMe | 3-C$_6$H$_4$—O—CH$_2$—O—C$_6$H$_3$(Cl$_2$)(2',4') | |
| 23.101. | NHMe | 3-C$_6$H$_4$—O—CH$_2$—O—C$_6$H$_4$(CH$_3$)(2') | |
| 23.102. | NHMe | 3-C$_6$H$_4$—O—CH$_2$—O—C$_6$H$_4$(CH$_3$)(3') | |

TABLE 24

Compounds 24.001–24.102, in which Z and W have the meanings of the corresponding compounds of Table 23, W being substituted in the 4-position.

TABLE 25

Compounds of the formula

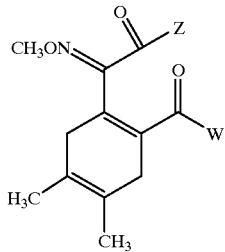

in which Z and W have the meanings of the corresponding compounds of Table 23.

TABLE 25a

Compounds of the formula

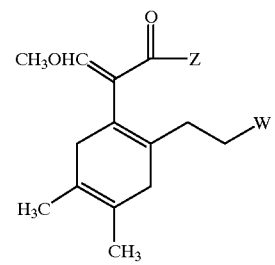

in which Z and W have the meanings of the corresponding compounds of Table 25.

TABLE 26

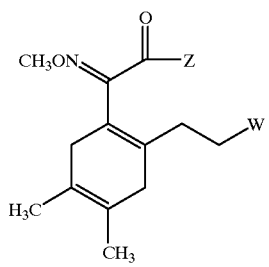

| Comp. No. | Z | W | Physical data m.p. |
|---|---|---|---|
| 26.001. | OMe | 3-C$_6$H$_4$—CO—C$_6$H$_3$Cl$_2$(2',4') | |
| 26.002. | OMe | 3-C$_6$H$_4$—CO—C$_6$H$_5$ | |
| 26.003. | OMe | 2-C$_6$H$_4$—CO—C$_6$H$_4$(OCH$_3$)(4') | |
| 26.004. | OMe | 3-C$_6$H$_4$—CO—C$_6$H$_3$(CF$_3$)(3',5') | |
| 26.005. | OMe | 2-C$_6$H$_4$—CO—C$_6$H$_4$(CF$_3$)(3') | |

TABLE 26-continued

| Comp. No. | Z | W | Physical data m.p. |
|---|---|---|---|
| 26.006. | OMe | 3-C$_6$H$_4$—CO—CO—C$_6$H$_4$(CF$_3$)(3') | |
| 26.007. | OMe | 2-C$_6$H$_4$—CO—CO—C$_6$H$_5$ | |
| 26.008. | OMe | 2-C$_6$H$_4$—CO—CO—C$_6$H$_4$(Cl)(3') | |
| 26.009. | OMe | 3-C$_6$H$_4$—CO—C$_6$H$_3$(CN)(3')(NO$_2$)(4') | |
| 26.010. | OMe | 3-C$_6$H$_4$—CO-pyrazinyl(2') | |
| 26.011. | OMe | 3-C$_6$H$_4$—CO-pyridyl(3') | |
| 26.012. | OMe | 3-C$_6$H$_4$—CO—CO-pyridyl(3') | |
| 26.013. | OMe | 3-C$_6$H$_4$—CO-pyridyl(2') | |
| 26.014. | OMe | 3-C$_6$H$_4$—CO-pyridyl(4') | |
| 26.015. | OMe | 3-C$_6$H$_4$—CO—C$_6$H$_4$(CF$_3$)(4') | |
| 26.016. | OMe | 2-C$_6$H$_4$—CO—C$_6$H$_4$(Cl)(4') | |
| 26.017. | OMe | 3-C$_6$H$_4$—CO—C$_6$H$_4$(NO$_2$)(4') | |
| 26.018. | OMe | 2-C$_6$H$_4$—CO-pyrimidinyl(2') | |
| 26.019. | OMe | 3-C$_6$H$_4$—CO-pyrimidinyl(4') | |
| 26.020. | OMe | 2-C$_6$H$_4$—CO-pyrimidinyl(5') | |
| 26.021. | OMe | 3-C$_6$H$_4$—CO—CO—NH—C$_6$H$_4$—(OMe)(4') | |
| 26.022. | OMe | 3-C$_6$H$_4$—CO—CH$_3$ | |
| 26.023. | OMe | 3-C$_6$H$_4$—CO—CO—NH—C$_6$H$_4$—(CF$_3$)(3') | |
| 26.024. | OMe | 3-C$_6$H$_4$—CO—C$_6$H$_4$(Br)(4') | |
| 26.025. | OMe | 2-C$_6$H$_4$—CO—C$_6$H$_2$(OCH$_3$)$_3$(3',4',5') | |
| 26.026. | OMe | 3-C$_6$H$_4$—CO—C$_6$H$_3$(CH$_3$)$_2$(3',5') | |
| 26.027. | OMe | 3-C$_6$H$_4$—CO-thiazolyl(2') | |
| 26.028. | OMe | 3-C$_6$H$_4$—CO-oxazolyl(2') | |
| 26.029. | OMe | 3-C$_6$H$_4$—CO-thienyl(2') | |
| 26.030. | OMe | 3-C$_6$H$_4$—CO-thienyl(3') | |
| 26.031. | OMe | 3-C$_6$H$_4$—CO-Et | |
| 26.032. | OMe | 4-C$_6$H$_4$—CO—H | |
| 26.033. | OMe | 2-C$_6$H$_4$—CO—H | |
| 26.034. | OMe | 4-C$_6$H$_4$—CO—CH$_3$ | |
| 26.035. | OMe | 3-C$_6$H$_4$—CO—CO—NH—C$_6$H$_4$—(Cl)(4') | |
| 26.036. | OMe | 4-C$_6$H$_4$—CO—CO—NH—C$_6$H$_3$—(Cl$_2$)(2',4') | |
| 26.037. | OMe | 3-C$_6$H$_4$—CO—CO—NH—C$_6$H$_4$—(NO$_2$)(4') | |
| 26.038. | OMe | 2-C$_6$H$_4$—CO—CF$_3$ | |
| 26.039. | OMe | 3-C$_6$H$_4$—CO—COOEt | |
| 26.040. | OMe | 2-C$_6$H$_4$—CO—COOMe | |
| 26.041. | OMe | 3-C$_6$H$_4$—CO—CO—NH—C$_6$H$_4$—(Br)(4') | |
| 26.042. | OMe | 4-C$_6$H$_4$—CO—CO—NH—C$_6$H$_4$—(I)(4') | |
| 26.043. | OMe | 4-C$_6$H$_4$—CO—CO—NH—C$_6$H$_4$—(CH$_3$)(2') | |
| 26.044. | OMe | 3-C$_6$H$_4$—CO—CH$_2$—OMe | |
| 26.045. | OMe | 3-C$_6$H$_4$—CO—C$_4$H$_9$(n) | |
| 26.046. | OMe | 4-C$_6$H$_4$—CO—C$_3$H$_7$(n) | |
| 26.047. | OMe | 4-C$_6$H$_4$—CO—C$_8$H$_{17}$(n) | |
| 26.048. | NHMe | 3-C$_6$H$_4$—CO—C$_6$H$_3$Cl$_2$(2',4') | |
| 26.049. | NHMe | 4-C$_6$H$_4$—CO—C$_6$H$_5$ | |
| 26.050. | NHMe | 3-C$_6$H$_4$—CO—C$_6$H$_4$(OCH$_3$)(4') | |
| 26.051. | NHMe | 4-C$_6$H$_4$—CO—C$_6$H$_3$(CF$_3$)$_2$(3',5') | |
| 26.052. | NHMe | 3-C$_6$H$_4$—CO—C$_6$H$_4$(CF$_3$)(3') | |
| 26.053. | NHMe | 3-C$_6$H$_4$—CO—CO—C$_6$H$_4$(CF$_3$)(3') | |
| 26.054. | NHMe | 4-C$_6$H$_4$—CO—CO—C$_6$H$_5$ | |
| 26.055. | NHMe | 3-C$_6$H$_4$—CO—CO—C$_6$H$_4$(Cl)(3') | |
| 26.056. | OMe | 3-C$_6$H$_4$—CO—CO—NH—C$_6$H$_3$—(CH$_3$)$_2$(2',6') | |
| 26.057. | NHMe | 3-C$_6$H$_4$—CO-pyrazinyl(2') | |
| 26.058. | NHMe | 3-C$_6$H$_4$—CO-pyridyl(3') | |
| 26.059. | NHMe | 4-C$_6$H$_4$—CO—CO-pyridyl(3') | |
| 26.060. | NHMe | 3-C$_6$H$_4$—CO-pyridyl(2') | |
| 26.061. | NHMe | 4-C$_6$H$_4$—CO-pyridyl(4') | |
| 26.062. | NHMe | 3-C$_6$H$_4$—CO—C$_6$H$_4$(CF$_3$)(4') | |
| 26.063. | NHMe | 3-C$_6$H$_4$—CO—C$_6$H$_4$(Cl)(4') | |
| 26.064. | OMe | 3-C$_6$H$_4$—CO—CO—NH—C$_6$H$_3$-(Me)(2')(Et)(6') | |
| 26.065. | NHMe | 3-C$_6$H$_4$—CO-pyrimidinyl(2') | |
| 26.066. | NHMe | 3-C$_6$H$_4$—CO-pyrimidinyl(4') | |
| 26.067. | NHMe | 3-C$_6$H$_4$—CO-pyrimidinyl(5') | |

TABLE 26-continued

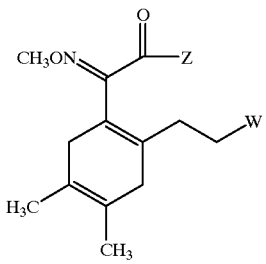

| Comp. No. | Z | W | Physical data m.p. |
|---|---|---|---|
| 26.068. | OMe | 2-C$_6$H$_4$—CO—CO—NH—C$_6$H$_3$-(Me)$_2$(2',4') | |
| 26.069. | NHMe | 3-C$_6$H$_4$—CO—CH$_3$ | |
| 26.070. | OMe | 2-C$_6$H$_4$—CO—CO—NH—C$_6$H$_4$—(Cl)(3') | |
| 26.071. | NHMe | 4-C$_6$H$_4$—CO—C$_6$H$_4$(Br)(4') | |
| 26.072. | NHMe | 3-C$_6$H$_4$—CO—C$_6$H$_2$(OCH$_3$)$_3$(3',4',5') | |
| 26.073. | NHMe | 3-C$_6$H$_4$—CO—C$_6$H$_3$(CH$_3$)$_2$(3',5') | |
| 26.074. | NHMe | 4-C$_6$H$_4$—CO-thiazolyl(2') | |
| 26.075. | NHMe | 3-C$_6$H$_4$—CO-oxazolyl(2') | |
| 26.076. | NHMe | 3-C$_6$H$_4$—CO-thienyl(2') | |
| 26.077. | NHMe | 4-C$_6$H$_4$—CO-thienyl(3') | |
| 26.078. | NHMe | 3-C$_6$H$_4$—CO-Et | |
| 26.079. | NHMe | 4-C$_6$H$_4$—CO—CH$_3$ | |
| 26.080. | NHMe | 2-C$_6$H$_4$—CO—CH$_3$ | |
| 26.081. | NHMe | 4-C$_6$H$_4$—CO—CH$_3$ | |
| 26.082. | OMe | 3-C$_6$H$_4$—CO—CO—NH—C$_6$H$_4$—(Cl)(2') | |
| 26.083. | OMe | 3-C$_6$H$_4$—CO—CO—NH—C$_6$H$_3$—(Cl)$_2$(3',5') | |
| 26.084. | OMe | 3-C$_6$H$_4$—CO—CO—NH—C$_6$H$_3$—(CF$_3$)$_2$(3',5') | |
| 26.085. | NHMe | 2-C$_6$H$_4$—CO—CF$_3$ | |
| 26.086. | NHMe | 3-C$_6$H$_4$—CO—COOEt | |
| 26.087. | NHMe | 2-C$_6$H$_4$—CO—COOMe | |
| 26.088. | OMe | 3-C$_6$H$_4$—CO—CO—NH—C$_6$H$_4$—(CF$_3$)(4') | |
| 26.089. | OMe | 3-C$_6$H$_4$—CO—CO—NH—C$_6$H$_4$—(OCH$_3$)(4') | |
| 26.090. | OMe | 4-C$_6$H$_4$—CO—CO—NH—C$_6$H$_4$—(OCF$_3$)(4') | |
| 26.091. | NHMe | 4-C$_6$H$_4$—CO—CH$_2$—OMe | |
| 26.092. | NHMe | 3-C$_6$H$_4$—CO—C$_4$H$_9$(n) | |
| 26.093. | NHMe | 3-C$_6$H$_4$—CO—C$_3$H$_7$(n) | |
| 26.094. | NHMe | 3-C$_6$H$_4$—CO—C$_8$H$_{17}$(n) | |
| 26.095. | NHMe | 4-C$_6$H$_4$—CO—C$_6$H$_4$(CH$_3$)(3') | |
| 26.096. | NHMe | 4-C$_6$H$_4$—CO—CH$_2$-morpholinyl(1) | |
| 26.097. | NHMe | 3-C$_6$H$_4$—CO—CH$_2$-piperdinyl(1) | |
| 26.098. | NHMe | 3-C$_6$H$_4$—CO—CH$_2$—Cl | |
| 26.099. | OMe | 3-C$_6$H$_4$—CO—C$_6$H$_4$(CH$_3$)(3') | |
| 26.100. | NHMe | 3-C$_6$H$_4$—CO—CH$_2$—O—C$_6$H$_3$(Cl$_2$)(2',4') | |
| 26.101. | NHMe | 3-C$_6$H$_4$—CO—CH$_2$—O—C$_6$H$_4$(CH$_3$)(2') | |
| 26.102. | NHMe | 3-C$_6$H$_4$—CO—CH$_2$—O—C$_6$H$_4$(CH$_3$)(3') | |
| 26.103. | OMe | 4-C$_6$H$_4$—CO—C$_6$H$_4$(F)(4') | |
| 26.104. | OMe | 4-C$_6$H$_4$—CO—C$_6$H$_4$(—C≡C—C$_6$H$_5$)(4') | |
| 26.105. | OMe | 4-C$_6$H$_4$—CO—C$_6$H$_4$(—CH$_2$—CH$_2$—C$_6$H$_5$)(4') | |

TABLE 27

Compounds of the formula

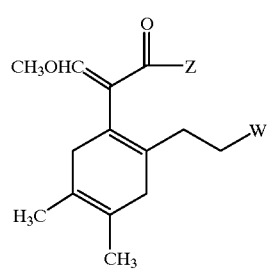

in which Z and W have the meanings of the corresponding compounds of Table 26.

TABLE 28

[Structure: substituted cyclohexadiene with CH$_3$ON= group, C(=O)-Z, and CH$_2$CH$_2$-W substituents, plus two CH$_3$ groups]

| Comp. No. | Z | W | Physical data m.p. |
|---|---|---|---|
| 28.001. | OMe | 3-C$_6$H$_4$—C$_6$H$_3$Cl$_2$(2',4') | |
| 28.002. | OMe | 3-C$_6$H$_4$—C$_6$H$_5$ | |
| 28.003. | OMe | 3-C$_6$H$_4$—C$_6$H$_4$(OCH$_3$)(4') | |
| 28.004. | OMe | 3-C$_6$H$_4$—C$_6$H$_3$(CF$_3$)$_2$(3',5') | |
| 28.005. | OMe | 3-C$_6$H$_4$—C$_6$H$_4$(CF$_3$)(3') | |
| 28.006. | OMe | 3-C$_6$H$_4$—SO$_2$—NH—C$_6$H$_4$(CF$_3$)(3') | |
| 28.007. | OMe | 3-C$_6$H$_4$—NH—C$_6$H$_4$(CF$_3$)(3') | |
| 28.008. | OMe | 3-C$_6$H$_4$—NH—CO—C$_6$H$_4$(CF$_3$)(3') | |
| 28.009. | OMe | 3-C$_6$H$_4$—C$_6$H$_3$(CN)(3')(NO$_2$)(4') | |
| 28.010. | OMe | 3-C$_6$H$_4$-pyrazinyl(2') | |
| 28.011. | OMe | 3-C$_6$H$_4$-pyridyl(3') | |
| 28.012. | OMe | 3-C$_6$H$_4$—O—CH$_2$-dioxolanyl(2') | |
| 28.013. | OMe | 3-C$_6$H$_4$-pyridyl(2') | |
| 28.014. | OMe | 3-C$_6$H$_4$-pyridyl(4') | |
| 28.015. | OMe | 3-C$_6$H$_4$—C$_6$H$_4$(CF$_3$)(4') | |
| 28.016. | OMe | 3-C$_6$H$_4$—C$_6$H$_4$(Cl)(4') | |
| 28.017. | OMe | 3-C$_6$H$_4$—C$_6$H$_4$(NO$_2$)(4') | |
| 28.018. | OMe | 3-C$_6$H$_4$-pyrimidinyl(2') | |
| 28.019. | OMe | 3-C$_6$H$_4$-pyrimidinyl(4') | |
| 28.020. | OMe | 3-C$_6$H$_4$-pyrimidinyl(5') | |
| 28.021. | OMe | 3-C$_6$H$_4$—O—CH$_2$—CH(OMe)$_2$ | |
| 28.022. | OMe | 3-C$_6$H$_4$—O—CH$_2$—CH(OEt)$_2$ | |
| 28.023. | OMe | 3-C$_6$H$_4$—O—SO$_2$—NEt$_2$ | |
| 28.024. | OMe | 3-C$_6$H$_4$—C$_6$H$_4$(Br)(4') | |
| 28.025. | OMe | 3-C$_6$H$_4$—C$_6$H$_2$(OCH$_3$)$_3$(3',4',5') | |
| 28.026. | OMe | 3-C$_6$H$_4$—C$_6$H$_3$(CH$_3$)$_2$(3',5') | |
| 28.027. | OMe | 3-C$_6$H$_4$-thiazolyl(2') | |
| 28.028. | OMe | 3-C$_6$H$_4$-oxazolyl(2') | |
| 28.029. | OMe | 3-C$_6$H$_4$-thienyl(2') | |
| 28.030. | OMe | 3-C$_6$H$_4$-thienyl(3') | |
| 28.031. | OMe | 3-C$_6$H$_4$—S—C$_6$H$_5$ | |
| 28.032. | OMe | 3-C$_6$H$_4$—C$_6$H$_3$(CH$_3$)$_2$(3',5') | |
| 28.033. | OMe | 2-C$_6$H$_4$—CH$_2$—H | |
| 28.034. | OMe | 4-C$_6$H$_4$—CH$_2$—CH$_3$ | |
| 28.035. | OMe | 3-C$_6$H$_4$—CH$_2$—CO—NH—C$_6$H$_4$(Cl)(4') | |
| 28.036. | OMe | 3-C$_6$H$_4$—CH$_2$—CO—NH—C$_6$H$_3$(Cl$_2$)(2',4') | |
| 28.037. | OMe | 3-C$_6$H$_4$—CH$_2$—CO—NH—C$_6$H$_4$(NO$_2$)(4') | |
| 28.038. | OMe | 3-C$_6$H$_4$—CH$_2$—CF$_3$ | |
| 28.039. | OMe | 3-C$_6$H$_4$—CH$_2$—COOEt | |
| 28.040. | OMe | 3-C$_6$H$_4$—CH$_2$—COOMe | |
| 28.041. | OMe | 3-C$_6$H$_4$—CH$_2$—CO—NH—C$_6$H$_4$—(Br)(4') | |
| 28.042. | OMe | 3-C$_6$H$_4$—CH$_2$—CO—NH—C$_6$H$_4$—(I)(4') | |
| 28.043. | OMe | 3-C$_6$H$_4$—CH$_2$—CO—NH—C$_6$H$_4$—(CH$_3$)(2') | |
| 28.044. | OMe | 3-C$_6$H$_4$—CH$_2$—CH$_2$—OMe | |
| 28.045. | OMe | 3-C$_6$H$_4$—CH$_2$—C$_4$H$_9$(n) | |
| 28.046. | OMe | 3-C$_6$H$_4$—CH$_2$—C$_3$H$_7$(n) | |
| 28.047. | OMe | 3-C$_6$H$_4$—CH$_2$—C$_8$H$_{17}$(n) | |
| 28.048. | NHMe | 3-C$_6$H$_4$—C$_6$H$_3$Cl$_2$(2',4') | |
| 28.049. | NHMe | 3-C$_6$H$_4$—C$_6$H$_5$ | |
| 28.050. | NHMe | 3-C$_6$H$_4$—C$_6$H$_4$(OCH$_3$)(4') | |
| 28.051. | NHMe | 3-C$_6$H$_4$—C$_6$H$_3$(CF$_3$)$_2$(3',5') | |
| 28.052. | NHMe | 3-C$_6$H$_4$—C$_6$H$_4$(CF$_3$)(3') | |
| 28.053. | NHMe | 3-C$_6$H$_4$—CH$_2$—CO—C$_6$H$_4$(CF$_3$)(3') | |
| 28.054. | NHMe | 3-C$_6$H$_4$—CH$_2$—CO—C$_6$H$_5$ | |
| 28.055. | NHMe | 3-C$_6$H$_4$—CH$_2$—CO—C$_6$H$_4$(Cl)(3') | |
| 28.056. | OMe | 3-C$_6$H$_4$—CH$_2$—CO—NH—C$_6$H$_3$—(CH$_3$)$_2$(2',6') | |
| 28.057. | NHMe | 3-C$_6$H$_4$-pyrazinyl(2') | |
| 28.058. | NHMe | 3-C$_6$H$_4$-pyridyl(3') | |
| 28.060. | NHMe | 3-C$_6$H$_4$-pyridyl(2') | |
| 28.061. | NHMe | 3-C$_6$H$_4$-pyridyl(4') | |

TABLE 28-continued

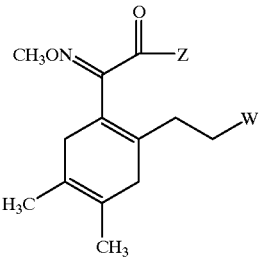

| Comp. No. | Z | W | Physical data m.p. |
|---|---|---|---|
| 28.062. | NHMe | 3-C$_6$H$_4$—C$_6$H$_4$(CF$_3$)(4') | |
| 28.063. | NHMe | 3-C$_6$H$_4$—C$_6$H$_4$(Cl)(4') | |
| 28.064. | OMe | 3-C$_6$H$_4$—CH$_2$—CO—NH—C$_6$H$_3$-(Me)(2')(Et)(6') | |
| 28.065. | NHMe | 3-C$_6$H$_4$-pyrimidinyl(2') | |
| 28.066. | NHMe | 3-C$_6$H$_4$-pyrimidinyl(4') | |
| 28.067. | NHMe | 3-C$_6$H$_4$-pyrimidinyl(5') | |
| 28.068. | OMe | 3-C$_6$H$_4$—CH$_2$—CO—NH—C$_6$H$_3$-(Me)$_2$(2',4') | |
| 28.069. | NHMe | 3-C$_6$H$_4$—CH$_2$—CH$_3$ | |
| 28.070. | OMe | 3-C$_6$H$_4$—CH$_2$—CO—NH—C$_6$H$_4$—(Cl)(3') | |
| 28.071. | NHMe | 3-C$_6$H$_4$—C$_6$H$_4$(Br)(4') | |
| 28.072. | NHMe | 3-C$_6$H$_4$—C$_6$H$_2$(OCH$_3$)$_3$(3',4',5') | |
| 28.073. | NHMe | 3-C$_6$H$_4$—C$_6$H$_3$(CH$_3$)$_2$(3',5') | |
| 28.074. | NHMe | 3-C$_6$H$_4$-thiazolyl(2') | |
| 28.075. | NHMe | 3-C$_6$H$_4$-oxazolyl(2') | |
| 28.076. | NHMe | 3-C$_6$H$_4$-thienyl(2') | |
| 28.077. | NHMe | 3-C$_6$H$_4$-thienyl(3') | |
| 28.078. | NHMe | 3-C$_6$H$_4$—CH$_2$-Et | |
| 28.079. | NHMe | 4-C$_6$H$_4$—CH$_2$—CH$_3$ | |
| 28.080. | NHMe | 2-C$_6$H$_4$—CH$_2$—CH$_3$ | |
| 28.081. | NHMe | 4-C$_6$H$_4$—CH$_2$—CH$_3$ | |
| 28.082. | OMe | 3-C$_6$H$_4$—CH$_2$—CO—NH—C$_6$H$_4$—(Cl)(2') | |
| 28.083. | OMe | 3-C$_6$H$_4$—CH$_2$—CO—NH—C$_6$H$_3$—(Cl)$_2$(3',5') | |
| 28.084. | OMe | 3-C$_6$H$_4$—CH$_2$—CO—NH—C$_6$H$_3$—(CF$_3$)$_2$(3',5') | |
| 28.085. | NHMe | 3-C$_6$H$_4$—CH$_2$—CF$_3$ | |
| 28.086. | NHMe | 3-C$_6$H$_4$—CH$_2$—COOEt | |
| 28.087. | NHMe | 3-C$_6$H$_4$—CH$_2$—COOMe | |
| 28.088. | OMe | 3-C$_6$H$_4$—CH$_2$—CO—NH—C$_6$H$_4$—(CF$_3$)(4') | |
| 28.089. | OMe | 3-C$_6$H$_4$—CH$_2$—CO—NH—C$_6$H$_4$—(OCH$_3$)(4') | |
| 28.090. | OMe | 3-C$_6$H$_4$—CH$_2$—CO—NH—C$_6$H$_4$—(OCF$_3$)(4') | |
| 28.091. | NHMe | 3-C$_6$H$_4$—CH$_2$—CH$_2$—OMe | |
| 28.092. | NHMe | 3-C$_6$H$_4$—CH$_2$—C$_4$H$_9$(n) | |
| 28.093. | NHMe | 3-C$_6$H$_4$—CH$_2$—C$_3$H$_7$(n) | |
| 28.094. | NHMe | 3-C$_6$H$_4$—CH$_2$—C$_8$H$_{17}$(n) | |
| 28.095. | NHMe | 3-C$_6$H$_4$—C$_6$H$_4$(CH$_3$)(3') | |
| 28.096. | NHMe | 3-C$_6$H$_4$—CH$_2$—CH$_2$-morpholinyl(1) | |
| 28.097. | NHMe | 3-C$_6$H$_4$—CH$_2$—CH$_2$-piperidinyl(1) | |
| 28.098. | NHMe | 3-C$_6$H$_4$—CH$_2$—CH$_2$—Cl | |
| 28.099. | OMe | 3-C$_6$H$_4$—C$_6$H$_4$(CH$_3$)(3') | |
| 28.100. | NHMe | 3-C$_6$H$_4$—CH$_2$—CH$_2$—O—C$_6$H$_3$(Cl$_2$)(2',4') | |
| 28.101. | NHMe | 3-C$_6$H$_4$—CH$_2$—CH$_2$—O—C$_6$H$_4$(CH$_3$)(2') | |
| 28.102. | NHMe | 3-C$_6$H$_4$—CH$_2$—CH$_2$—O—C$_6$H$_4$(CH$_3$)(3') | |
| 28.103. | OMe | 3-C$_6$H$_4$—C$_6$H$_4$(F)(2')(Cl)(3') | |

TABLE 28a

Compounds of the formula

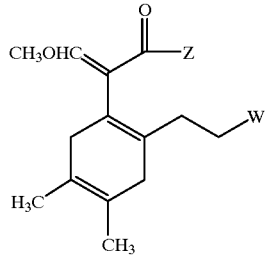

in which Z and W have the meanings of the corresponding compounds of Table 28.

2. FORMULATION EXAMPLES

For similar purposes of pesticidal use are described for example in WO 97/33890.

BIOLOGICAL EXAMPLES

A. Microbicidal Actions

Example B-1

Action Against *Puccinia graminis* on Wheat a) Residual-protective Action

Wheat plants are sown and, 6 days thereafter, sprayed to drip point with an aqueous spray mixture prepared with a wettable powder of the active ingredient (0.02% active substance) and, 24 hours later, infected with a uredospore suspension of the fungus. After an incubation time of 48 hours (conditions: 95 to 100 per cent relative atmospheric humidity at 20°), the plants are placed in a greenhouse at 22°. The fungus infestation is assessed 12 days after the infection.

b) Systemic Action

An aqueous spray mixture prepared with a wettable powder of the active ingredient is poured next to wheat plants 5 days after they have been sown. (0.006% active substance based on the soil volume). Care is taken that the spray mixture does not come into contact with aerial plant organs. 48 hours later, the plants are infected with a uredospore suspension of the fungus. After an incubation time of 48 hours (conditions: 95 to 100 per cent relative atmospheric humidity at 20°), the plants are placed in a greenhouse at 22°. The fungus infestation is assessed 12 days after the infection. Compounds from the tables exhibit good activity.

Example B-2

Action Against *Phytophthora infestans* on Tomatoes a) Residual-Protective Action Tomato plants are grown for three weeks and then sprayed to drip point with an aqueous spray mixture prepared with a wettable powder of the active ingredient (0.02% active substance) and, 24 hours later, infected with a sporangia suspension of the fungus. The fungus infestation is assessed 5 days after the infection, during which a relative atmospheric humidity of 90 to 100 per cent and a temperature of 20° are maintained.

b) Systemic Action

An aqueous spray mixture prepared with a wheatable powder of the active ingredient is poured next to tomato plants which have been grown for three weeks (0.006% active substance based on the soil volume). Care is taken that the spray mixture does not come into contact with aerial plant organs. After 48 hours, the plants are infected with a sporangia suspension of the fungus. The fungus infestation is assessed 5 days after the infection, during which a relative atmospheric humidity of 90 to 100 per cent at a temperature of 20° are maintained. The compounds from the tables exhibit good activity.

Example B-3

Residual-protective Action Against *Cercospora arachidicola* on Peanuts

Peanut plants 10 to 15 cm in height are sprayed to drip point with an aqueous spray mixture prepared with a wettable powder of the active ingredient (0.02% active substance) and, 48 hours later, infected with a conidia suspension of the fungus. The plants are incubated for 72 hours at 21° and high atmospheric humidity and subsequently placed in a greenhouse until the typical foliar lesions develop. The activity of the active substance is assessed 12 days after the infection on the basis of number and size of the foliar lesions. Compounds from the tables exhibit good activity.

Example B-4

Action Against *Plasmopara viticola* on Grapevines

Grapevine seedlings in the 4–5-leaf stage are sprayed to drip point with an aqueous spray mixture prepared with a wettable powder of the active ingredient (0.02% active substance) and, 24 hours later, infected with a sporangia suspension of the fungus. The fungus infestation is assessed 6 days after the infection, during which a relative atmospheric humidity of 95 to 100 per cent and a temperature of 20° are maintained. Compounds from the tables exhibit good activity.

Example B-5

Action Against *Colletotrichum lagenarium* on Cucumbers

Cucumber plants are grown for 2 weeks and then sprayed with a spray mixture prepared with a wettable powder of the active ingredient (concentration 0.002%). After 2 days, the plants are infected with a spore suspension ($1.5 \times 10^5$ spores/ml) of the fungus and incubated for 36 hours at 23° C. and high atmospheric humidity. Incubation is then continued at normal atmospheric humidity and at approximately 22°C. 8 days after the infection, the fungus infestation which has taken place is assessed. Compounds from the tables exhibit good activity.

Example B-6

Residual Protective Action against *Venturia inaequalis* on Apples

Apple cuttings with fresh shoots 10 to 20 cm in length are sprayed to drip point with an aqueous spray mixture prepared with a wettable powder of the active ingredient (0.02% active substance) and, 24 hours later, infected with a conidia suspension of the fungus. The plants are incubated for 5 days at a relative atmospheric humidity of 90 to 100 per cent and placed for a further 10 days in a greenhouse at 20 to 24°. The fungus infestation is assessed 12 days after the infection.. Compounds from the tables exhibit good activity.

Example B-7

Action Against *Erysiphe graminis* on Barley a) Residual-Protective Action

Barley plants approximately 8 cm in height are sprayed to drip point with an aqueous spray mixture prepared with a wettable powder of the active ingredient (0.02% active substance) and, 3 to 4 hours later, dusted with conidia of the fungus. The infected plants are placed in a greenhouse at 22°. The fungus infestation is assessed 12 days after the infection. Compounds from the tables exhibit good activity.

b) Systemic Action

An aqueous spray mixture prepared with a wettable powder of the active ingredient is poured next to barley plants approximately 8 cm in height (0.002% active substance based on the soil volume). Care is taken that the spray mixture does not come into contact with aerial plant organs. 48 hours later, the plants are dusted with conidia of the fungus. The infected plants are placed in a greenhouse at 22°. The fungus infestation is assessed 12 days after the infection. Compounds from the tables exhibit good activity.

Example B-8

Action Against *Podosphaera leucotricha* on Apple Shoots

Apple cuttings with fresh shoots approximately 15 cm in length are sprayed with a spray mixture (0.06% active substance). After 24 hours, the treated plants are infected with a conidia suspension of the fungus and placed in a controlled-environment cabinet at a relative atmospheric humidity of 70% and at 20° C. The fungus infestation is assessed 12 days after the infection. Compounds from the tables exhibit good activity.

BIOLOGICAL EXAMPLES

B. Insecticidal Actions

Example B-9

Action Against *Aphis craccivora*

Pea seedlings are infected with *Aphis craccivora*, subsequently sprayed with a spray mixture comprising 100 ppm of active ingredient and then incubated at 20°. 3 and 6 days later, the per centage reduction in population (% activity) is determined by comparing the number of dead aphids on treated and untreated plants. In this test, compounds of the tables exhibit good activity, i.e. a destruction rate of over 80%.

Example B-10

Action Against *Diabrotica balteata*

Maize seedlings are sprayed with an aqueous emulsion spray mixture comprising 400 ppm of active ingredient, then, after the spray coating has dried on, populated with 10 second instar larvae of *Diabrotica balteata* and subsequently introduced into a plastic container. 6 days later, the per centage reduction in population (% activity) is determined by comparing the number of dead larvae between the treated and untreated plants. In this test, compounds of the tables exhibit good activity.

Example B-11

Action Against *Heliothis virescens*

Young soya plants are sprayed with an aqueous emulsion spray mixture comprising 100 ppm of active ingredient, then, after the spray coating has dried on, populated with 10 first instar caterpillars of *Heliothis virescens* and subsequently introduced into a plastic container. 6 days later, the per centage reduction in population and the feeding damage (% activity) are determined by comparing the number of dead caterpillars and the feeding damage between the treated and untreated plants. In this test, compounds of the tables exhibit good activity.

Example B-12

Action Against *Spodoptera littoralis*

Young soya plants are sprayed with an aqueous emulsion spray mixture comprising 100 ppm of active ingredient, then, after the spray coating has dried on, populated with 10 third instar caterpillars of *Spodoptera littoralis* and subsequently introduced into a plastic container. 3 days later, the per centage reduction in population and the percentage reduction in feeding damage (% activity) are determined by comparing the number of dead caterpillars and the feeding damage between the treated and untreated plants. In this test, compounds of the tables exhibit good activity.

B-13: Action Against *Nilaparvata lugens*

Rice plants are treated with an aqueous emulsion spray mixture which comprises 100 ppm of the active ingredient. After the spray coating has dried on, the rice plants are populated with 2nd and 3rd instar leafhopper larvae. The test is evaluated 21 days later. The percentage reduction in population (% activity) is determined by comparing the number of surviving leafhoppers on the treated with those on the untreated plants. The compounds of the tables exhibit an activity of over 90%.

B-14: Action Against *Plutella xylostella* Caterpillars

Young cabbage plants are sprayed with an aqueous emulsion spray mixture which comprises 100 ppm of the active ingredient. After the spray coating has dried on, the cabbage plants are populated with 10 third instar caterpillars of *Plutella xylostella* and introduced into a plastic container. The test is evaluated 3 days later. The per centage reduction in population or the per centage reduction in feeding damage (% activity) is determined by comparing the number of dead caterpillars and the feeding damage on the treated with those on the untreated plants. Compounds from the tables exhibit good activity.

Example B-15: Action Against *Musca domestica*

A sugar lump is treated with a solution of the test substance in such a way that, after drying overnight, the concentration of test substance in the sugar is 250 ppm. This treated lump is placed on an aluminium dish together with a wet cotton wool ball and 10 adult *Musca domestica* of an OP-resistant strain, covered with a glass beaker and incubated at 25° C. The mortality rate is determined after 24 hours. Compounds from the tables exhibit good activity.

BIOLOGICAL EXAMPLES

C. Acaricidal Actions

B-16: Action Against *Tetranychus urticae*

Young bean plants are populated with a mixed population of *Tetranychus urticae* and, one day later, sprayed with an aqueous emulsion spray mixture which comprises 400 ppm of the active ingredient. The plants are subsequently incubated for 6 days at 25° C. and then evaluated. The per centage reduction in population (% action) is determined by comparing the number of dead eggs, larvae and adults on the treated with those on the untreated plants. Compounds from the tables exhibit good activity.

B-17: Action on Mixed Population of *Tetranychus cinnabarinus* Dilution Series

Dwarf beans in the 2-leaf stage are populated with a mixed population (eggs, larvae/nymphs, adults) of an OP-tolerant strain of *Tetranychus cinnabarinus*. 24 hours after infection, the products are applied to the plants in an automatic spray cabin at the dosages 200, 100, 50 mg of a.s/l. The substances are formulated and are diluted with water to give the appropriate dosages. The test is evaluated 2 and 7 days after application for per centage mortality of eggs, larvae/nymphs and adults. Compounds of the tables exhibit mortality rates above 70% in dilutions of as little as 50 mg of a.s./liter.

B-18: Action Against *Boophilus microplus*

Female adult ticks which have sucked themselves full are glued to a PVC pane and covered with a cotton wool ball, and 10 ml of aqueous test solution comprising 125 ppm of active ingredient are poured over. The cotton wool ball is removed and the ticks are incubated for 4 weeks for oviposition. The action manifests itself either in the case of the female as mortality or sterility or in the case of the eggs as ovicidal action.

What is claimed is:

1. A compound of the formula I

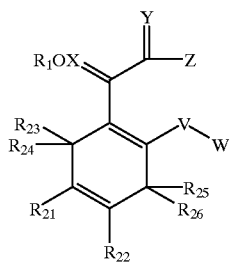

I in which:
X is N;
Y is O; S, S=O or $NR_5$;
Z is $OR_2$, $SR_2$, $N(R_3)R_4$;
V is a direct bond or a 1 to 4 membered, saturated or unsaturated carbon chain which is unsubstituted or substituted by $C_1$–$C_3$alkyl, halogen, hydroxy, $C_1$–$C_4$alkoxy, halo-$C_1$–$C_4$alkoxy or oxo;
W is hydrogen or $C_1$ –$C_6$ alkyl or a substituted or unsubstituted phenyl group of the formula:

wherein n is an integer of from 0 to 5 and each D is identical or different and represents a moiety selected from the group consisting of halogen, cyano, nitro, $C_1$ to $C_{12}$ alkyl, halo-$C_1$ to $C_{12}$ alkyl, $C_2$ to $C_{12}$ alkenyl, halo-$C_2$ to $C_{12}$ alkenyl, $C_2$ to $C_{12}$ alkynyl, halo-$C_2$ to $C_{12}$ alkynyl, $C_3$ to $C_6$ cycloalkyl, halo-$C_3$ to $C_6$ cycloalkyl, $C_3$ to $C_6$ cycloalkylmethyl, halo-$C_3$ to $C_6$ cycloalkylmethyl, $C_3$ to $C_6$ cycloalkylmethyloxy, halo-$C_3$ to $C_6$ cycloalkylmethyloxy, $C_1$ to $C_4$ alkoxy, halo-$C_1$ to $C_4$ alkoxy, $C_2$ to $C_6$ alkenyloxy, halo-$C_2$ to $C_6$ alkenyloxy, $C_2$ to $C_6$ alkynyloxy, halo-$C_2$ to $C_{12}$ alkynyloxy, $C_2$ to $C_{12}$ alkoxyalkyl, $C_1$ to $C_4$ alkoxy carbonyl, and $C_1$ to $C_6$ alkylcarbonyl;

$R_1$ is cyclopropyl, $C_1$–$C_6$alkyl or halo-$C_1$–$C_6$alkyl;
$R_2$ and $R_3$ independently of one another are $C_1$–$C_6$alkyl or halo-$C_1$–$C_6$alkyl;
$R_4$ and $R_5$ independently of one another are hydrogen, $C_1$–$C_6$alkyl or $C_1$–$C_6$alkoxy;
$R_{21}$ and $R_{22}$ independently of one another are hydrogen, halogen, $C_1$–$C_8$alkyl or $C_1$–$C_8$alkoxy or $C_1$–$C_8$alkylthio;
$R_{23}$, $R_{24}$, $R_{25}$, $R_{26}$ independently of one another are hydrogen, halogen, $C_1$–$C_8$alkyl or $C_1$–$C_8$alkoxy.

2. A compound according to claim 1 in which:
$R_1$ is methyl;
$R_2$, $R_3$ and $R_5$ independently of one another are $C_1$–$C_2$alkyl;
$R_4$ is hydrogen.

3. A compound according to claim 1 in which:
$R_{21}$ and $R_{22}$ independently of one another are hydrogen, chlorine, bromine, $C_1$–$C_4$alkyl, or $C_1$–$C_4$alkoxy;
$R_{23}$, $R_{24}$, $R_{25}$, $R_{26}$ are hydrogen.

4. A compound according to claim 1 in which:
Y is O;
Z is $OCH_3$ or $NHCH_3$;
V is —$CH_2$—, —$CH(CH_3)$—, —$CH(CH_3)_2$—, —$(CH_2)_2$—, —$(CH_2)_3$—, —CH—CH—, —C=C—, C—O, —$CH_2C(=O)$— or —$(C=O)CH_2$—
W is a substituted or unsubstituted phenyl;
$R_{21}$ and $R_{22}$ independently of one another are hydrogen, chlorine or methyl;
$R_{23}$, $R_{24}$, $R_{25}$, $R_{26}$ are hydrogen.

5. The compound

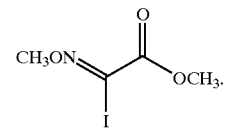

XIVa2

6. A composition for controlling pests which comprises, as active ingredient, an effective amount of a compound according to claim 1 together with a suitable carrier material.

7. A method of controlling and preventing pests, which comprises applying a compound according to claim 1 to the pests or their environment.

* * * * *